United States Patent
Arnold et al.

[11] Patent Number: 6,130,217
[45] Date of Patent: Oct. 10, 2000

[54] COMPOUNDS ENHANCING ANTITUMOR ACTIVITY OF OTHER CYTOTOXIC AGENTS

[75] Inventors: Lee Daniel Arnold, Quaker Hill; Jotham Wadsworth Coe, Niantic; Takushi Kaneko, Guilford; Mikel Paul Moyer, Clinton, all of Conn.

[73] Assignee: Pfizer Inc, New York, N.Y.

[21] Appl. No.: 08/513,880

[22] Filed: Sep. 20, 1995

Related U.S. Application Data

[63] Continuation-in-part of application No. 08/040,233, filed as application No. PCT/US94/01724, Feb. 28, 1994, abandoned.

[51] Int. Cl.$^7$ ............ A61K 31/495; C07D 417/12; C07D 417/14; C07D 403/12

[52] U.S. Cl. ............ 514/253; 514/252; 514/318; 514/211; 514/321; 514/326; 514/367; 514/278; 514/290; 514/319; 514/320; 514/322; 514/323; 514/324; 544/364; 544/366; 544/368; 544/370; 546/194; 546/198; 546/209; 546/17; 546/101; 546/110; 546/202; 548/159; 548/160; 548/165; 540/551

[58] Field of Search ............ 544/364, 366, 544/368, 370; 514/252, 253

[56] References Cited

U.S. PATENT DOCUMENTS

| | | |
|---|---|---|
| 4,996,321 | 2/1991 | Baldwin et al. ............ 546/194 |
| 5,364,843 | 11/1994 | King ............ 514/15 |
| 5,622,953 | 4/1997 | Janssen et al. ............ 514/255 |

FOREIGN PATENT DOCUMENTS

| | | |
|---|---|---|
| 0224086 | 6/1987 | European Pat. Off. . |
| 0363212 | 11/1990 | European Pat. Off. ...... C07D 215/20 |
| 0409406 | 1/1991 | European Pat. Off. ..... A61K 31/135 |
| 0511790 | 11/1992 | European Pat. Off. . |
| 2121924 | of 1990 | Japan ............ A61K 31/495 |
| 2121966 | of 1990 | Japan . |
| 4134070 | of 1992 | Japan . |
| 9218089 | 10/1992 | WIPO . |

OTHER PUBLICATIONS

Bellamy et al, *Cancer Investigation* 8(5), p547–562, (1990).
Fukazawa et al. Chemical Abstracts, vol. 113, No. 152477 (Abstract for JP 02121966, May 9, 1990).
Derwent 92–204506/25 Mitsui Toatsu Chem, Inc., Abstract for JP 4–134070 (May 7, 1992).
W. Sato et al., Cancer Research 51, 2420–2424, May 1, 1991.
V. Brizzi et al., II Farmaco, 47 (6), 953–966; 1992.
J. B. Press et al., J. Med. Chem., 35 (24), Nov., 1992, 4509–4515.
Sircar et al., J. Med. Chem., 1992, 35, 4442–4449.
Fukazawa et al Chemical Abstracts, vol. 117, No. 23, Abs. No. 233859m. (1992).
Fukazawa et al Chemical Abstracts, vol. 113, No. 13, Abs. No. 109311e. (1990).

*Primary Examiner*—Emily Bernhardt
*Attorney, Agent, or Firm*—Peter C. Richardson; Paul H. Ginsburg; Mark Dryer

[57] ABSTRACT

This invention relates to certain heterocyclic compounds and their pharmaceutically acceptable salts, which are useful for sensitizing multidrug-resistant tumor cells to anticancer agents and multidrug resistant forms of malaria, tuberculosis, leishmania and amoebic dysentery to chemotherapeutants. The compounds and their pharmaceutically acceptable salts are also inhibitors of the active drug transport capability of P-glycoprotein which is encoded by the human MDR1 gene, as well as of certain other related ATP-binding-cassette transporters from eukaryotic and prokaryotic organisms (e.g., pfmdr from *Plasmodium falciprum*, and murine mdr1 and mdr3 gene products).

4 Claims, No Drawings

COMPOUNDS ENHANCING ANTITUMOR ACTIVITY OF OTHER CYTOTOXIC AGENTS

This patent application is the national stage application, filed pursuant to 35 U.S.C. §371, of PCT international patent application number PCT/US94/01724, filed Feb. 28, 1994, which is a continuation-in-part of U.S. patent application Ser. No. 08/040,233, filed Mar. 30, 1993, now abandoned.

BACKGROUND OF THE INVENTION

This invention relates to certain heterocyclic compounds and their use as sensitizers of tumor cells to anticancer agents and sensitizers of multidrug resistant forms of malaria (*Plasmodium falciprum*), tuberculosis, leishmania and amoebic dysentry. The compounds are also useful in facilitating delivery of cancer chemotherapeutants and other drugs across the blood-brain barrier, treatment of AIDS (especially in enhancing intracellular accumulation of drugs in infected lymphocytes) in humans and sensitization of multidrug resistant infections in humans and animals (especially Eimerian coccidial).

In cancer chemotherapy the effectiveness of anticancer drugs is often limited by the resistance of tumor cells. Some tumors such as of the colon, pancreas, kidney and liver are generally innately resistant, and other responding tumors often develop resistance during the course of chemotherapy. The phenomena of multidrug resistance (MDR) is typically characterized by the tumor cell's cross-resistance to adriamycin, daunomycin, vinblastine, topotecan, teniposide, vincristine, taxol, actinomycin D and etoposide. The resistance of cells is often associated with overexpression of the MDR1 gene. This gene encodes for a 140–220 kd transmembrane phosphoglycoprotein (P-glycoprotein) which functions as an ATP-dependent efflux pump. Thus, it has been postulated that this efflux mechanism keeps the intracellular level of the anticancer drug low, allowing the tumor cells to survive.

In recent years various substances such as verapamil, nifedipine trifluoroperazine, and diltiazem have been used in in vitro experimental systems to reverse the MDR phenomena. More recently some of these agents have been tested clinically as MDR reversing agents. Little efficacy has been observed with verapamil or trifluoroperazine. Thus, there is a need for an effective MDR reversing agent.

Quinoline derivatives and other related compounds are claimed as anti-cancer drug reinforcing agents in European Patent Application 0 363 212.

SUMMARY OF THE INVENTION

The compounds of the present invention are of the formula

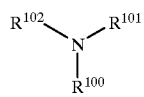
(I)

and the pharmaceutically acceptable acid addition salts thereof wherein $R^{100}$ is

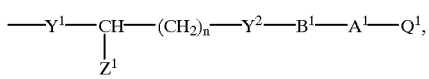

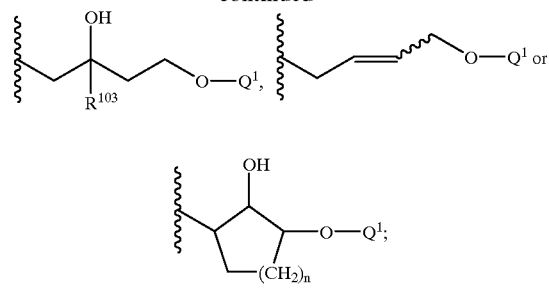

where $R^{103}$ is $-(C_1-C_4)$alkyl;

$Y^1$ is selected from the group consisting of oxygen, methylene, ethylene and a covalent bond;

$Z^1$ is selected from the group consisting of H, OH, $CF_3$, $NO_2$, and $-O(C_1-C_4)$alkyl;

n is 1 or 2;

$Y^2$ is selected from the group consisting of O, S, NH, $NCH_3$, a covalent bond,

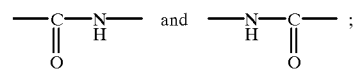

$B^1$ is selected from the group consisting of a covalent bond and optionally substituted phenyl,
where the optionally substituted phenyl is optionally substituted with one or two substituents independently selected from the group consisting of $(C_1-C_4)$alkyl, halo, $(C_1-C_4)$alkoxy, amino, N-alkylamino having 1 to 4 carbons, N,N-dialkylamino having a total of 2 to 4 carbons, nitrile and nitro;

$A^1$ is selected from the group consisting of a covalent bond, $(C_1-C_4)$alkylene, O, S and NH;

$Q^1$ is selected from the group consisting of

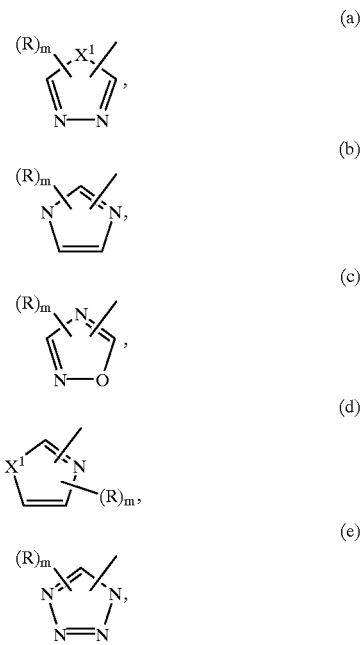

-continued

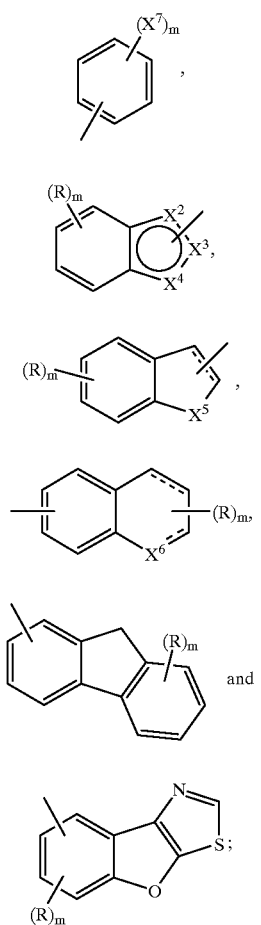

wherein - - - represents a single or a double bond;
X$^1$ is O or S;
X$^2$, X$^3$ and X$^4$ are each independently selected from the group consisting of C, N, CH, NH, O and S, provided that no more than one of X$^2$, X$^3$ and X$^4$ is O or S;
X$^5$ is selected from the group consisting of

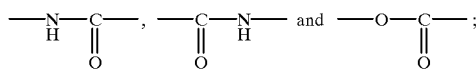

X$^6$ is selected from the group consisting of C, CH, N, NH,

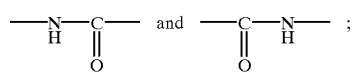

X$^7$ is selected from the group consisting of (C$_1$–C$_4$) alkyl, halo, (C$_1$–C$_4$)alkoxy, amino, nitrile, nitro, N-alkylamino having 1 to 4 carbons and N,N-dialkylamino having a total of 2 to 6 carbons;
m is 1, 2 or 3;
and each R is independently selected from the group consisting of hydrogen, (C$_1$–C$_4$)alkyl, (C$_1$–C$_4$) alkoxy, halo, N-alkylamino having 1 to 4 carbons, N,N-dialkylamino having a total of 2 to 6 carbons, amino, nitro, nitrile, hydroxyl, alkylthio having 1 to 3 carbons, =N—OCH$_3$, =N—OH, pyridinyl, (pyridin-1-yl)methylene, piperazinyl, 4-alkylpiperazinyl having 1 to 4 carbons in the alkyl portion, morpholino, —CH$_2$—C(OH)(CH$_3$)$_2$, allyl, —NHCOCH$_3$, aralkylamino having 1 to 4 carbons in the alkyl portion and optionally substituted phenyl, where the optionally substituted phenyl is optionally substituted with 1 or 2 substituents independently selected from the group consisting of (C$_1$–C$_4$)alkyl, halo, (C$_1$–C$_4$)alkoxy, amino, nitrile, nitro, N-alkylamino having 1 to 4 carbons and N,N-dialkylamino having a total of 2 to 6 carbons;

R$^{101}$ is the same as R$^{100}$ or is selected from the group consisting of hydrogen, (C$_1$–C$_4$)alkyl, alkenylphenyl having 2 to 4 carbons in the alkenyl portion, and alkylphenyl having 1 to 4 carbons in the alkyl portion and the phenyl portion is optionally substituted with one or two substituents independently selected from the group consisting of (C$_1$–C$_4$)alkyl, halo, (C$_1$–C$_4$)alkoxy, amino, nitrile, nitro, N-alkylamino having 1 to 4 carbons and N,N-dialkylamino having a total of 2 to 6 carbons;

R$^{102}$ is selected from the group consisting of hydrogen,

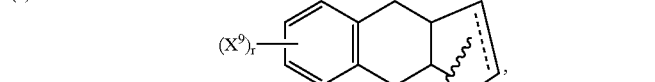

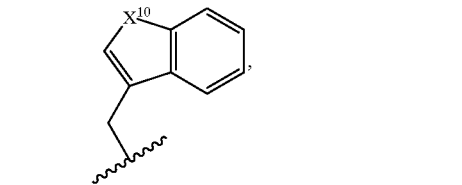

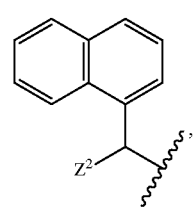

-continued
(q) 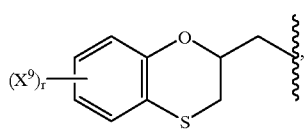
(r) 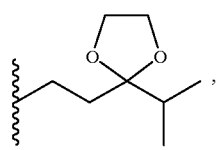
(s) 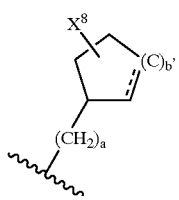
(t) 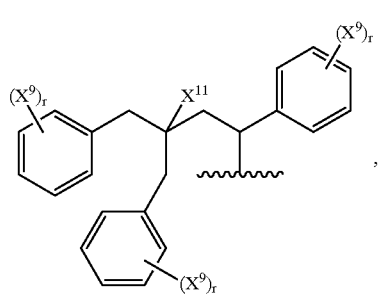
(u) 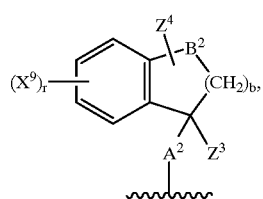
(v) 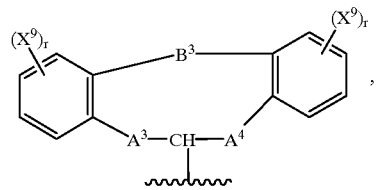
(w) 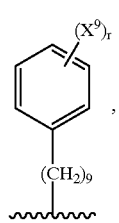
-continued
(x) 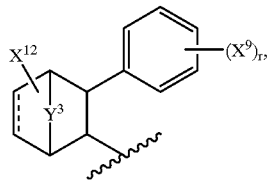
(y) 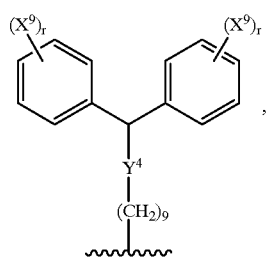
(z) 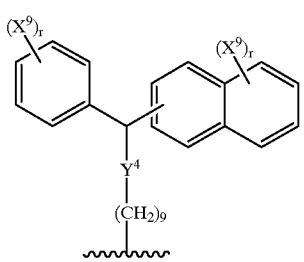
(za) 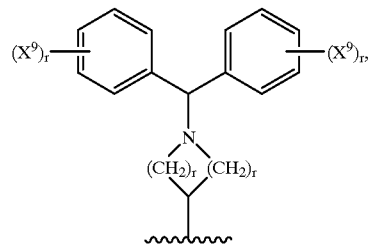
(zb) 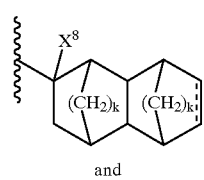
and
(zc) 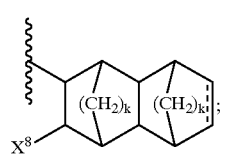
where r for each occurrence is independently 1 or 2;
a is 0, 1, 2 or 3;
$X^8$ is selected from the group consisting of $(C_1-C_4)$ alkyl and

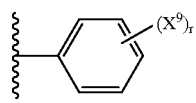

5 where r is as defined above;

$X^9$ for each occurrence is independently selected from the group consisting of hydrogen, hydroxy, chloro, fluoro, $(C_1-C_4)$alkoxy, $CF_3$ and $(C_1-C_4)$alkyl;

$X^{10}$ is S or O;

$X^{11}$ is hydrogen or hydroxy;

$Z^2$ is hydrogen or methyl;

b is 0, 1, 2 or 3;

$A^2$ is selected from the group consisting of a covalent bond, $CHCH_3$ and $(C_1-C_4)$alkylene;

$B^2$ is selected from the group consisting of $CH_2$, CH and S;

$Z^3$ is selected from the group consisting of hydrogen, phenyl and hydroxy;

$Z^4$ is selected from the group consisting of hydrogen, phenyl and $(C_1-C_4)$alkyl;

$B^3$ is selected from the group consisting of S, O, $-CH_2O-$, $-CH_2S-$, $-CH_2-$, $-CH_2-CH_2-$, $-CH=CH-$ and no bond;

$A^3$ and $A^4$ are independently a covalent bond or methylene;

$X^{12}$ is selected from the group consisting of hydrogen, $(C_1-C_4)$alkyl, phenyl and benzyl;

$Y^3$ is selected from the group consisting of $(C_1-C_4)$ alkylene, O, S, $-CH_2O-$ and $-CH_2S-$;

$Y^4$ is selected from the group consisting of S, O, NH and a covalent bond;

g is an integer from 1 to 4;

k for each occurence is independently 0, 1 or 2; and

- - - represents a single or a double bond;

or $R^{101}$ and $R^{102}$ are taken together with the nitrogen to which they are attached and form heterocycles selected from the group consisting of

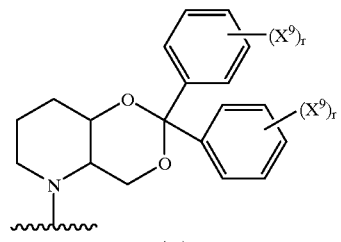

(aa)

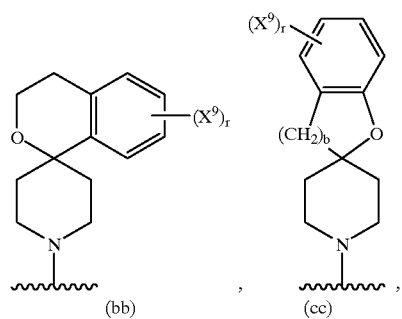

(bb), (cc),

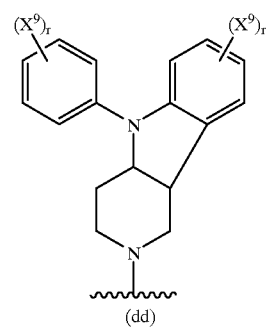

(dd),

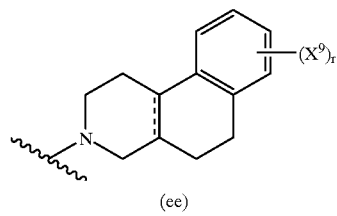

(ee),

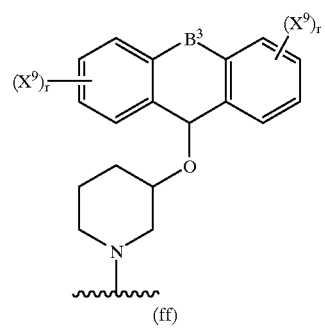

(ff),

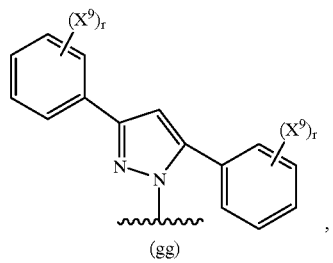

(gg),

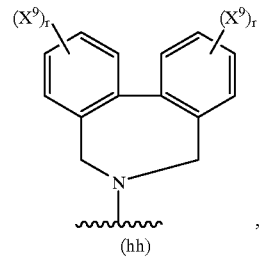

(hh),

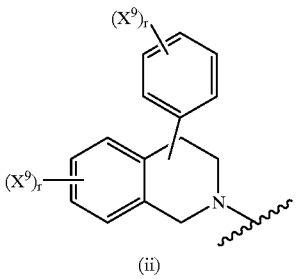

(ii),

-continued

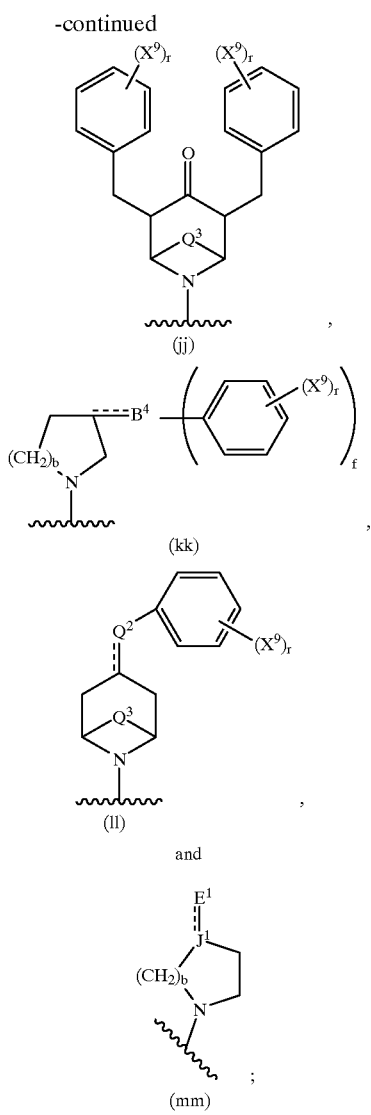

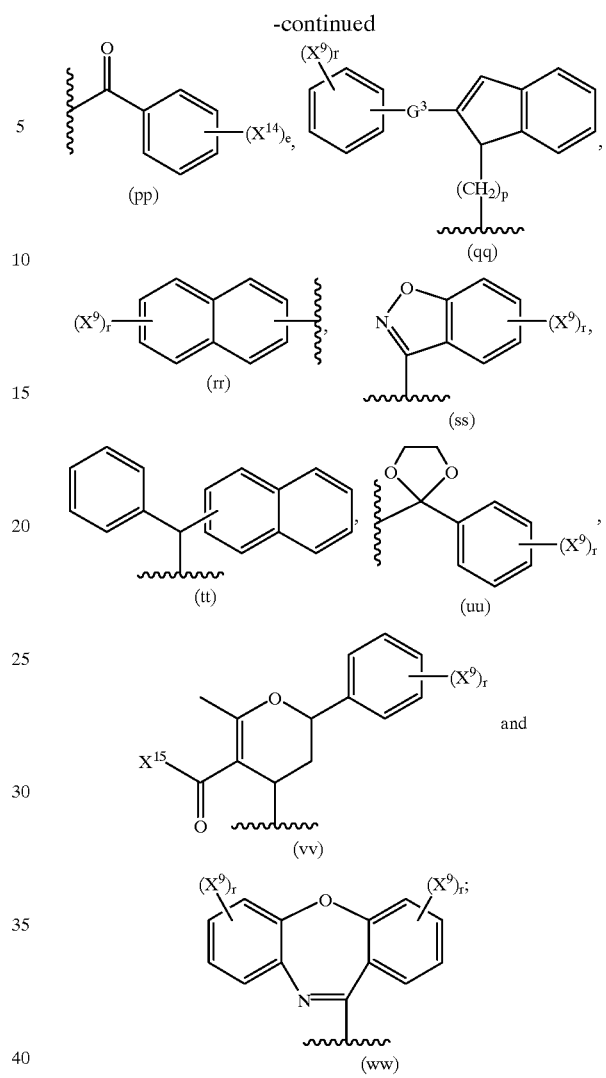

where $X^9$, b, $B^3$ and r are as defined above;
$Q^2$ is selected from the group consisting of S, O, $CH_2$ and CH;
$Q^3$ is $(C_1-C_4)$alkylene;
$B^4$ is selected from the group consisting of C, O, CH—CN, CH and $CH_2$;
f is 1 or 2;
$J^1$ is selected from the group consisting of C, CH, and N;
- - - represents a single or a double bond,
and $E^1$ is selected from the group consisting of alkylphenyl having 1 to 4 carbons,

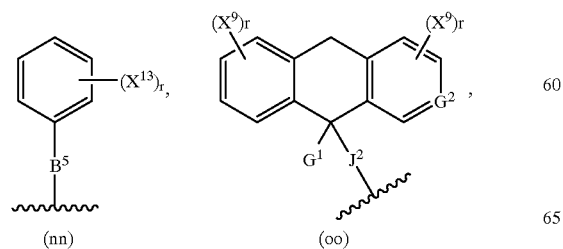

where $X^9$, $B^3$ and r are as defined above;
$B^5$ is O, S, a covalent bond, CH, C=O, or $(C_1-C_3)$ alkylene;
$X^{13}$ is selected from the group consisting of hydrogen, hydroxy, chloro, fluoro, $(C_1-C_4)$alkoxy, $CF_3$, $(C_1-C_4)$ alkyl and thioalkyl having 1 to 4 carbons;
$G^1$ is hydrogen, CN or hydroxy;
$G^2$ is N or CH;
$J^2$ is selected from the group consisting of C=O, a covalent bond and $(C_1-C_4)$alkylene;
$X^{14}$ is, for each occurence, independently $(C_1-C_4)$ alkyl;
e is 2, 3, 4 or 5;
$G^3$ is

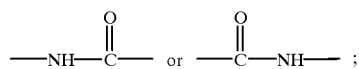

and p is 2 or 3;
provided that:
(1) when $Y^1$ is a covalent bond or when n is 0, $Z^1$ cannot be hydroxy, $NO_2$, —$S(C_1-C_4)$alkyl or -$O(C_1-C_4)$alkyl;
(2) $B^1$ and $A^1$ cannot each be a covalent bond;

(3) when $B^1$ is an optionally substituted phenyl, $Q^1$ is selected from the group consisting of structures (a), (b), (c), (d), (e), (f), and (g);

(4) $R^{101}$ and $R^{102}$ cannot both be hydrogen at the same time;

(5) when $B^1$ is a covalent bond and $Y^2$ is O, S, NH or

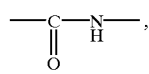, $A^1$ is not O, S or NH;

(6) when $Q^1$ is

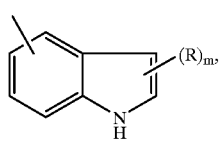

$R^{101}$ and $R^{102}$ taken together with the nitrogen to which they are attached cannot be

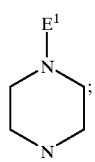;

(7) when $Q^1$ is

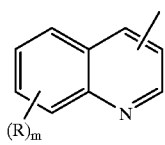

and $R^{102}$ is hydrogen, $R^{101}$ cannot be alkylphenyl having 1 to 4 carbons in the alkyl portion and optionally substituted at the phenyl portion;

(8) when $Q^1$ is

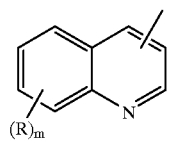

and $R^{101}$ is hydrogen, $R^{102}$ cannot be (v), (w) or (y);

(9) when $Q^1$ is

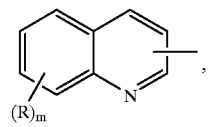, $R^{101}$ and $R^{102}$ taken together with the nitrogen to which they are attached cannot be

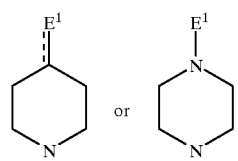

wherein $E^1$ is (nn) or (oo);

(10) when the compound of formula (I) is

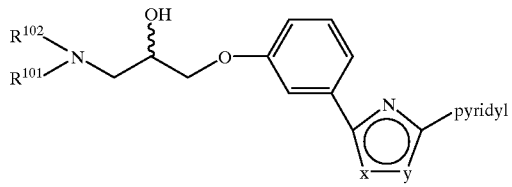

wherein X is N and Y is O or X is O and Y is N then $R^{101}$ and $R^{102}$ taken separately or together with the nitrogen to which they are attached cannot be the following:

| | $R^{101}$ | $R^{102}$ | $R^{101}$ and $R^{102}$ taken together with the N to which they are attached |
|---|---|---|---|
| a | — | — | 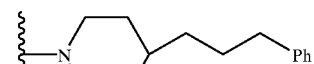 |
| b | — | — | 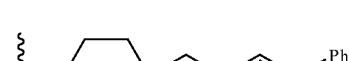 |
| c | H |  | — |

-continued

| | $R^{101}$ | $R^{102}$ | $R^{101}$ and $R^{102}$ taken together with the N to which they are attached |
|---|---|---|---|
| d | H | (2-methoxyphenyl)(4-trifluoromethylbenzyl)methyl group | — |
| e | H | 10,11-dihydrodibenzo[b,f]thiepin-10-yl | — |
| f | H | 1-phenylindan-1-yl-methyl | — |
| g | H | 1,2,3,4-tetrahydronaphthalen-1-yl-methyl | — |
| h | n-butyl | (7-methoxy-2,3-dihydro-1,4-benzoxathiin-2-yl)methyl | — |

(11) when the compound of formula (I) is

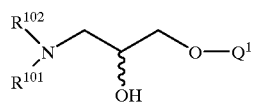

wherein $Q^1$ is quinolin-5-yl or 2-methylbenzthiazol-7-yl, then $R^{101}$ and $R^{102}$ taken separately or together with the nitrogen to which they are attached cannot be the following:

| | $R^{101}$ | $R^{102}$ | $R^{101}$ and $R^{102}$ taken together with the N to which they are attached |
|---|---|---|---|
| a | — | — | 4-(naphthalen-1-yl)piperazin-1-yl |

-continued
| | $R^{101}$ | $R^{102}$ | $R^{101}$ and $R^{102}$ taken together with the N to which they are attached |
|---|---|---|---|
| b | — | — | 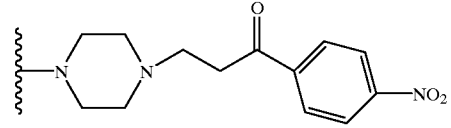 |
| c | — | — | 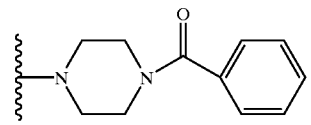 |
| d | — | — | 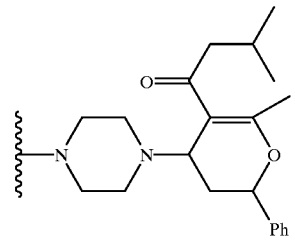 |
| e | H | 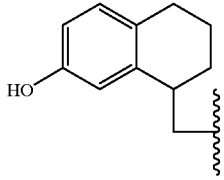 | — |
| f | H | 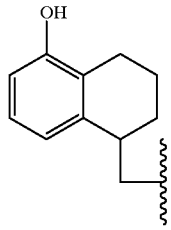 | — |
| g | H | 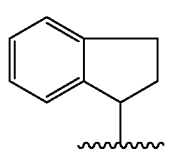 | — |
| h | 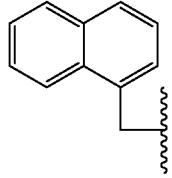 | 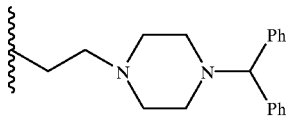 | — |
| i | H |  | — |

-continued

| | $R^{101}$ | $R^{102}$ | $R^{101}$ and $R^{102}$ taken together with the N to which they are attached |
|---|---|---|---|
| j | H | 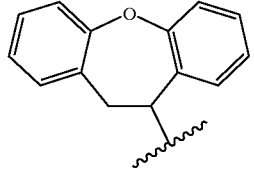 | — |
| k | H | 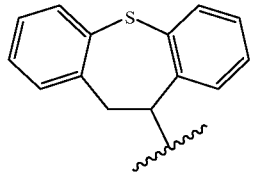 | — |
| l | H | 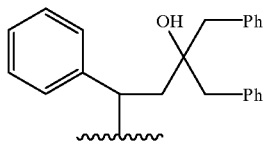 | — |
| m | — | — | 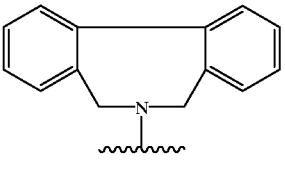 |

(12) when $R^{102}$ is (u), and $A^2$ is a covalent bond, $Z^3$ cannot be hydroxy;

(13) when $R^{101}$ and $R^{102}$ are taken together with the nitrogen to which they are attached and forms (mm) and b is 1, $J^1$ cannot be nitrogen;

(14) the compound of the formula (I) is not methyl-[3-(2-methyl-benzothiazol-7-yloxy)-propyl]-naphthalen-1-ylmethyl-amine;

(15) the compound of the formula (I) is not 1-(4-diethylamino-2-methyl-benzothiazol-7-yloxy)-3-[4-(10,11-dihydro-5H-dibenzo[a,d]cyclohepten-5-yl)-piperazin-1-yl]-propan-2-ol;

(16) the compound of the formula (I) is not 1-(6-allyl-2-methyl-benzothiazol-7-yloxy)-3-[4-(10,11-dihydro-5H-dibenzo[a,d]cyclohepten-5-yl)-piperazin-1-yl]-propan-2-ol; and

(17) the compound of the formula (I) is not 1-[4-(10,11-dihydro-5H-dibenzo[a,d]cyclohepten-5-yl)-piperazin-1-yl]-3-(6-methoxy-2-phenyl-benzothiazol-7-yloxy)-propan-2-ol.

It will be apparent to one skilled in the art that when $Q^1$ is (g), (h), (i), (j) or (k), $Q^1$ can be bonded to $A^1$ at any chemically available site on the molecule, and R can be bonded to any available site on the molecule.

For the partial structures

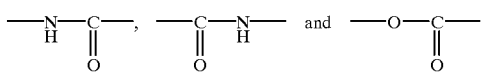

it is understood that they are inserted into the molecules in the specific orientation as drawn.

A preferred group of compounds is that group of compounds of formula I, above, wherein $B^1$ is an optionally substituted phenyl; $Y^2$ is attached to $B^1$ in an ortho or meta position relative to $A^1$-$Q^1$; $A^1$ is a covalent bond, O, S or —$CH_2$—; $Q^1$ is (a), (b), (c) or (d) wherein R, m and $X^1$ are as defined above; $Y^1$ is —$CH_2$—; $Z^1$ is hydrogen or hydroxy; n is 1 or 2; and $Y^2$ is O, NH, $NCH_3$ or S.

Another group of preferred compounds is that group of compounds of formula I, above, wherein $B^1$ is a covalent bond; $Y^1$ is O and $Z^1$ is hydrogen; or $Y^1$ is —$CH_2$— and $Z^1$ is hydrogen or hydroxy; n is 1 or 2; $Y^2$ is O, NH, NMe or S; and $Q^1$ is (g) wherein $X^2$ is N, $X^3$ is CR or N, and $X^4$ is S or O; or $X^2$ is N, $X^3$ is S or NR, and $X^4$ is N; or $X^2$ is N, $X^3$ is N or CR and $X^4$ is NH or NMe.

A more preferred group of compounds is that group of compounds of formula I, above, wherein $B^1$ is an optionally substituted phenyl; $Y^2$ is attached to $B^1$ in the meta position relative to $A^1$-$Q^1$; $A^1$ is a covalent bond, O, S or —$CH_2$—; $Q^1$ is (c) wherein m is 1 and R is pyridin-3-yl or pyridin-4-yl; and $R^{101}$ and $R^{102}$ are taken together with the nitrogen to which they are attached and form

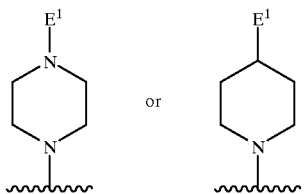

wherein $E^1$ is (nn), (oo), (pp), or (qq) wherein $X^{13}$, $B^5$, r, $X^9$, $B^3$, $G^1$, $G^2$, $J^2$, $X^{14}$, e, p, and $G^3$ are as defined above.

Another group of more preferred compounds is that group of compounds of formula I, above, wherein $B^1$ is an optionally substituted phenyl; $Y^2$ is attached to $B^1$ in the meta position relative to $A^1$-$Q^1$; n is 1; $Y^2$ is O; $Z^1$ is OH; $A^1$ is a covalent bond, O, S or —CH$_2$—; $Q^1$ is (c) wherein m is 1 and R is pyridin-3-yl or pyridin-4-yl; $R^{101}$ is hydrogen, alkenylphenyl having 2 to 4 carbons in the alkenyl portion or alkylphenyl having 1 to 4 carbons as defined above; and $R^{102}$ is (p), (s), (u), (v) or (w) wherein $X^8$, a, b, $X^9$, $A^3$, $A^4$, $B^3$, $Z^2$, r, $Z^4$, $B^2$, $A^2$, $Z^3$ and g are as defined above.

Yet another group of more preferred compounds is that group of compounds of formula I, above, wherein $B^1$ is a covalent bond; $Y^1$ is —CH$_2$—; $Z^1$ is OH; n is 1; $Y^2$ is O; $Q^1$ is (g) wherein $X^2$ is N, $X^3$ is CR or N, and $X^4$ is S or O; or $X^2$ is N, $X^3$ is S or NR, and $X^4$ is N; or $X^2$ is N, $X^3$ is N or CR and $X^4$ is NH or NMe; and $R^{101}$ and $R^{102}$ are taken together with the nitrogen to which they are attached and is (bb), (ee), (ff),

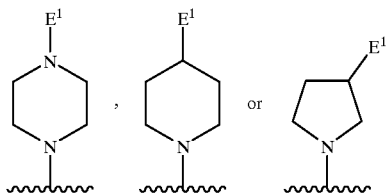

wherein $E^1$ is (nn), (oo), (pp) or (qq) wherein $X^{13}$, $B^5$, r, $X^9$, $B^3$, $G^1$, $G^2$, $J^2$, $X^{14}$, e, p and $G^3$ are as defined above; or $R^{101}$ is as defined above for formula I and $R^{102}$ is (l), (n), (o), (p), (s), (u), or (x) wherein $X^9$, r, $X^{11}$, $Z^2$, $X^8$, a, b, $Z^3$, $Z^4$, $B^2$, $A^2$, $X^{12}$ and $Y^3$ are as defined above.

Particularly preferred compounds of this invention are:
1-[4-(10,11-dihydro-5H-dibenzo[a,d]cyclohepten-5-yl)-piperazin-1-yl]-3-(3-methyl-3H-benzoimidazol-4-yloxy)-propan-2-ol,
1-[4-(10,11-dihydro-5H-dibenzo[a,d]cyclohepten-5-yl)-piperazin-1-yl]-3-(3-methyl-3H-benzotriazol-4-yloxy)-propan-2-ol,
1-(benzothiazol-7-yloxy)-3-[4-(10,11-di hydro-5H-dibenzo[a,d]cyclohepten-5-yl)-piperazin-1-yl]-propan-2-ol,
1-[4-(10,11-dihydro-5H-dibenzo[a,d]cyclohepten-5-yl)-piperazin-1-yl]-3-(2-methyl-benzothiazol-7-yloxy)-propan-2-ol,
1-(4-benzhydryl-piperidin-1-yl)-3-(2-methyl-benzothiazol-7-yloxy)-propan-2-ol,
1-[4-(10,11-dihydro-5H-dibenzo[a,d]cyclohepten-5-yl)-piperazin-1-yl]-3-(2-dimethylamino-benzothiazol-7-yloxy)-propan-2-ol,
7-{3-[4-(10,11-dihydro-5H-dibenzo[a,d]cyclohepten-5-yl)-piperazin-1-yl]-2-hydroxypropoxy}-benzothiazole-2-carboxylic acid amide,
1-[4-(10,11-dihydro-5H-dibenzo[a,d]cyclohepten-5-yl)-piperazin-1-yl]-3-(2-pyridin-3-yl-benzothiazol-7-yloxy)-propan-2-ol,
1-(4-benzhydryl-piperidin-1-yl)-3-(2-pyridin-2-yl-benzothiazol-7-yloxy)-propan-2-ol,
1-(2-methyl-benzothiazol-7-yloxy)-3-[4-(2-propysulfanyl-phenyl)-piperazin-1-yl]-propan-2-ol,
N-[1-(3-{4-[2-hydroxy-3-(2-methyl-benzothiazol-7-yloxy)-propyl]-piperazin-1-yl}-propyl)-1H-benzoimidazol-2-yl] 4-methoxy-benzamide,
1-(5-chloro-tricyclo[7.3.1.0,2,7]trideca-2,4,6,10-tetraen-13-ylamino)-3-(2-methyl-benzothiazol-7-yloxy)-propan-2-ol,
3-[2-hydroxy-3-(2-methyl-benzothiazol-7-yloxy)-propylamino]-2-phenyl-decahydronaphthalen-2-ol,
1-(4-benzhydryl-piperazin-1-yl)-3-[3-(5-pyridin-3-yl-[1,2,4]oxadiazol-3-yl)-phenoxy]-propan-2-ol,
1-(4-benzhydryl-piperidin-1-yl)-3-[3-(5-pyridin-3-yl-[1,2,4]oxadiazol-3-yl)-phenoxy]-propan-2-ol,
1-(4-benzhydryl-piperidin-1-yl)-3-[3-(5-pyridin-4-yl-[1,2,4]oxadiazol-3-yl)-phenoxy]-propan-2-ol,
1-(4-benzhydryl-piperidin-1-yl)-3-[3-(3-pyridin-3-yl-[1,2,4]oxadiazol-5-yl)-phenoxy]-propan-2-ol,
1-(methyl-naphthalen-1-ylmethyl-amino)-3-[3-(3-pyridin-3-yl-[1,2,4]oxadiazol-5-yl)-phenoxy]-propan-2-ol, and the pharmaceutically acceptable salts thereof.

A more particularly preferred group of compounds of this invention is:
1-[4-(2-chloro-dibenzo[b,f][1,4]oxazepin-11-yl)-piperazin-1-yl]-3-(2-methyl-benzothiazol-7-yloxy)-propan-2-ol,
1-[4-(10,11-dihydro-5H-dibenzo[a,d]cyclohepten-5-yl)-piperazin-1-yl]-3-(2-methyl-benzothiazol-7-yloxy)-propan-2-ol,
1-[4-(10,11-dihydro-5H-dibenzo[a,d]cyclohepten-5yl)-piperazin-1-yl]-3(2-dimethylamino-benzothiazol-7-yloxy)-propan-2-ol,
7-{3-[4-(10,11-dihydro-5H-dibenzo(a,d)cyclohepten-5-yl)-piperazin-1-yl]-2-hydroxy-propoxy}-benzothiazole-2-carboxylic acid amide,
1-{4-[2-hydroxy-3-(2-methyl-benzothiazol-7-yloxy)-propyl]-piperazin-1-yl}-2,2-diphenylethanone,
1-[4-(10,11-dihydro-5H-dibenzo[a,d]cyclohepten-5-yl)-piperazin-1-yl]-3-(2-pyridin-4-yl-benzothiazol-7-yloxy)-propan-2-ol,
1-[4-(10,11-dihydro-5H-dibenzo[a,d]cyclohepten-5-yl)-piperazin-1-yl]-3-(2-isopropyl-benzothiazol-7-yloxy)-propan-2-ol,
1-(2-butyl-benzothiazol-7-yloxy)-3-(1-phenyl-cyclohexylamino)-propan-2-ol,
1-(2-butyl-benzothiazol-7-yloxy)-3-[1-(4-chloro-phenyl)-cyclohexylamino]-propan-2-ol,
1-(4-benzhydryl-piperidin-1-yl)-3-[3-(5-pyridin-3-yl-[1,2,4]oxadiazol-3-yl)-phenoxy]-propan-2-ol,
1-[4-(10,11-dihydro-5H-dibenzo[a,d]cyclohepten-5-yl)-piperazin-1-yl]-3-(3-methyl-3H-benzoimidazol-4-yloxy)-propan-2-ol,
1-(4-benzhydryl-piperidin-1-yl)-3-(2-methyl-benzothiazol-7-yloxy)-propan-2-ol,
3-[2-hydroxy-3-(2-methyl-benzothiazol-7-yloxy)-propylamino]-2-phenyl-decahydronaphthalen-2-ol and the pharmaceutically acceptable salts thereof.

The present invention also includes a method of inhibiting a P-glycoprotein in a mammal in need of such treatment which comprises administering to said mammal a P-glycoprotein inhibiting amount of a compound of formula I. Preferred is the method where the mammal is a human suffering from cancer and said compound is administered before, with or after the administration to said human of an anticancer effective amount of a chemotherapeutic agent.

Also included is a pharmaceutical composition for administration to a mammal which comprises a P-glycoprotein inhibiting amount of a compound of formula I, a pharmaceutically acceptable carrier or diluent and, optionally, an anticancer effective amount of a chemotherapeutic agent.

As previously described, the compounds of formula I form pharmaceutically acceptable acid addition salts. Said pharmaceutically acceptable acid addition salts include, but are not limited to, those formed with HCl, HBr, $HNO_3$, $H_2SO_4$, $H_3PO_4$, $CH_3SO_3H$, $C_6H_5SO_3H$, $CH_3CO_2H$, gluconic acid, lactic acid, 2-hydroxyethanesulfonic acid, camphorsulfonic acid, tartaric acid, maleic acid and succinic acid. In the case of those compounds of the formula I which contain a further basic nitrogens, it will, of course, be possible to form higher acid addition salts (e.,g., the dihydrochloride) as well as the usual monoacid addition salt.

As one skilled in the art will recognize based upon the disclosure herein, compounds of formula I have the potential for containing asymmetric carbon atoms. All isomers of the compounds of formula I and the salts thereof are considered within the scope of the present invention.

DETAILED DESCRIPTION

The compounds of the invention can be prepared by a number of different processes according to the invention. The following methods describe the synthetic procedures which are employed to make the compounds of this invention.

METHOD A

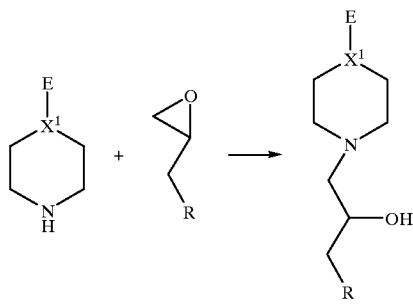

(Oxiran-2-yl-methoxy)aromatic (1.0 equivalent (eq.)) in ethanol (EtOH), 2-propanol, EtOH/DMF or $H_2O$/dioxane (1:4) and the required amine (1.0–2.0 eq as free base) are mixed and heated to reflux (or in sealed tube at about 80–100° C.) for several hours under $N_2(g)$ until all of the epoxide has been consumed. The mixture is poured into $H_2O$ and extracted with ethyl acetate (EtOAc)/diethylether ($Et_2O$) (1:1 to 0:1). The organic phase is dried over $MgSO_4$ or $Na_2SO_4$, filtered and concentrated in vacuo. The residue is chromatographed on silica to yield the free base which is converted to a mono- or di-hydrochloride salt by treatment with the appropriate amount of 1.0M HCl in $Et_2O$ or $CHCl_3/Et_2O$ followed by either filtration of the precipitated salt and recrystallization or by concentration in vacuo and recrystallization of the residue.

METHOD B

Reactions of glycidyl ethers with amine salts are carried out as described in Method A but with the addition of 1.0–2.5 eq. of diisopropylethylamine to the reaction mixture.

METHODS $C_A$, $C_B$ and $C_C$

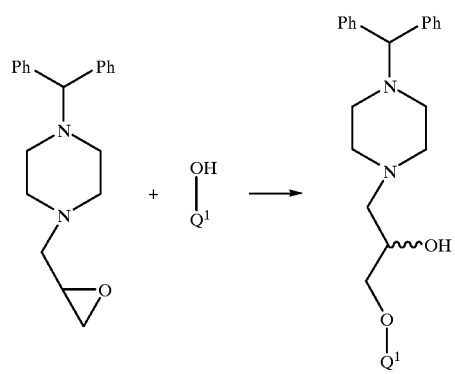

METHOD $C_A$

To a solution of a glycidylamine (specifically, 1-benzhydryl-4-oxiran-2-ylmethyl-piperazine; 1.0–2.0 mol eq.) and phenol (1.0 mol eq.) in 2-propanol or n-butanol is added aqueous KOH or NaOH (1.0 mol eq. of 1–6N). The stirred mixture is refluxed under $N_2(g)$ atmosphere for 5–48 hours. The reaction is concentrated in vacuo and the residue is flash chromatographed on silica (EtOAc/hexanes or acetone/hexanes) to afford the product as the free base.

METHOD $C_B$

The method of $C_A$, above, is employed except (1.0 mol eq.) $K_2CO_3$(s) is utilized in refluxing n-BuOH (5–16 hours) rather than aqueous KOH or NaOH.

METHOD $C_C$

To phenol (1 mmol) in anhydrous DMF (1.5 mL) is added a catalytic amount of NaH (0.1–0.2 eq.). After evolution of $H_2(g)$ has ceased, the glycidylamine (1 mmol) is added and the mixture is stirred at about 50° C. for 24–72 hours under $N_2(g)$. The reaction mixture is poured into $H_2O$, the pH adjusted to 12–14 with 1N NaOH, and the product is extracted into 1:1 EtOAc/$Et_2O$. The organic extracts are combined, dried over $Na_2SO_4$, concentrated in vacuo and flash chromatographed to obtain the product as its free base.

METHOD D

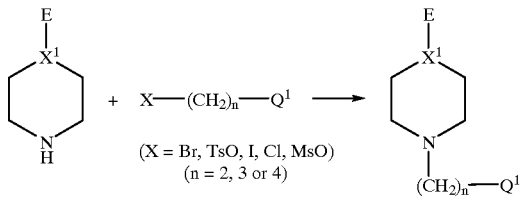

To a haloalkyl aryl ether (1.0 eq.) in t-BuOH is added the appropriate amine (1–5 eq.). The mixture is stirred at about 40–80° C. for about 2–36 hours until most of the aryl ether is consumed. Solvent is removed in vacuo and the residue is chromatographed on silica to obtain the product as its free base.

METHODS E$_A$, E$_B$, E$_C$

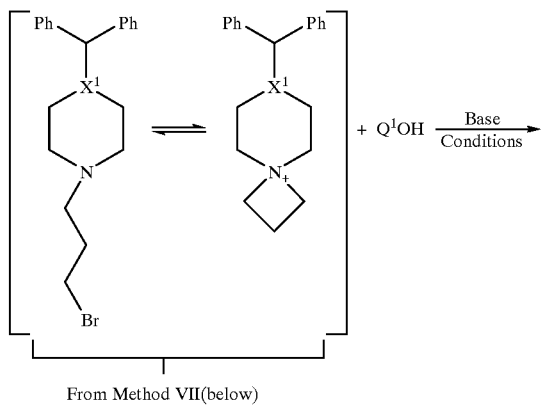

From Method VII(below)

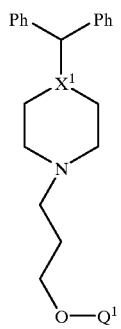

METHOD E$_A$

A hydroxyaromatic (1.0 eq.) is dissolved in dry DMF (2.8 mL) and Me$_4$N$^+$OH$^-$.5H$_2$O (0.95 eq.) is added with stirring under N$_2$(g). If an acid salt of the hydroxyaromatic is employed, 1.95 eq. of base are used. To the resulting solution of the phenolate is added the appropriate bromoalkylamine intermediate (0.5–1.0 eq.) and the mixture is stirred at about 40–100° C. (typically 50–90° C.) for about 2–48 hours until no further product formation (by HPLC detection methods) is evident. The mixture is partitioned between 1N NaOH and 1:1 EtOAc/Et$_2$O. The organic phase is washed with 1N NaOH (2x) and brine, dried over Na$_2$SO$_4$ and concentrated in vacuo. The residue is chromatographed on silica (acetone/hexanes or MeOH/CH$_2$Cl$_2$) to afford the product as its free base.

METHOD E$_B$

Method E$_A$ above is employed but NaH is utilized in formation of the phenolate solution in DMF, often with subsequent addition of KI or n-Bu$_4$N$^+$I$^-$ as nucleophilic catalysts.

METHOD E$_C$

A hydroxyaromatic (1.25 mmol), n-Bu$_4$N$^+$I$^-$ (1.0 mmol, 369 mg) and an ω-bromoalkylamine intermediate (1.0 mmol) in CHCl$_3$ or CH$_2$Cl$_2$ (2–10 mL) are mixed and stirred vigorously with aqueous NaOH (0.5–4N; ≧5 eq.) at about 20° C. under N$_2$(g) for about 5–72 hours. Following addition of more solvent (≈25 mL), the organic phase is separated, washed with 0.5N NaOH and brine, concentrated in vacuo, and chromatographed on silica to recover the product as its free base.

METHOD F

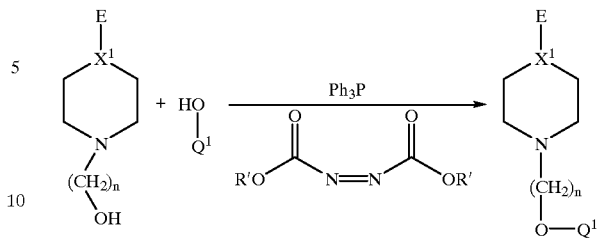

To a partial suspension or solution of Ph$_3$P (1.2 eq.) and a hydroxyaromatic (1.0 eq.) in dry THF (7.0 mL) at about 0° C. is added diethylazodicarboxylate (1.2 eq.) dropwise over several minutes. After 5 minutes at about 0° C. a suspension of an amino alcohol [typically 1-benzhydryl-4-(3-hydroxypropyl)piperazine (1.0 eq.) in dry THF (5.0 mL+2.0 mL rinse)] is added dropwise over 5 minutes to the solution. The reaction mixture is stirred for about 30 minutes at about 0° C. and for about 16 hours at about 20° C., and then concentrated in vacuo. Products are isolated as their free base by chromatography on silica, or as their crude HCl salts by precipitation from EtOAc/Et$_2$O solution upon addition of 1M HCl in Et$_2$O (2.2 mL, 2.2 mmol) and cooling to about 4° C. When necessary crude, HCl salts are purified by recrystallization (e.g., from CHCl$_3$) or by free-basing, washing the organic phase with 1N NaOH and brine, and reprecipiting the HCl salt from the organic extracts.

METHOD G$_A$

To the desired primary or secondary amine (1.0 mmol as its free base) in 20% H$_2$O/80% dioxane or THF (5mL) with 1–3 equivalents of Amberlite IRA400® resin ($^-$OH form; 0.43–1.30 g of ≈2.3 meq/g, previously washed with MeOH and dried in vacuo) is added the appropriate (oxiran-2-yl-methoxy-heteroaromatic derivative, 0.6–1.0 mmol). The mixture is heated to about 50–85° C. for about 4–60 hours under N$_2$(g) until no detectable epoxide remains (by TLC or analytical RP-HPLC). The resin is removed by filtration and the filtrate is concentrated in vacuo, redissolved in a small volume of 80% CH$_3$CN/2.0M pH 4.5 NH$_4$OAc buffer (2.5 mL) and purified by preparative reversed-phase HPLC (typically by injection onto a Dynamax-60A C18 column (21.4 mm×25 cm; 8 μm packing) previously equilibrated in 15% CH$_3$CN/85% pH 4.5, 50 mM NH$_4$OAc followed by elution (20–25 mL/min) with a 1% CH$_3$CN/min. gradient). Products are recovered by lyophilization or concentration in vacuo at about 35–40° C. and the residue is partitioned between saturated aqueous Na$_2$CO$_3$ and CHCl$_3$ or EtOAc. Organic fractions are dried over Na$_2$SO$_4$ (s) and concentrated in vacuo to afford the product as its free base. Conversion to the HCl salts typically involve dissolution of this residue in minimal CHCl$_3$, EtOAc or Et$_2$O, titration with the appropriate amount of 1M HCl in Et$_2$O (1–3 eq.), further dilution with Et$_2$O and cooling. Precipitated hydrochloride salts are filtered, washed with Et$_2$O and petroleum ether and dried in vacuo.

METHOD G$_B$

This method is conducted in essentially the same manner as described for Method G$_A$. However, amine salts (hydrochlorides, toluenesulfonates, maleates, etc.) are employed along with the appropriate number of neutralizing equivalents of aqueous NaOH in addition to the usual 1–3 equivalents of Amberlite IRA400® resin ($^-$OH form).

METHOD H

A suspension of NaH (60% oil dispersion, 1 eq) and the appropriate hydroxy compound (1 eq.) are mixed in a solvent such as tetrahydrofuran (THF) and warmed to about 50° C. for about 30 minutes. A bromoalkylamine is added to the mixture and stirred at about 50° C. for about 3 hours. The solvent is evaporated and the crude product is purified by silica gel chromatography to yield the desired product.

The following is the preferred method of forming the salt of a compound of formula I. For monohydrochlorides, the purified free base was dissolved at about 20° C. in a minimum volume of $CHCl_3$ or EtOAc (or $Et_2O$ if sufficiently soluble) and diluted with dry $Et_2O$, usually to the point where further addition would cause permanent cloudiness. A solution of 1.0M HCl in dry $Et_2O$ (1.05 eq) is added dropwise with stirring causing precipitation of the monohydrochloride salt which is recovered, after cooling to about 0° C., by centrifugation or filtration, washed with $Et_2O$ and pet. ether and dried in vacuo to constant mass. For di- and trihydrochloride salts, the free base was dissolved in minimal alcohol (MeOH or EtOH) or acetonitrile and the solution was treated dropwise while stirring with the appropriate volume of 1.0M HCl in $Et_2O$ (ideally maintaining most material in solution until the addition of the final equivalent of acid has begun by additions of alcohol or $CH_3CN$ as required). When the addition is complete, the salt may be precipitated by dilution with dry $Et_2O$ and cooling, or by concentration in vacuo and either trituration with $Et_2O$ or recrystallization from alcohol/$Et_2O$ or $CH_3CN/Et_2O$. Precipitated salts are recovered by centrifugation or filtration, and washed with $Et_2O$ and pet. ether and dried in vacuo to constant mass.

The following procedures are utilized to synthesize the starting materials for the compounds of this invention.

METHOD I

PREPARATION of Glycidyl Ethers (Oxiranyl-2-Methoxy-aromatics)

NaH (1.1 eq.) is added to a solution of the appropriate phenol (1.0 eq., 1M) in anhydrous DMF. The mixture is stirred at about 40° C. under $N_2(g)$ until the evolution of $H_2(g)$ ceases. Epibromohydrin (1.10 eq.) is added and the mixture is stirred at about 60° C. for about 0.5 to 16 hours until the reaction is complete by TLC/HPLC. The mixture is poured onto ice/$H_2O$ and extracted with $Et_2O$ or 1:1 EtOAc/$Et_2O$. Organic extracts are pooled, washed with $H_2O$ and saturated NaCl(aq), dried over $Na_2SO_4$(s) and concentrated in vacuo. The product could be purified by chromatography on silica gel or utilized directly in reactions with amines.

METHOD II (2R)- and (2S)-glycidyl ethers are prepared from the corresponding (2R)- and (2S)-glycidyl-3-nitrobenzenesulfonates at about 30–45° C. (or p-toluenesulfonates at about 40–60° C.), respectively, instead of epibromohydrin, according to the procedure of Method I, above.

METHOD III

Alternate Preparation of Glycidyl Amines

To a solution of a secondary amine, typically 1-benzhydrylpiperazine (10.0 g, 39.6 mmol), in dioxane (80–110 mL) is added a tertiary amine (39.6 mmol; e.g., diisopropyl ethyl amine or N-methyl morpholine) followed by epibromohydrin (119 mmol, 16.3 g). The mixture is stirred at about 22° C. for about 16 hours, and precipitated salts are removed by filtration. The filtrate is concentrated in vacuo, redissolved in EtOAc (150 mL), washed with 1.0N NaOH (2×50 mL) and brine (50 mL), dried over $Na_2SO_4$(s) and then flash chromatographed on silica (40% acetone/hexanes) to afford pure glycidyl amine.

METHOD IV

PREPARATION of Haloalkyl Aryl Ethers

To the appropriate hydroxyaromatic (20 mmol) in anhydrous DMF or THF (45 mL) is added NaH (20 mmol, 1.0 eq.). After evolution of $H_2(g)$ ceases and all of the NaH(s) has dissolved (with gentle warming if required) an excess (100–200 mmol, 5–10 eq.) of 1,2-dibromoethane (for n=2), 1,3-dibromopropane (n=3), 1,4-dibromobutane (n=4), alkylchlorides, alkyliodides, tosylates or triflates is added. Stirring under $N_2(g)$ is continued at about 20–60° C. for about 2–24 hours until almost all of the phenol is consumed. The mixture is poured into 5% aq. $Na_2CO_3$ and extracted ($CHCl_3$, EtOAc or $Et_2O$). The pooled organic extracts are washed with 10% $Na_2CO_3$ and brine, dried over $Na_2SO_4$(s), concentrated in vacuo and the product isolated by chromatography on silica (acetone/hexanes or EtOAc/hexanes). When the aryl moiety is sufficiently basic (pKa 2.5–8) the ether product can often be isolated by precipitation of its HCl salt from $Et_2O$ or EtOAc.

METHOD V

Method, IV, above, is employed but (1 eq.) tetraalkylammonium hydroxide salt (typically $Me_4N^+OH^-.5H_2O$) is used as a base instead of NaH.

METHOD VI

To a stirred slurry of the appropriate hydroxyaromatic (10 mmol) and $Ph_3P$ (12 mmol, 1.2 eq.) at about −20° C. to 0° C. in anhydrous THF (20 mL) is added diethyl azodicarboxylate (12 mmol, 1.2 eq.) dropwise, immediately followed by 2-bromoethanol (for n=2) or 3-bromopropanol (n=3) (12 mmol, 1.2 eq.) dropwise. The stirred mixture is allowed to warm to about 20° C. for about 16 hours. Solvent is removed in vacuo and the residue is chromatographed on silica (EtOAc/hexanes or acetone/hexanes) to afford the bromoalkylether (typically 70–98% yield).

METHOD VII

PREPARATION of 1-Benzhydryl-4-(3-bromopropyl)piperazine 1,3-Dibromopropane (5 eq., 199 mmol, 20.3 mL) is added to a stirred solution of 1-benzylhydrylpiperazine (10.1 g, 40 mmol) under one of the sets of reaction conditions listed below. The mixture is stirred until thin layer chromatography TLC (35% acetone/hexanes) indicates detectable amounts of slower moving 1,3-bis(1-benzyhydrylpiperazinyl)propane dialklylation by-product have been produced in addition to the initial desired product. The reaction mixture is partitioned between $CH_2Cl_2$ or $CHCl_3$ and saturated aqueous $NaHCO_3$. The organic phase is washed with saturated $NaHCO_3$, dried over $Na_2SO_4$(s) and concentrated in vacuo to a yellow oil which is immediately flash chromatographed on silica in 15% acetone/hexanes. When necessary, recovered product is triturated with heptanes to remove residual dibromopropane and yield the product as a white solid consisting of a dynamic mixture of the desired bromopropyl derivative and its corresponding cyclized azetidinium bromide salt.

Reaction Conditions:
A. Dioxane (50–80 mL), room temperature, ≈3 hours.
B. 80% Dioxane or i-PrOH (50–80 mL)/20% $H_2O$, 2 eq. $Na_2CO_3$, room temperature, ≈5 hours.
C. $CH_2Cl_2$ (100 mL), 1.1 eq., $K_2CO_3$(s), about 5° C., 1 hour.

METHOD VIII

PREPARATION of 4-Benzhydryl-1-(3-hydroxypropyl)piperidine

4-Benzhydrylpiperidine (10 mmol, 2.87 g) is slurried in n-butanol (30 mL), and $K_2CO_3$(s) (2.76 g, 10 mmol) or diisopropylethylamine (20 mmol, 2.5 g) and 3-bromopropanol (10 mmol, 1.39 g) are added to the slurry. The stirred mixture is refluxed for about 7 hours under $N_2$(g), filtered, and concentrated in vacuo. The residue is dissolved in hot $CHCl_3$, filtered and concentrated in vacuo to yield crude product as an oil (3.0–3.1 g) which is used without further purification.

METHOD IX

PREPARATION of 4-Benzhydryl-1-(3-chloropropyl)piperidine

Crude hydroxypropyl piperidine from above (3.1 g, ≦10 mmol) in anhydrous $CHCl_3$ or $CH_2Cl_2$ (30 mL) is treated with thionyl chloride (10 mmol) and the mixture is refluxed for about 2 hours under dry $N_2$(g). The residue after evaporation in vacuo is chromatographed on silica (10% MeOH in $CH_2Cl_2$) to yield 1.6 g of product as a white solid.

METHOD X

PREPARATION of 1-Benzhydryl-4-(3-hydroxypropyl)piperazine

To 1-benzhydrylpiperazine (64 mmol) and diisopropylethylamine (77 mmol) in dioxane/$H_2O$ (9:1, 100 mL) is added 3-bromo-1-propanol (64 mmol) while stirring. After about 17 hours, the solution is concentrated in vacuo, and the residue is taken up in EtOAc (250 mL) and washed with 1N NaOH (2×100 mL), and brine (2×). The organic phase is dried over $Na_2SO_4$(s), concentrated in vacuo and recrystallized from hot EtOAc to afford white crystalline product.

Compounds of formula I are inhibitors of the functions of P-glycoprotein, particularly human MDR1 protein or P-glycoprotein related and membrane associated proteins which participate in the transport of xenobiotics or proteins across membranes such as, cell membranes of eukaryotic and prokariotic origin, e.g., pmfdr, however not exclusive or restricted to these examples.

Compounds included in general formula I are useful in combination chemotherapy of cancer, malaria, viral infections such as AIDS, in therapy of septic shock syndrome or inflammation and may be useful in enhancing of the xenobiotics limited due to the presence of P-glycoprotein or P-glycoprotein related functional proteins. Compounds of formula I increase the activity/efficacy of adriamycin, daunomycin, etoposide, topotecan, teniposide, actinomycin D, taxol, vincristine, vinblastine, anthracycline antibiotics and of drugs which are structurally and functionally related to the above mentioned examples. In particular, compounds of formula I are useful when the activity of such drugs has been shown to be limited due to the presence and function of P-glycoprotein, e.g. human MDR1 protein or P-glycoprotein related proteins.

The effectiveness of the compounds of the present invention in sensitizing multidrug resistant KBV-1 cells to adriamycin (ADR) (Aria Labs) were sometimes identified using an assay which determined the degree of potentiation of adriamycin's cytotoxicity effects by the compounds. Plates inoculated with 5×10³ cells in 200 μL RPMI 1640 (J.R.H. Bioscience) supplemented with 10% fetal bovine serum albumin plus penicillin (100 units/mL) and streptomycin (100 μg/mL) were incubated 1 day at 37° C., 5% $CO_2$ and 98% humidity. RPMI media (25 μL) containing 50 μM adriamycin was added to each plate (5 μM ADR final). Compounds (30 mM) were solubilized in DMSO and diluted with 1 mM Tris buffer, pH 7.4, and 25 μL aliquots of appropriately diluted solutions were added to test plates of cells (in triplicate) to produce final concentrations of 15 μM to 15 nM compound per plate. Control plates were treated with 25 μL of the appropriate DMSO/Tris buffer "blank" solutions for comparison. All plates were incubated at 37° C., 5% $CO_2$, 98% humidity for 66 h. before adding 25 μL of MTT (2.5 mg/mL) (3-[4,5-Dimethylthiazol-2-yl]-2,5-diphenyltetrazolium bromide, Sigma) and incubating for 3 h. Media was aspirated and DMSO (100 μL) was added to each plate. Plates were placed on a shaking platform for 30–60 min. to dissolve the dye and then the optical density was determined at 570 nm as a relative measure of cell viability.

The compounds of the present invention are evaluated as potentiators of chemotherapeutic agents using a Cellular Drug Retention Assay. This assay was designed to study the effect of compounds on cellular retention of radiolabeled drug. In this case $^{14}$C-adriamycin retention by multidrug resistant human carcinoma cells, KBV1, is measured. The KBV1 cell line was obtained from M. Gottesman and I. Pastan of the National Cancer Institute, Bethesda, Ma., 20892, U.S.A.

KBV1 cells are routinely grown in tissue culture as monolayers in DMEM high glucose medium containing 1 μg/ml vinblastine, 10% heat inactivated fetal calf serum and supplemented with glutamine, pen-strep and garamycin.

The assay protocol (described below) is applicable with minor modifications, to a wide variety of cell lines grown in tissue culture.

Assay Protocol:
(1) Seed replicate 6-well tissue culture plates with 1.2× 10⁶ cells per 2 ml per well in absence of vinblastine;
(2) Incubate 24 hours at 37° C. in humidified incubator (5% $CO_2$);
(3) Aspirate off the spent media and overlay monolayers with 2 ml/well of fresh medium that contains 2 μM adriamycin (2 μM unlabeled adriamycin+20,000 cpm of $^{14}$C-adriamycin) and the test compound at concentrations varying from 0 to 100 μM;
(4) Following incubation for 3 hours at 37° C. in humidified incubator, remove media and wash monolayers twice with 2 ml of ice cold buffered saline;
(5) Detach monolayers using 0.5 ml of trypsin/EDTA, collect detached cells and transfer to scintillation vial. Rinse wells once with 0.5 ml of buffered saline and add to same vial containing cells;
(6) Add 5 ml of Beckman Ready-Safe™ scintillation fluid to vial, vortex and determine radioactivity per sample using a scintillation counter (10 minutes per sample);

(7) For background control: pre-incubate monolayers at 4° C. for 15 minutes then remove media and add fresh ice-cold media containing adriamycin (see step 3). Following incubation for 3 hours at 4° C. remove media and wash monolayers twice with 2 ml ice-cold buffered saline, then proceed as in step 5;

(8) Results are expressed as T/C and ED3× values as defined below:

T/C=pmoles adriamycin per $10^6$ cells treated with test compound/concentration

ED3×=concentration of test compound that produces a 3 fold increase in cellular accumulation of radiolabeled adriamycin, i.e. T/C=3.

Calculation

Specific cpm=[sample cpm—background cpm]

Specific activity=[cpm/total conc. of adriamycin]

pmoles adriamycin=[specific cpm/specific activity]

pmoles adriamycin per $10^6$ cells=[(pmoles adriamycin per well/number of cells per well)×$10^6$ cells]

As previously mentioned, compounds of the present invention and salts thereof are useful in potentiating the anticancer effects of chemotherapeutic agents. Such agents can include adriamycin, daunomycin, topotecan, teniposide, actinomycin D, vinblastine, vincristine, etoposide, mitomycin C and anthramycin.

The compounds of the present invention can be administered with, 24 hours before or up to 72 hours after the administration of the chemotherapeutic agents. When administered with said agents, they can be taken either separately or coadmini-stered in the same formulation.

The compounds of the present invention, whether taken separately or in combination with an anti-cancer agent, are generally administered in the form of pharmaceutical compositions comprising at least one of the compounds of formula I and optionally a chemotherapeutic agent, together with a pharmaceutically acceptable vehicle or diluent. Such compositions are generally formulated in a conventional manner utilizing solid or liquid vehicles or diluents as appropriate to the mode of desired administration such as oral, buccal, transdermal, parenteral, rectal or slow infusion. For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. sodium lauryl sulphate or sodium starch glycolate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily, aqueous or alcoholic vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For use in the potentiation of anticancer agents in a mammal, including man, a compound of formula I is given in an amount of about 0.5–250 mg/kg/day, in single or divided doses. A more preferred dosage range is 2–50 mg/kg/day, although in particular cases, at the discretion of the attending physician, doses outside the broader range may be required. The preferred route of administration is generally parenteral either as a bolus injection or as a continuous infusion, but oral administration will be preferred in special cases. For compounds of this invention administered as a bolus intravenous injection the preferred dosage range is typically 0.1–5 mg/kg/day. When the compounds of this invention are administered as a continuous intravenous infusion, a 0.1–5 mg/kg loading dose is given as an i.v. bolus injection followed by a maintenance slow infusion of 0.1–2 mg/h/kg (depending on the targeted plasma level and the individual's clearance rate) begun 1 hour before and continuing for at least 3 hours following dosing of a chemotherapeutant is preferred. When a compound of this invention is administered orally, the preferred dosage range is 0.5–50 mg/kg/day. The maximal doses of the compounds of this invention is determined by the toleration of the combination of a compound of this invention and a particular cytotoxic agent by the patient.

The present invention is illustrated by the following examples, but is not limited to the details or scope thereof.

Amberlite IRA 400 ($^-$OH) ion exchange resin was purchased from Aldrich Chemical Co., Inc (Milwaukee, Wis., 53233) and washed thoroughly with 80% dioxane/$H_2O$ and MeOH and dried before use in reactions.

Analytical reverse phase (RP) HPLC is carried out by injecting samples, dissolved in a solvent miscible with water, onto a Perkin Elmer Pecosphere column ($C_{18}$, 3 mm×3 cm, available from Perkin Elmer Corp. Norwalk, Conn. 06859) with a Brownlee RP-8 Newguard precolumn (7 micron, 15 mm×3.2 mm, available from Applied Biosystems Inc., San Jose, Calif. 95134). The samples are eluted with a linear gradient of 0 to 100% acetonitrile/pH 4.55, 200 mM $NH_4OAc$ buffer over 10 minutes, at 3.0 mL/minute. UV detection is typically at 240–310nm depending on the $\lambda_{max}$ of the heterocycle in the sample.

Preparative reverse phase (RP) HPLC is performed using a Dynamax-60A C18 (8 $\mu$m) column (21.4 mm×25 cm) equipped with a Guard Module (21.4 mm×25 cm), both available from Rainin Instrument Co. Reaction mixture residues are taken up in $CH_3CN/H_2O$ or MeOH/$H_2O$ at pH 4–5 and injected onto the column which had previously been washed and equilibrated in 0 to 15% $CH_3CN$/pH 4.5 50 mM $NH_4OAc$ buffer. Elution of components is carried out with a linear gradient of 1% $CH_3CN$/minute at 20–25 mL/min. flow rates with detection at 260–310 nm as appropriate for heterocyclic fragments.

EXAMPLE 1

Method A

1-[4-(10,11-Dihydro-5H-dibenzo[a,d]cyclohepten-5-yl)piperazin-1-yl]-3-(2-methyl-benzothiazol-7-yloxy)propan-2-ol hydrochloride 2-Methyl-7-(oxiran-2-ylmethoxy)benzothiazole (0.79 mmol, 174 mg) and 1-(10,11-dihydro-5H-dibenzo[a,d]cyclohepten-5-yl)piperazine were stirred at reflux about 80° C. in 20% DMF/80% EtOH (5 mL) for 3 hours. The residue after concentration in vacuo was flash chromatographed on silica in 35% acetone/hexanes to afford 204 mg of product as its free base (52%). This material was dissolved in $Et_2O$ and 1N-HCl in $Et_2O$ (1.0 eq, 0.41 mL) was added dropwise with stirring under dry $N_2(g)$. After 30 min, the suspension was chilled, and the white precipitate was recovered by centrifugation (with 2× washes of pellet with anhydrous $Et_2O$) and dried in vacuo to yield 190 mg (86% recovery) of the hydrochloride salt. LSIMS m/z 500 ($MH^+$ of $C_{30}H_{33}N_3O_2S$); mp 153.5° C.

EXAMPLE 2

Method A 1-(4-Benzhydryl-piperazin-1-yl)-3-(2-benzothiazol-2-yl-phenoxy)propan-2-ol A solution of 1-benzhydryl-piperazine (891 mg, 3.53 mmol) and 2-[2-(oxiran-2-yl-methoxy)phenyl]benzothiazole (1000 mg, 3.53 mmol) in EtOH (7 mL) were refluxed under $N_2(g)$ for about 16 hours. The mixture was concentrated in vacuo to a white foam and flash chromatographed on silica (35% EtOAc/hexanes) to afford 807 mg (42%) of the free base of the product as a white solid. mp 152–155° C.; LSIMS m/z 536 ($MH^+$).

EXAMPLE 3

Method B 1-(4-Benzhydryl-piperidin-1-yl)-3-(2-pyridin-2-yl-benzothiazol-5-yloxy)propan-2-ol 4-Benzhydrylpiperidine (1.63 mmol, 0.47 g) and 5-(oxiran-2-ylmethoxy)-2-pyridin-2-yl-benzothiazole (1.62 mmol, 0.46 g) were stirred at reflux (about 80° C.) under $N_2(g)$ in 20% DMF/80% EtOH (5 mL) for 16 hours. The mixture was concentrated in vacuo and the residue was flash chromatographed on silica using 35% acetone/65% hexanes to afford 340 mg of product as its free base (39%; white powder). This material was dissolved in a minimal amount of $CHC_3$ and 1N HCl in $Et_2O$ (1.1 eq, 0.70 mL) was added dropwise with stirring. After about 30 min. the mixture was concentrated in vacuo and the residual white solid was triturated with $Et_2O$, filtered and dried in vacuo to yield 337 mg (92% recovery) of the product as its monohydrochloride salt. LSIMS m/z 535 ($MH^+$ of $C_{33}H_{33}N_3O_2S$); mp 165–172° C.

EXAMPLE 4

Method $C_A$ 1-(4-BenzhydrVl-piperazin-1-yl)-3-(2-benzoxazol-2-yl-phenoxy)propan-2-ol To 2-(benzoxazol-2-yl)phenol (342 mg, 1.62 mmol) dissolved in propan-2-ol (5 mL) was added 6 N KOH (0.8 mmol, 130 mL), diisopropylethyl amine (209 mg, 1.62 mmol), and 1-benzhydryl-4-(oxiran-2-ylmethyl)-piperazine (500 mg, 1.62 mmol). The reaction mixture was refluxed under $N_2(g)$ for about 36 hours, then concentrated in vacuo and flash chromatographed on silica (20% acetone/hexanes) to afford 375 mg (49%) of the product as its free base. mp 140–143° C.; LSIMS m/z 520($MH^+$).

EXAMPLE 5

Method $C_B$ 1-(4-Benzhydryl-piperazin-1-yl)-3-(3-[1.3,4]-thiadiazol-2-yl-phenoxy)propan-2-ol To 1-benzhydryl-4-(oxiran-2-ylmethyl)-piperazine (617 mg, 2.0 mmol) and 3-([1,3,4]thiadiazol-2-yl)phenol (534 mg, 3.0 mmol) in n-BuOH (8 mL) was added $K_2CO_3$(s) (414 mg, 3.0 mmol). The stirred mixture was heated to reflux under $N_2(g)$ for about 22 hours. The mixture was partitioned between 0.5N NaOH and 1:1 EtOAc/$Et_2O$. The organic phase was dried over $Na_2SO_4$(s), concentrated in vacuo and flash chromatographed on silica (25% acetone/hexanes) to yield 392 mg (40%) of the product as its free base. This material was dissolved in minimal $CHCl_3$ and treated dropwise with 1M HCl in $Et_2O$ (0.85 mL, 0.85 mmol). After dilution to 20 mL with $Et_2O$ and 30 min. stirring at about 20° C. the monohydrochloride salt was recovered by filtration and dried in vacuo. 418 mg, 40%; mp 144–146° C.; LSIMS m/z 487.

EXAMPLE 6

Method $C_C$ 1-(4-Benzhydryl-piperazin-1-yl)-3-(2-benzotriazol-2-yl-4-methyl-phenoxy)propan-2-ol 1-Benzhydryl-4-(oxiran-2-ylmethyl)-piperazine (300 mg, 0.97 mmol) was added to the solution resulting from addition of catalytic NaH (5 mg of 60% dispersion in oil) to 2-(2'-hydroxy-5-methylphenyl)benzotriazole (219 mg, 0.97 mmol) in DMF (3 mL). The mixture was heated to about 50° C. for about 72 hours under $N_2(g)$, and then partitioned between 1N NaOH and 1:1 $Et_2O$/EtOAc. The organic phase was washed with 0.5N NaOH and brine, dried over $Na_2SO_4$(s) and concentrated in vacuo. The residue was flash chromatographed on silica (20% acetone/hexanes) to afford 211 mg (41%) of product as its free base. This material was converted to its monohydrochloride salt by precipitation from $Et_2O$ on titration with 1 M HCl in $Et_2O$ (1.0 eq). mp 218–219° C.; LSIMS m/z 534 ($MH^+$).

EXAMPLE 7

Method D

2-[2-[2-(4-Benzhydryl-piperazin-1-yl)-ethoxy]phenyl]-benzothiazole

1-Benzhydryl-piperazine (2.26 g, 8.98 mmol) and 2-[2-(2-bromoethoxy)phenyl]-benzothiazole (0.75 g, 2.24 mmol) were stirred in t-BuOH (20 mL) at about 50° C. under $N_2(g)$ for 24 hours. The mixture was concentrated in vacuo and flash chromatographed on silica (15% acetone/hexanes) to afford 460 mg (41%) of the free base of the product. mp 67–72° C.; LSIMS m/z 506 ($MH^+$).

EXAMPLE 8

Method $E_A$

6-[3[4-(Benzhydryl)piperazin-1-yl]propoxy]benzothiazole

6-Hydroxybenzothiazole (2.8 mmol, 423 mg) was dissolved in dry DMF (2.8 mL) by the addition of $Me_4N^+OH^-$ .5H₂O (490 mg, 2.7 mmol) with stirring under N₂(g). 1-Benzhydryl-4-(3-bromopropyl)piperazine (716 mg, 2.0 mmol) was added to the solution and the mixture was stirred under N₂(g) at about 50° C. for 16 hours. The reaction mixture was partitioned between 1N NaOH (25 mL) and 1:1 EtOAc/Et₂O (25 mL). The organic phase was washed with 1N NaOH (2×10 mL), and brine(10 mL), dried over Na₂SO₄(s) and concentrated in vacuo. The residue was flash chromatographed on silica (25 to 35% acetone/hexanes) to afford 452 mg (51%) of the product as its free base. This material was dissolved in a minimal amount of CHCl₃ at about 20° C., and 1M HCl in Et₂O (1.05 ml, 1.0 eq) was added dropwise with stirring. After the addition the suspension was diluted to ~20 ml with anhydrous Et₂O and the precipitated monohydrochloride salt was filtered and dried in vacuo; 403 mg, 42%. mp 136–137° C.; LSIMS m/z 444 (MH⁺).

EXAMPLE 9

Method $E_B$

1-Benzhydryl-4-[3-[2-(oxazol-2-yl)phenoxy]-propyl]piperazine 2-(Oxazol-2-yl)phenol (125 mg, 0.78 mmol) in dry DMF (2.0 ml) was treated with NaH (0.78 mmol; 32 mg of 60% dispersion in oil). After stirring 10 min. at about 20° C. H₂(g) evolution had ceased and KI (86 mg, 0.52 mmol) along with 1-benzhydryl-4-(3-bromopropyl)piperazine (193 mg, 0.52 mmol) were added to the solution. The mixture was stirred at about 50° C. under N₂(g) for about 16 hours. The mixture was partitioned between 1N NaOH (25 mL) and 1:1 EtOAc/Et₂O (30 mL). The organic phase was washed with 1N NaOH (2×10 mL), dried over Na₂SO₄(s), and concentrated in vacuo. The residue was flash chromatographed on silica (15 to 30% acetone/hexanes) to afford 190 mg (80%) of product as the free base. The monohydrochloride salt was prepared by titration of the residue in etheral solution (15 mL) dropwise with 1M HCl in Et₂O (0.65 mL). After about 30 min. stirring the precipitated salt was filtered and dried in vacuo, 201 mg, 80%. Decomposed at 160° C. without melting; LSIMS m/z 454 (MH⁺).

EXAMPLE 10

Method $E_C$ 3-(4-[2-[3-(4-Benzhydryl-piperidin-1-yl)-propoxy]phenyl]-thiazol-2-yl)pyridine 4-Benzhydryl-1-(3-chloropropyl)piperidine (329 mg, 1.0 mmol), 2-[2-(pyridin-3-yl)thiazol-4-yl]phenol (318 mg, 1.25 mmol) and n-Bu₄N⁺I⁻(1.0 mmol, 369 mg) in CHCl₃ (3 mL) were stirred vigorously with 0.5N NaOH (10 mL, 5.0 mmol) at about 20° C. under N₂(g) for about 72 hours. The mixture was diluted with CHCl₃ (25 mL) and the organic phase was separated, washed with 0.5N NaOH and brine, dried over NaSO₄(s), and concentrated in vacuo. The residue was flash chromatographed on silica (35% acetone/hexanes) to afford 120 mg (22%) of the product as its free base. This material was dissolved in CH₃CN (10 mL) and 1N HCl in Et₂O (0.5 mL, 0.5 mmol) was added dropwise with stirring. After about 30 min. stirring at about 20° C., the mixture was diluted with Et₂O (50 mL) and the dihydrochloride salt was recovered by filtration and dried in vacuo, 130 mg, 21%. mp 159–160° C.; LSIMS m/z 547 (MH⁺).

EXAMPLE 11

Method F

1-Benzhydryl-4-[3-(2-imidazol-1-ylmethyl-phenoxy)-propyl]piperazine

To a stirred partial suspension of Ph₃P (629 mg, 2.4 mmol) and 2-(imidazol-1-yl)methylphenol (350 mg, 2.0 mmol) in dry THF (7.0 mL) under N₂(g) at about 0° C. was added diethyl azodicarboxylate (380 mL, 2.4 mmol) dropwise over 2 minutes. During the addition all starting materials dissolved, and 5 minutes after completion of the addition a suspension of 1-benzhydryl-4-(3-hydroxypropyl)piperazine (620 mg, 2.0 mmol) in dry THF (5.0 mL +2.0 mL rinse) was added dropwise over 5 min. at about 0° C. The resulting solution was stirred for about 20 min. at about 0° C., and 16 hours at about 20° C. before concentrating in vacuo to a syrup. The residue was dissolved in Et₂O/EtOAc (25 mL) and 1M HCl in Et₂O (2.0 mL, 2.0 mmol) was added dropwise with stirring. Precipitated HCl salts were recovered by filtration and partitioned between 1N NaOH in brine (50 mL) and EtOAc (60 mL). The organic phase was washed with 1N NaOH in brine (2×), saturated Na₂CO₃, and brine, dried over Na₂SO₄(s) and concentrated in vacuo to afford >90% pure product as the free base (650 mg, 70%). The material was dissolved in CHCl₃, titrated with 1M HCl in Et₂O (2.8 mL, 2.8 mmol), and diluted to 20 mL with dry Et₂O to precipitate the dihydrochloride salt, 503 mg. mp 163–165° C. (dec); LSIMS m/z 467 (MH⁺).

EXAMPLE 12

Method $G_A$

N-[1-(3-(4-[2-Hydroxy-3-(2-methylbenzothiazol-7-yloxy)-propyl]-piperazin-1-yl)propyl)-1H-benzimidazol-2-yl]-4-methoxy-benzamide 4-Methoxy-N-[1-(3-piperazin-1-yl-propyl)-1H-benzoimidazol-2-yl]-benzamide (87 mg, 0.22 mmol) and 2-methyl-7-(oxiran-2-ylmethoxy)-benzothiazole (50 mg, 0.22 mmol) were dissolved in 5:1 dioxane/H₂O (1.2 mL) and Amberlite IRA400® resin (⁻OH form; 100 mg of 2.3 meq/g, 1.1 eq) was added. The mixture was heated with stirring to about 65° C. for about 20 h under N₂(g), and then filtered and concentrated in vacuo. The residue was taken up in 80% CH₃CN/pH 4.5, 2.0 M NH₄OAc (1.5 mL) and injected on a preparative RP-HPLC column ((21.4 mm×25 cm) Dynamax-60A C18 column) equilibrated in 15% CH₃CN/85% pH 4.5, 50 mM NH₄OAc and eluted (23 mL/min) with a 1% CH₃CN/min gradient. The largest eluting peak was concentrated in vacuo and the residue partitioned between saturated aqueous Na₂CO₃ and EtOAc. The organic phase was dried over Na₂SO₄(s), and concentrated in vacuo to afford 85 mg (63%) of the product as its free base. The free base was dissolved in CHCl₃ (4–5 mL), and 1 M HCl in Et₂O (2.1 eq) was added. The resulting suspension was diluted with dry Et₂O (to 20 mL) and cooled to about 0–4° C. The precipitated salt was filtered, washed with anhydrous Et₂O and petroleum ether and dried in vacuo to yield 89 mg of the dihydrochloride; LSIMS m/z 615 (MH⁺); MP 208° C. (dec).

EXAMPLE 13

Method $G_B$ 1-(2-Methylbenzothiazol-7-yloxy)-3-[trans-(3-phenyl-bicyclo[2.2.1]hept-2-yl-amino)]propan-2-ol trans-3-Phenyl-bicyclo[2.2.1]hept-2-ylamine hydrochloride (81 mg, 0.362 mmol) and 2-methyl-7-(oxiran-2-ylmethoxy)benzothiazole (81 mg, 0.366 mmol) were dissolved in dioxane and 1N NaOH (1.0 eq, 0.362 mmol, 0.362 mL). Amberlite IRA400® resin (0.16 g, of 2.3 meq/g, 1.05 eq) was added and the gently stirred mixture was heated to about 80° C. for about 20 h. under N₂(g). The resin was removed by filtration and the filtrate was concentrated in vacuo. The purified product (88 mg, 59%) was obtained as its free base following preparative RP-HLPC, concentration of peak fractions and extraction as detailed in Method $G_A$. The free base was dissolved in EtOAc (≈3 mL) and 1.1 equivalent of 1N HCl in ether (0.24 mL) was added. After dilution with dry Et$_2$O and petroleum ether and dried in vacuo; LSIMS m/z 409 (MH$^+$); mp 233° C. (dec).

EXAMPLE 14

Method A

5-[3-(4-Diphenylmethylpiperazin-1-yl)-2-hydroxypropoxy]-1-(2H)-isoguinolone

A solution of N-diphenylmethyl-piperazine (1.02 g, 3.0 mmol) and 5-(2,3-epoxypropoxy)-1-hydroxy-3,4-dihydroisoquinoline (295 mg, 1.0 mmol) in 20 mL of EtOH was refluxed for about 2 h. The residue obtained after evaporation of the solvent was chromatographed on silica gel (2% MeOH—CH$_2$Cl$_2$) to give 552 mg (87%) of the title compound as an amorphous solid. A HCl solution in ether was added to give quantitatively the di-HCl salt of the title compound; MS 471.2.

EXAMPLE 15

Method H

5-[3-(4-Diphenylmethylpiperazin-1-yl)-propoxy]-3,4-dihydro-2-(1 H)-naphthalenone A suspension of sodium hydride (11 mg 60% oil dispersion, 0.28 mmol) and 5-hydroxy-1-tetralone (43 mg, 0.27 mmol) in 5 mL of THF was warmed to about 50° C. for about 30 min. After addition of N-diphenylmethyl-N'-(3-bromopropyl)piperazine (100 mg, 0.27 mmol) the mixture was stirred at about 50° C. for about 3 h. Evaporation of the solvent and silica gel chromatography of the residue (diethyl ether-CH$_2$Cl$_2$=1:4) gave 100 mg (83%) of the title compound as an oil; MS 455.4.

EXAMPLE 16

5-[3-(4-Diphenylmethylpiperazin-1-yl)-2-hydroxypropoxy]-3,4-dihydro-2-(1 H)-naphthalenone methyloxime The product of Example 3 (50 mg, 0.09 mmol) and the methoxyamine.HCl (8 mg, 0.09 mmol) were dissolved in 5 mL of methanol and refluxed for 3 h. The solvent was removed and the residue was chromatographed on silica gel (2.5% MeOH—CH$_2$Cl$_2$) to give 37 mg (70%) of the title compound; mp>183° C. decomposition; MS 500.3.

EXAMPLE 17

5-[3-(4-Diphenylmethylpiperazin-1-yl)-2-hydroxypropoxy]-3,4-dihydro-2-(1 H)-naphthalenone oxime The title product was synthesized substantially according to the method of Example 16 but using hydroxylamine. HCl rather than methoxyamine. HCl. 61% yield; m.p. 177° C.; M.S. 486.4.

EXAMPLES 18–32

Hydroxy Benzazole Derivatives

Compounds of Examples 18–32 having the general formula

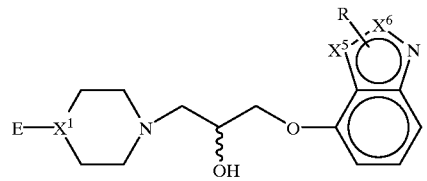

were synthesized according to the methods shown.

| Example Number | E | X$^1$ | X$^5$ | X$^6$ | R | Prep. Method | M.P. (° C.) | Mass Spec. |
|---|---|---|---|---|---|---|---|---|
| 18 | dibenzocycloheptyl | N | S | C | 2-CH$_3$ | A | 154° (dec.) | 500 |
| *19 | dibenzocycloheptyl | N | S | C | 2-CH$_3$ | A | 150° (dec.) | 500 |
| *20 | 2-CF$_3$-benzyl | N | S | C | 2-CH$_3$ | A | 205° (dec.) | 456 |

-continued

| Example Number | E | $X^1$ | $X^5$ | $X^6$ | R | Prep. Method | M.P. (° C.) | Mass Spec. |
|---|---|---|---|---|---|---|---|---|
| 21 | (Ph)$_2$C— | CH | S | C | 2-CH$_3$ | B | 111° (dec.) | 473 |
| 22 | dibenzosuberyl | N | S | C | 2-pyridin-2-yl | A | 154° (dec.) | 563 |
| 23 | (Ph)$_2$C— | CH | S | C | 2-pyridin-2-yl | A | 240° (dec.) | 536 |
| 24 | dibenzosuberyl | N | S | C | H | A | 181–182° (dec.) | 486 |
| 25 | dibenzosuberyl | N | S | C | 2-CN | A | 140° (dec.) | 511 |
| *26 | 2-(propylthio)phenyl | N | S | C | 2-CH$_3$ | A | 110–120° (dec.) | 458 |
| 27 | dibenzosuberyl | N | N | S | | A | 185–190° | 487 |
| 28 | dibenzosuberyl | N | N | N | 3-CH$_3$ | A | 131° (dec.) | 484 |
| 29 | (Ph)$_2$C— | CH | N | N | 3-CH$_3$ | A | 120° (dec.) | 457 |
| 30 | (Ph)$_2$C— | CH | N | CH | 3-CH$_3$ | A | 65–75° (dec.) | 456 |
| 31 | dibenzosuberyl | N | N | CH | 3-CH$_3$ | A | 170° (dec.) | 483 |

-continued

| Example Number | E | X¹ | X⁵ | X⁶ | R | Prep. Method | M.P. (° C.) | Mass Spec. |
|---|---|---|---|---|---|---|---|---|
| 32 | 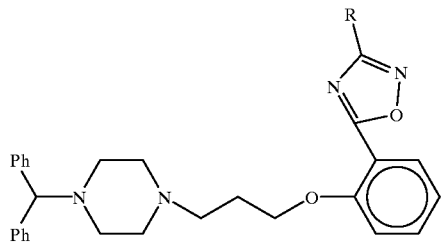 | CH | S | C | 2-CH₃ | A | 122–135° (dec.) | 481 |

*The R-enantiomer at the 2-propanol position (≧86% enantiomeric excess).

EXAMPLES 33–35

Compounds of Examples 33–35 having the general formula

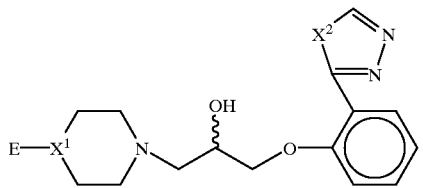

were synthesized according to the methods shown.

| Example Numbers | R | Prep. Method | M.P.(° C.) | Mass Spec.(MH⁺) |
|---|---|---|---|---|
| 33 | pyridin-3-yl | $E_A$ | 228–229° C. | 532 |
| 34 | pyridin-2-yl | $E_A$ | 158–160° C. | 532 |
| 35 | pyridin-4-yl | $E_A$ | 223–224° C. | 532 |

EXAMPLES 36–38

Compounds of Examples 36–38 having the general formula

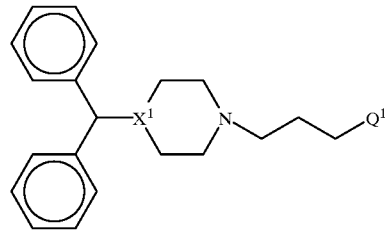

were synthesized according to the methods shown.

| Example Numbers | E | X¹ | X² | Prep. Method | M.P.(° C.) | Mass Spec. |
|---|---|---|---|---|---|---|
| 36 | (Ph)₂CH | N | O | A | 210°(dec.) | 471 |
| 37 | PhCH₂ | CH | O | A | 128–130° | 394 |
| 38 | (Ph)₂CH | N | S | $C_B$ | 178–182° | 487 |

EXAMPLES 39–45

Compounds of Examples 39–45 having the general formula

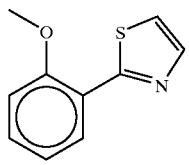

where synthesized according to the methods shown.

| Example Numbers | X¹ | Q¹* | Prep. Method | M.P. (° C.) | Mass Spec. |
|---|---|---|---|---|---|
| 39 | N | 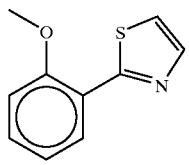 | $E_A$ | 205–210° (dec.) | 470 |

-continued
| Example Numbers | $X^1$ | $Q^{1*}$ | Prep. Method | M.P. (° C.) | Mass Spec. |
|---|---|---|---|---|---|
| 40 | N | 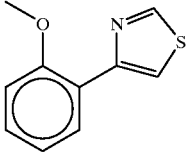 | $E_B$ | 221.5–223° | 470 |
| 41 | N | 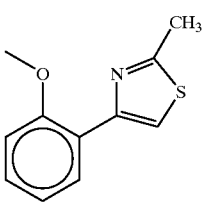 | $E_B$ | 233–235.5° | 484 |
| 42 | N | 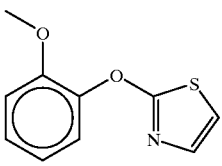 | $E_A$ | 180–182° | 486 |
| 43 | CH | 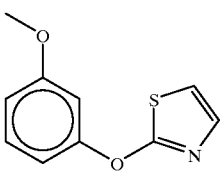 | $E_C$ | 67–68° | 485 |
| 44 | CH | 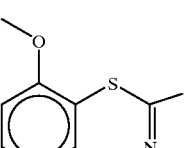 | $E_C$ | 135–137° | 501 |
| 45 | N | 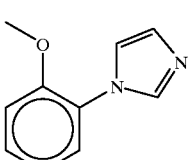 | $E_A$ | 180° | 453 |
*Bonded through the phenoxy O.

EXAMPLES 46–56

Compounds of Examples 46–56 having the general formula

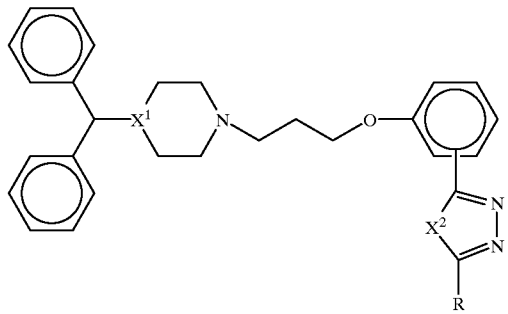

were synthesized according to the methods shown.

| Ex. No. | X¹ | X² | R | Prep. Meth. | M.P.(° C.) | Mass Spec. | Position of Diazole |
|---|---|---|---|---|---|---|---|
| 46 | CH | O | H | D | 104–106° | 454 | ortho |
| 47 | N | O | —CH₃ | E_B | 201–202° | 469 | ortho |
| 48 | N | O | —SCH₃ | E_A | 226.5–228° | 501 | ortho |
| 49 | N | O | pyridin-3-yl | E_A | *160–161.5° | 532 | ortho |
| 50 | N | S | pyridin-3-yl | E_A | >240°(dec.) | 548 | ortho |
| 51 | N | S | pyridin-4-yl | E_A | >200°(dec.) | 548 | ortho |
| 52 | N | S | H | E_A | 163–164.4° | 471 | meta |
| 53 | N | S | H | E_A | 250–253.4° | 471 | ortho |
| 54 | N | S | —N(CH₃)₂ | E_A | *153–154.3° | 514 | ortho |
| 55 | N | S | —CH₃ | E_A | 128–130° | 485 | ortho |
| 56 | N | S | phenyl | E_A | 152–155° | 547 | meta |

*M.P. reported for the free base.

EXAMPLES 57–64

Compounds of Examples 57–64 having the general formula

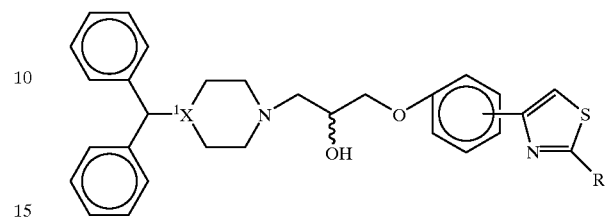

were synthesized according to the methods shown.

| Example Number | X¹ | Position of Thiazole | R | Prep. Method | M.P.(° C.) | Mass Spec. (FAB) |
|---|---|---|---|---|---|---|
| 57 | N | meta | —CH₃ | A | 189–191 | 500 |
| *58 | N | meta | phenyl | A | 109–110 | 562 |
| 59 | N | meta | pyridin-2-yl | A | 138–139 | 563 |
| 60 | N | meta | pyridin-3-yl | A | 163–165 | 563 |
| 61 | N | meta | pyridin-4-yl | A | 205–206 | 563 |
| *62 | N | para | pyridin-2-yl | A | 158–159 | 563 |
| *63 | N | para | —CH₃ | A | 129–130 | 500 |
| *64 | CH | meta | pyridin-4-yl | B | 115–116 | 563 |

*The M.P. reported are for the free base.

EXAMPLES 65–73

Compounds of Examples 65–73 having the general formula

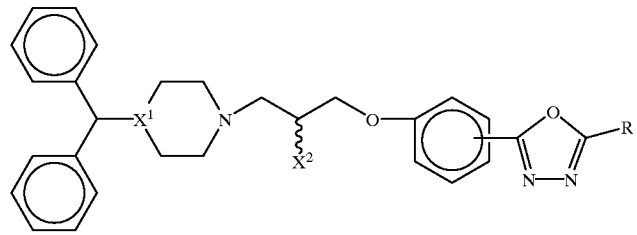

were synthesized according to the methods shown.

| Example Number | X¹ | X² | Position of Oxadiazole | R | Prep. Method | M.P.(° C.) | Mass Spec.(FAB) |
|---|---|---|---|---|---|---|---|
| *65 | N | OH | meta | H | A | 128–129 | 471 |
| 66 | N | OH | meta | —CH₃ | A | 185–186 | 485 |
| 67 | N | OH | meta | —CH₂CH₃ | A | 134 | 499 |
| 68 | N | OH | para | —CH₃ | A | 119 | 485 |
| 69 | N | OH | para | —CH₂CH₃ | A | 204–206 | 499 |

-continued

| Example Number | $X^1$ | $X^2$ | Position of Oxadiazole | R | Prep. Method | M.P.(° C.) | Mass Spec.(FAB) |
|---|---|---|---|---|---|---|---|
| 70 | CH | OH | para | —CH$_2$CH$_3$ | B | 201–202 | 498 |
| 71 | CH | OH | meta | —CH$_2$CH$_3$ | B | 150.5 | 498 |
| 72 | CH | H | meta | —CH$_2$CH$_3$ | C | 189–193 | 482 |
| 73 | CH | H | para | —CH$_3$ | C | 183(dec.) | 468 |

*The M.P. reported is for the free base.

EXAMPLES 74–79

Compounds of Examples 74–79 having the general formula

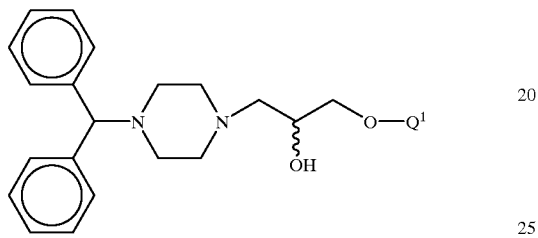

were synthesized according to the methods shown.

| Example Number | $Q^1$ | Prep. Method | M.P.* (° C.) | Mass Spec. (FAB) |
|---|---|---|---|---|
| 74 | 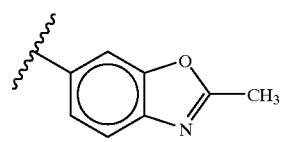 | A | 116–118 | 458 |
| 75 | 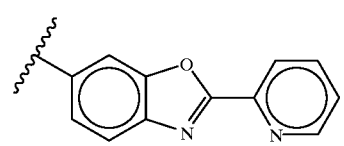 | A | 123–124 | 520 |
| *76 | 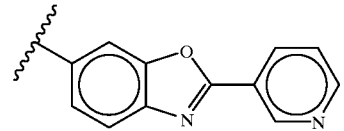 | A | 176–178 | 521 |
| *77 | 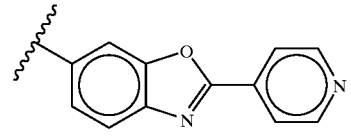 | A | 139–143 | 521 |
| *78 | 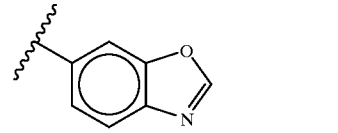 | A | 118–121 | 444 |

-continued
| Example Number | Q¹ | Prep. Method | M.P.* (° C.) | Mass Spec. (FAB) |
|---|---|---|---|---|
| *79 | | A | 144–145 | 536 |
*The M.P. reported is for the free base.
EXAMPLES 80–91
Compounds of Examples 80–91 having the general formula
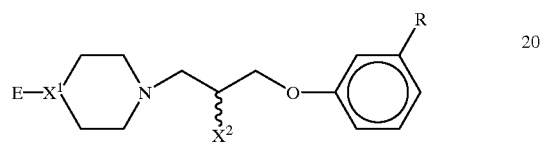
were synthesized according to the methods shown.
| Example Number | E | X¹ | X² | R | Prep. Method | M.P.(° C.) | Mass Spec.(FAB) |
|---|---|---|---|---|---|---|---|
| 80 | —CH(Ph)₂ | N | OH | | A | 194.5–195 | 484 |
| 81 | —CH(Ph)₂ | N | OH | | A | 190–193 | 548 |
| 82 | —CH(Ph)₂ | N | OH | | A | 224 | 548 |
| 83 | —CH(Ph)₂ | N | OH | | A | 120 | 548 |
| 84 | —CH(Ph)₂ | CH | OH | | B | 193–194 | 484 |

-continued
| Example Number | E | $X^1$ | $X^2$ | R | Prep. Method | M.P.(° C.) | Mass Spec.(FAB) |
|---|---|---|---|---|---|---|---|
| 85 | —CH(Ph)$_2$ | CH | OH | 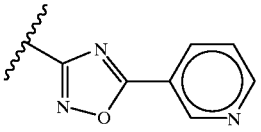 | B | 134 | 547 |
| 86 | —CH(Ph)$_2$ | CH | OH | 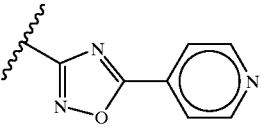 | B | 126–131 | 547.3 |
| 87 | —CH(Ph)$_2$ | CH | OH | 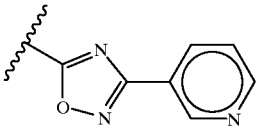 | B | 223.5 | 547 |
| 88 | —CH(Ph)$_2$ | CH | H | 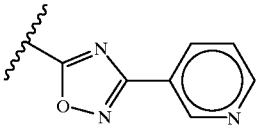 | C | 163 | 531 |
| 89 | —CH(Ph)$_2$ | CH | H | 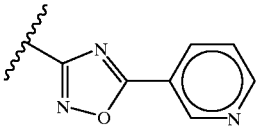 | C | 94–96 | 531 |
| *90 | —CH(Ph)$_2$ | CH | H | 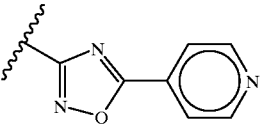 | C | 116–147 | 531 |
| 91 | 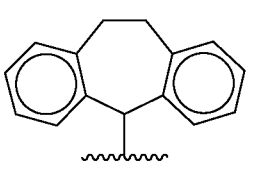 | N | OH | 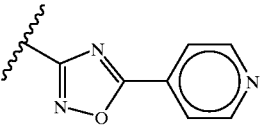 | C | 133–146 | 574 |
*The M.P. reported is for the free base.

EXAMPLES 92–135
Compounds of Examples 92–135 having the general formula
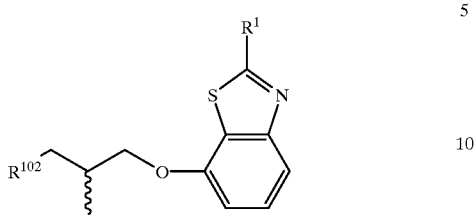
were synthesized according to the methods shown.
| Ex. No. | R[102] Bonded through the amino | R[1] | Prep. Meth. | M.P. (° C.) | Mass Spec. |
|---|---|---|---|---|---|
| 92 | 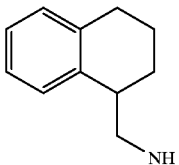 | Me | G$_B$ | 180(dec.) | 383 |
| 93 | 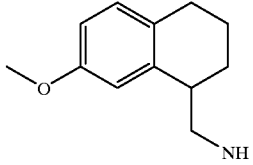 | Me | G$_B$ | 145–150 | 413 |
| 94 | 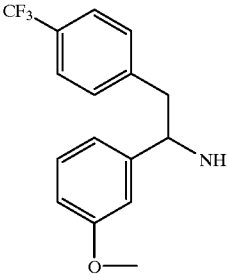 | Me | G$_B$ | 165(dec.) | 517 |
| 95 | 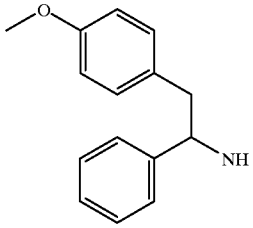 | Me | G$_B$ | 188–197(dec.) | 449 |

-continued

| Ex. No. | R¹⁰² Bonded through the amino | R¹ | Prep. Meth. | M.P. (° C.) | Mass Spec. |
|---|---|---|---|---|---|
| 96 | 3-methoxyphenyl-CH₂-CH(Ph)-NH- | Me | G_B | 160–167(dec.) | 449 |
| 97 | chroman-4-yl-NH- | Me | A | 186(dec.) | 433 |
| 98 | 7-chloro-thiochroman-4-yl-NH- | Me | G_B | 149–168(dec.) | 484 |
| 99 | trans-2-phenylcyclohex-3-enyl-NH- | Me | G_B | 185–195 | 395 |
| 100 | trans-3-phenylnorbornan-2-yl-NH- | Me | G_B | 233(dec.) | 409 |
| 101 | trans-3-phenylnorbornen-2-yl-NH- | Me | G_B | 200(dec.) | 407 |
| 102 | trans-3-(4-methylphenyl)norbornen-2-yl-NH- | Me | A | 150–160(dec.) | 421 |

-continued
| Ex. No. | R[102] Bonded through the amino | R[1] | Prep. Meth. | M.P. (° C.) | Mass Spec. |
|---|---|---|---|---|---|
| 103 | 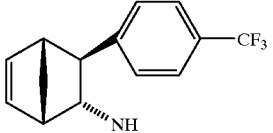 | Me | A | 152–159 | 475 |
| 104 | 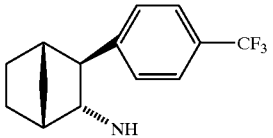 | Me | A | 110–125 | 477 |
| 105 | 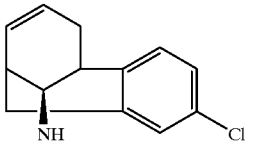 | Me | $G_B$ | 230–236 | 441 |
| 106 | 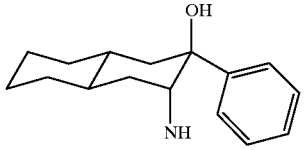 | Me | $G_A$ | 160–165 | 467 |
| 107 | 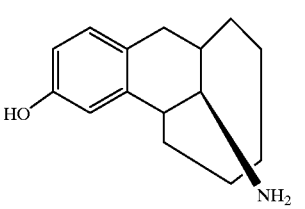 | Me | $G_A$ | 200(dec). | 453 |
| *108 | 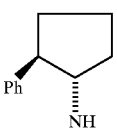 | Me | $G_B$ | 123(dec). | 383 |
| *109 | 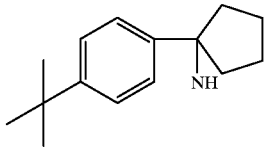 | Me | $G_B$ | 195–197 | 439 |
| *110 | 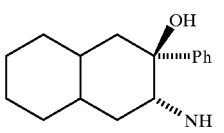 | Me | $G_B$ | 187–189 | 467 |
| 111 | 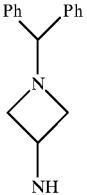 | Me | | 55 | 460 |

-continued

| Ex. No. | R¹⁰² Bonded through the amino | R¹ | Prep. Meth. | M.P. (° C.) | Mass Spec. |
|---|---|---|---|---|---|
| *112 | [decahydronaphthalene with Ph and NH substituents, H stereochemistry shown] | Me | G$_A$ | 156(dec). | 451 |
| *113 | [decahydronaphthalene with Ph and NH substituents, H stereochemistry shown] | Me | G$_A$ | 154(dec). | 451 |
| *114 | [1-phenylcyclopentyl-NH] | Me | G$_B$ | 151–156 | 383 |
| *115 | [1-(4-fluoro-3-methylphenyl)cyclohexyl-NH] | Me | G$_B$ | 161(dec). | 429 |
| *116 | [1-(4-fluorophenyl)cyclohexyl-N(CH₃)] | Me | A | 186 | 429 |
| *117 | [polycyclic structure with 2,6-dichlorophenyl and NH] | Me | G$_B$ | 155–160 | 542 |
| *118 | [dicyclohexyl with butyl and NH] | Me | A | 127–133 | 431 |
| 119 | [polycyclic structure with 2,6-dichlorophenyl and NH] | Me | G$_B$ | 122–125 | 542 |

-continued

| Ex. No. | R¹⁰² Bonded through the amino | R¹ | Prep. Meth. | M.P. (° C.) | Mass Spec. |
|---|---|---|---|---|---|
| *120 | 4-chlorophenyl-cyclohexyl-NH | Me | G_B | 208–209 | 431 |
| *121 | 2,6-dichlorophenyl norbornenyl-NH | Me | A | 108(dec). | 476 |
| *122 | 2,6-dichlorophenyl norbornenyl-NH | Me | A | 110(dec). | 476 |
| *123 | 2-chlorophenyl tetrahydro-methanonaphthyl-NH | Me | A | 207–211(dec). | 508 |
| *124 | 2-chlorophenyl tetrahydro-methanonaphthyl-NH | Me | A | 208–212(dec). | 508 |
| 125 | 4-tert-butylcyclohexyl-NH | Me | G_A | | 377 |
| 126 | 4-tert-butylcyclohexyl-NH | Me | G_A | | 377 |

-continued

| Ex. No. | R¹⁰² Bonded through the amino | R¹ | Prep. Meth. | M.P. (° C.) | Mass Spec. |
|---|---|---|---|---|---|
| *127 | | Me | A | 135(dec). | 441 |
| 128 | | Me | G_B | 120–127(dec). | 463 |
| *129 | | n-Bu | G_B | 186 | 425 |
| *130 | | n-Bu | G_B | 177–181 | 474 |
| *131 | | i-Pr | G_B | 197(dec). | 460 |
| *132 | | i-Pr | G_B | 222 | 405 |
| *133 | | n-Bu | G_B | 209(dec). | 439 |
| *134 | | i-Pr | G_B | 145 | 470 |

-continued

| Ex. No. | $R^{102}$ Bonded through the amino | $R^1$ | Prep. Meth. | M.P. (° C.) | Mass Spec. |
|---|---|---|---|---|---|
| *135 | 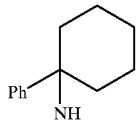 | i-Pr | $G_B$ | | |

*R-isomer at the propan-2-ol.

EXAMPLES 136–158

Compounds of Examples 136–158 having the general formula

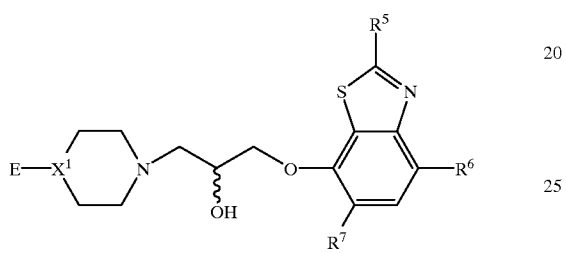

were synthesized according to the methods shown.

| Example Number | E | $X^1$ | $R^5$ | $R^6$ | $R^7$ | Prep. Meth. | M.P. (° C.) | Mass Spec. |
|---|---|---|---|---|---|---|---|---|
| 136 | ![benzimidazole-benzamide] | N | —CH₃ | H | H | $G_A$ | 195–208° (dec) (diHCl) | 615 |
| 137 | ![dimethoxy-isochroman] | C | —CH₃ | H | H | $G_B$ | 230–235° (dec) | 485 |
| *138 | ![dibenzosuberane] | N | —NMe₂ | H | H | A | 160° | 529 |

-continued
| Example Number | E | X[1] | R[5] | R[6] | R[7] | Prep. Meth. | M.P. (° C.) | Mass Spec. |
|---|---|---|---|---|---|---|---|---|
| *139 | 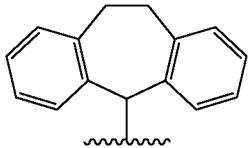 | N | pyridin-3-yl | H | H | A | 145–150° (dec) | 563 |
| *140 | 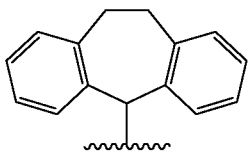 | N | i-Pr | H | H | A | 135° (dec) | 528 |
| 141 | 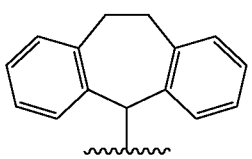 | N | methyl | NO$_2$ | H | % | oil | 545 |
| *142 | 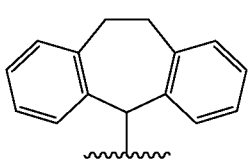 | N | piperazin-1-yl | H | H | A** | 145° | 570 |
| *143 | 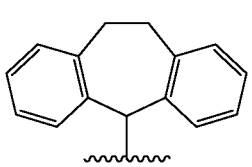 | N | pyridin-4-yl | H | H | A | 156° (dec) | 563 |
| *144 | 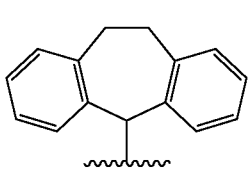 | N | ethyl | H | H | A | 160° (dec) | 514 |
| *145 | 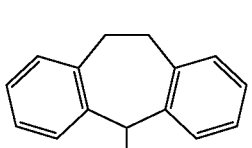 | N | n-butyl | H | H | A | 136° (dec) | 542 |
| *146 | 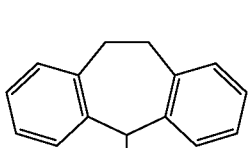 | N | 4-methyl piperazin-2-yl | H | H | A | >165° (dec) | 584 |

-continued

| Example Number | E | X¹ | R⁵ | R⁶ | R⁷ | Prep. Meth. | M.P. (° C.) | Mass Spec. |
|---|---|---|---|---|---|---|---|---|
| 147 | dibenzosuberyl | N | methyl | amino | H | % | 66–68° | 515 |
| 148 | dibenzosuberyl | N | methyl | —NHCO—CH₃ | H | % | glass | 557 |
| 149 | 2-(propylthio)phenyl | N | methyl | H | —CH₂CH=CH₂ | A | hygroscopic solid | 498 |
| *150 | 2-(propylthio)phenyl | N | morpholino | H | H | A | 186° (dec) | 529 |
| *151 | chlorodibenzoxazepinyl | N | —CH₂CHOH—(CH₃)₂ | H | H | G_A | 156–160° (dec) | 594 |
| *152 | chlorodibenzoxazepinyl | N | methyl | H | H | G_A | 152–156° (dec) | 536 |
| *153 | dibenzosuberyl | N | —CONH₂ | H | H | G_A | 160° (dec) | 525 |
| †154 | dibenzosuberyl | N | methyl | H | H | A | 208–210° (dec) | 500 |

-continued

| Example Number | E | X¹ | R⁵ | R⁶ | R⁷ | Prep. Meth. | M.P. (° C.) | Mass Spec. |
|---|---|---|---|---|---|---|---|---|
| 155 | (dibenzocycloheptenyl) | N | morpholino | H | H | A | 142–146° (dec) | 571 |
| *156 | (dibenzocycloheptenyl) | N | —CH₂CHOH—(CH₃)₂ | H | H | A | 149–153° (dec) | 558 |
| 157 | (dibenzocycloheptenyl) | N | methyl | —NHBn | H | % | 138–141° | 605 |
| 158 | —CH(Ph)₂ | N | methyl | Cl | H | A | 70–76° (free base) 234–235° (HCl salt) | |

*R-isomer at propan-2-ol position.
†S-isomer at propan-2-ol position.
**Prepared from 2-(4-trifluoroacetyl-piperazin-1-yl)benzothiazol-7-ol (Preparation 86) with subsequent deacylation at pH 12 during extractive work-up.
% The preparation of this compound is described herein below.

PREPARATION of Examples 141, 147 and 157

The nitration of 7-methoxy-2-methylbenzothiazole was carried out as described for the nitration of benzothiazole (Ward, E. R.; Poesche, W. H.; *J. Chem. Soc.* 1961, 2825). The nitration produces a mixture of 4- and 6-nitrobenzothiazoles which were separated by column chromatography (silica gel, CH₂Cl₂) to give the 7-methoxy-2-methyl-4-nitrobenzothiazole as a white solid (31%).

7-Hydroxy-2-methyl-4-nitrobenzothiazole was prepared from 7-methoxy-2-methyl-4-nitrobenzothiazole by treatment with solid pyridine hydrochloride as described in Preparation 1 (91%).

To 7-hydroxy-2-methyl-4-nitrobenzothiazole (0.88 g, 4.2 mmol) in DMF (5 mL) was added NaH (0.184 g of 60% oil dispersion, 4.6 mmol) portionwise. The reaction was stirred at room temperature for about 30 minutes at which time epibromohydrin (394 μL, 4.6 mmol) was added in one portion and the reaction then heated at about 60° C. To push the reaction towards completion, additional epibromohydrin (400 μL) was added. The reaction was poured into water and extracted with ethyl acetate. The organic extracts were combined, washed with H₂O, dried over Na₂SO₄ and the solvent removed by rotary evaporation. The resulting dark oil (960 mg, 86%) was used without further purification.

The epoxide (0.39 g, 1.5 mmol) and 1-(10,11-dihydro-5H-dibenzo[a,d]cyclohepten-5-yl)piperazine (0.847 g, 3.0 mmol) were dissolved in 1:1 EtOH/dioxane (10 mL) and heated at reflux for about 4 h. The solvent was removed by rotary evaporation and the crude product purified by column chromatography (silica gel, 5% CH₃OH/CH₂Cl₂) to give the piperazinyl alcohol (0.651 g, 79%), [EXAMPLE 141].

This material (650 mg, 1.2 mmols) was dissolved in 1:1 dioxane/CH₃OH (6 mL) to which was added CoCl₂.6H₂O (571 mg, 2.4 mmol) and finally sodium borohydride (454 mg, 12.0 mmol) was added portionwise. The reaction was stirred at room temperature for 2 h. The reaction was filtered and the filtrate concentrated by rotary evaporation. The residue was dissolved in CH₂Cl₂ and washed with H₂O and brine and the organic layer dried over Na₂SO₄. The solvent was removed by rotary evaporation and the crude residue purified by column chromatography (silica gel, 9:1:2 CH₂Cl₂/CH₃OH/hexane) to give the 4-aminobenzothiazole derivative [EXAMPLE 147](125 mg, 20%).

The 4-aminobenzothiazole derivative (57 mg, 0.11 mmol) was added to a suspension of NaBH(OAc)₃ (93 mg, 0.44 mmol) in dichloroethane (1 mL) followed by addition of benzaldehyde (110 μL, 0.11 mmol) and Na₂SO₄. The reaction was stirred at room temperature for about 48 h. The reaction was diluted with CH₂Cl₂, washed with saturated aqueous Na₂CO₃ and brine and dried over Na₂SO₄. The solvent was removed by rotary evaporation and the crude product purified by column chromatography (silica gel, CH₂Cl₂→10% CH₃OH/CH₂Cl₂) to give the product of [Example 157], 1-(4-Benzylamino-2-methyl-benzothiazol-7-yloxy)-3-[4(10,11-dihydro-5H-dibenzo-[a,d]cyclohepten-5-yl)-piperazin-1-yl]-propan-2-ol, as the free base (40 mg, 61%). The hydrochloride salt was formed by dissolving the free base in Et₂O/CHCl₃ and treating with 1N HCl/Et₂O. mp=138–141° C.; MS=605.

PREPARATION of Example 148
N-(7-{3-[4-(10,11,Dihydro-5H-dibenzo[a,d]cyclohepten-5-yl)-piperazin-1-yl]-2-hydroxy-propoxy}-2-methyl-benzothiazol-4-yl)-acetamide To the 4-aminobenzothiazole derivative (compound of Example 147) (0.035 g, 0.07 mmol) dissolved in CH₂Cl₂ (1 mL) was added triethylamine (20 μL, 0.14 mmol), acetic anhydride (20 μL) and catalytic amount of DMAP. The reaction was stirred at room temperature for several hours at which time water was added and the layers separated. The organic layer was dried over $Na_2SO_4$ and evaporated to a yellow oil which was purified by column chromatography.

This bis-acetylated material was treated with KOH/$CH_3OH$ for 24 h. to give the title compound. MS=558.

EXAMPLES 159–163

Compounds of Examples 159–163 having the general formula

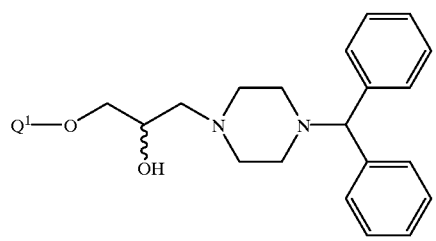

were synthesized according to the methods shown.

| Example Number | $Q^1$ | Prep. Method | Mass Spec. |
|---|---|---|---|
| 159 | | A | 471 |
| 160 | | A | 470 |
| 161 | | A | 485 |
| 162 | | A | 485 |
| 163 | | A | 575 |

EXAMPLES 164–170

Compounds of Examples 164–170 having the general formula

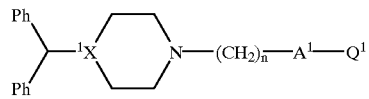

were synthesized according to the methods shown.

| Example Number | $X^1$ | n | —$A^1$—$Q^{1**}$ | Prep. Method | M.P. (° C.) | Mass Spec. |
|---|---|---|---|---|---|---|
| +164 | N | 2 | | D | 67–71.8° | 506 |

-continued

| Example Number | $X^1$ | n | —$A^1$—$Q^1$** | Prep. Method | M.P. (° C.) | Mass Spec. |
|---|---|---|---|---|---|---|
| 165 | CH | 3 | 4-methoxy-2-methyl-1H-benzimidazole | * | 95–103° | 440 |
| 166 | CH | 3 | 4-methoxy-1H-benzotriazole | * | >300° (dec) | 427 |
| +167 | CH | 3 | 4-methoxy-1H-benzimidazole | * | 65–76° | 426 |
| 168 | CH | 3 | 4-methoxy-1-methyl-1H-benzotriazole | * | >300° (dec) | 441 |
| 169 | CH | 3 | 4-methoxy-2-methyl-2H-benzotriazole | * | >300° (dec) | 441 |
| 170 | N | 3 | 6-methoxybenzothiazole | $E_A$ | 136–137° | 444 |

*These compounds were synthesized according to the procedures on the following pages.
+The M.P. reported is for the free base
**$A^1$ is the phenoxy O and it is directly bonded to the methylene group of the general structure shown at the top of the page.

PREPARATION of Examples 164–170

4-Benzhydrylpiperidine hydrochloride (4.20 g, 15.0 mmol) stirred in dioxane (25 mL)/6N. aq.NaOH (2.5 mL) with diisopropylethylamine (2.65 mL) was treated with 3-bromopropyl-(2,3-dinitrophenyl) ether (5.05 g, 16.6 mmol) at about 20° C. for about 16 h followed by about 80° C. for about 3 h. The reaction mixture was concentrated in vacuo and partitioned between EtOAc and 1N NaOH. The organic phase was dried over $MgSO_4$(s), concentrated in vacuo to ≈25 mL and diluted to cloudiness with diisopropyl ether. The product was precipitated as the HCl salt by addition of 1 M HCl in $Et_2O$ (18 mL, 18 mmol). The precipitated crystals of 1-[3-[4-(benzhydryl)piperidin-1-yl] propoxy]-2,3-dinitrophenol were filtered, washed with diisopropyl ether and petroleum ether and dried (6.85 g; LSIMS m/z 476).

The dinitrophenyl amine HCl salt, synthesized in the previous step, (2.02 g, 3.95 mmol) in MeOH (200 ml) was hydrogenated (15–60 psi, 2–20 h) in the presence of 5–10% Pd on carbon catalyst (200 mg). Following removal of catalyst by centrifugation or filtration under a $N_2$(g) atmosphere and removal of solvent in vacuo (30–35° C.) the air-sensitive diaminophenyl intermediate was obtained (>90% purity; 100% recovery; LSIMS m/z 416) and used directly in subsequent reactions.

Benzimidazoles (Examples 165 and 167): The appropriate diaminophenyl intermediate synthesized above was dissolved in excess formic acid (Example 167) or acetic acid (Example 165) (2–5 g/100 mL) and the stirred solution was heated to reflux under dry $N_2$(g) for about 8–16 h. Excess acid was removed in vacuo (30–40° C.) and the residue was partitioned between EtOAc and aqueous 5% $Na_2CO_3$ or 1N NaOH. The organic phase was washed with brine, dried over Na₂SO₄, concentrated in vacuo and chromatographed on silica (10–15% MeOH in EtOAc) to afford the benzimidazole products (55–85% yields) as the free bases.

Benzotriazoles (Example 166): The appropriate diaminophenyl intermediate (1.0 g, 2.57 mmol) was dissolved in 50% aqueous AcOH (50 mL). While stirring vigorously 0.84 M aqueous NaNO₂ (3.1 mL, 2.6 mmol) was added dropwise over 10 min. at 0–5° C. After 15 minutes it was concentrated in vacuo and partitioned between EtOAc and H₂O (with the pH of the aqueous phase adjusted to 9–10). The organic phase was washed with brine, dried over Na₂SO₄, concentrated in vacuo and chromatographed on silica (15% MeOH/EtOAc) to afford the benzotriazole (Example 166) as the free base (60–77% yield; 0.63–0.81 g).

N-Methyl Benzotriazoles (Examples 168 and 169): Benzotriazole free base (from above; 155 mg, 0.36 mmol) in CH₂Cl₂ (2.5 mL) was treated while stirring with etheral diazomethane (2–10 eq.). After about 2 h (10–20° C.) the solvent and excess diazomethane were removed in vacuo and the residue was chromatographed on silica (Chromatotron; 1% conc. NH₄OH; 1.5% MeOH, 97.5% (CHCl₃)) to afford (36%; 57 mg) 2-N-methyl benzotriazole derivative (Example 169) and (15%; 24 mg) 3-N-methyl benzotriazole (Example 168).

EXAMPLES 171–180

Compounds of Examples 171–180 having the general formula

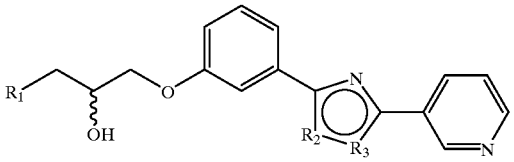

were synthesized according to the methods shown. *The M.P. reported is for the free base.

| Example Number | $R_1$ (=NR$^{101}$R$^{102}$) | $R_2$ | $R_3$ | Prep. Method | M.P. (° C.) | Mass Spec. |
|---|---|---|---|---|---|---|
| 171 | 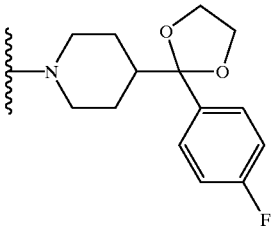 | N | O | A | 192–193° | 547 |
| *172 | 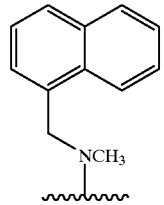 | N | O | A | 125° | 467 |
| 173 | 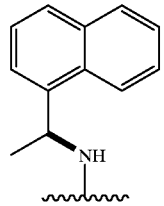 | N | O | A | 119° | 467 |
| 174 | 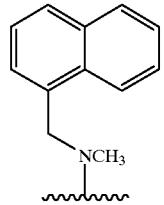 | O | N | A | 115–116° | 467 |

-continued

| Example Number | R₁ (=NR¹⁰¹R¹⁰²) | R₂ | R₃ | Prep. Method | M.P. (° C.) | Mass Spec. |
|---|---|---|---|---|---|---|
| *175 | [1-(naphthalen-1-yl)ethyl]amino | O | N | A | foam | 467 |
| *176 | [(7-methoxy-1,2,3,4-tetrahydronaphthalen-1-yl)methyl]amino | O | N | A | foam | 487 |
| *177 | [(R or S)-1-(naphthalen-1-yl)ethyl]amino | N | O | A | foam | 467 |
| *178 | [(S or R)-1-(naphthalen-1-yl)ethyl]amino | O | N | A | foam | 467 |
| *179 | 4-(hydroxydiphenylmethyl)piperidin-1-yl | N | O | A | 86–89° | 563 |

-continued

| Example Number | R₁ (=NR¹⁰¹R¹⁰²) | R₂ | R₃ | Prep. Method | M.P. (° C.) | Mass Spec. |
|---|---|---|---|---|---|---|
| *180 | Ph-C(OH)(Ph)-piperidin-4-yl | O | N | A | 82–83 | 563 |

EXAMPLES 181–193

Compounds of Examples 181–193 having the general formula

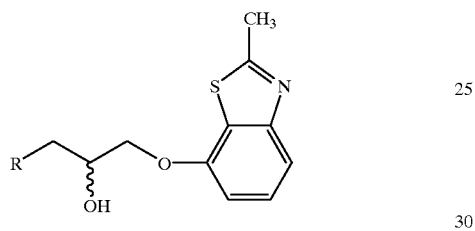

were synthesized according to Method $G_A$ using the free base or salt form of the amines and 3.0 equivalents of Amberlite IRA-400 resin.

| Example Number | R (=NR¹⁰¹R¹⁰²) Bonded through the amino group | HPLC Ret. Time (min.) | LC-MS (MH⁺) |
|---|---|---|---|
| 181 | Cyclohexylamino | 2.83 | 321 |
| 182 | 1-Amino-4-methylcyclohexane | 3.05, 3.12 | 335 |
| 183 | 1-Amino-3-methylcyclohexane | 3.06 | 335 |
| 184 | 1-Amino-4-t-butylcyclohexane | 3.81 | 377 |
| 185 | 1-Amino-1-phenylcyclohexane | 3.45 | 397 |
| 186 | Diphenylmethylamino | 3.60 | 405 |
| 187 | 1-amino-1,2,3,4-tetrahydronaphthalene | 3.15 | 369 |
| 188 | 1-aminoindane | 3.02 | 355 |
| 189 | 3-(aminomethyl)benzo[b]thiophene | 3.69 | 385 |
| 190 | 1-amino-1,2-diphenylethane | 3.59 | 419 |
| 191 | 2-amino-4-phenylbutane | 4.21, 4.31 | 371 |
| 192 | 4-(2-phenylethyl)piperazin-1-yl | 3.05 | 412 |
| 193 | bis-fluorophenyl carboline | 4.48 | 508 |

EXAMPLES 194–222

Compounds of Examples 194–222 having the general formula

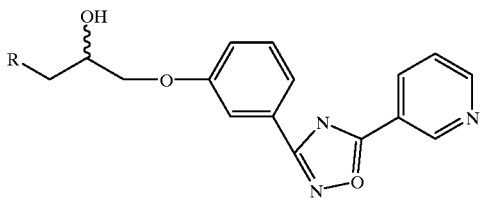

were synthesized according to the methods shown.

| Example Number | R (=NR$^{101}$R$^{102}$) Bonded through the amino group | HPLC Ret. Time (min.) | Mass Spec. (MH$^+$) |
|---|---|---|---|
| 194 | 4-(3-hydroxy-3,3-diphenylpropyl)piperazin-1-yl | 3.99 | 592 |
| 195 | 4-[2-(trifluoromethyl)benzyl]piperazin-1-yl | 4.11 | 540 |
| 196 | *(structure)* | 4.05 | 638 |
| 197 | *(structure)* | 3.88 | 491 |
| 198 | *(structure)* | 3.91 | 689 |
| 199 | *(structure)* | 3.83 | 569 |
| 200 | *(structure)* | 3.53 | 547 |
| 201 | N,N-Bis-[2-(3,4-dimethoxyphenyl)ethyl]amino | 3.97 | 641 |
| 202 | 4-(3-Trifluoromethylphenyl)piperazin-1-yl | 3.88 | 526 |
| 203 | *(structure)* | 3.20 | 489 |
| 204 | *(structure)* | 3.54 | 559 |
| 205 | *(structure)* | 4.23 | 555 |
| 206 | 1-Amino-1-benzylcyclopentane | 3.85 | 471 |
| 207 | *(structure)* | 3.53 | 580 |
| 208 | *(structure)* | 3.41 | 503 |
| 209 | *(structure)* | 3.25 | 535 |
| 210 | *(structure)* | 3.20 | 528 |
| 211 | *(structure)* | 4.08 | 507 |

-continued

| Example Number | R (=NR¹⁰¹R¹⁰²) Bonded through the amino group | HPLC Ret. Time (min.) | Mass Spec. (MH⁺) |
|---|---|---|---|
| 212 | Ph–CH(NH)–CH₂–C(OH)(Ph)(CH₂Ph) | 5.04 | 627 |
| 213 | 1-hydroxy-1-(aminomethyl)-1,2,3,4-tetrahydronaphthalene | 3.54 | 473 |
| 214 | 4-MeO-C₆H₄–CH(NH)–CH(OH)(Ph)₂ | 4.83 | 629 |
| 215 | trans-2-phenylcyclohexylamine | 3.95 | 471 |
| 216 | 6-methoxy-1-hydroxy-1-(aminomethyl)-1,2,3,4-tetrahydronaphthalene | 3.53 | 503 |
| 217 | 6-methoxy-1-(aminomethyl)-1,2,3,4-tetrahydronaphthalene | 3.87 | 487 |
| 218 | 7-methoxy-1-(aminomethyl)-1,2,3,4-tetrahydronaphthalene | 3.86 | 487 |

-continued

| Example Number | R (=NR¹⁰¹R¹⁰²) Bonded through the amino group | HPLC Ret. Time (min.) | Mass Spec. (MH⁺) |
|---|---|---|---|
| 219 | norbornenyl-(4-CF₃-phenyl)-NH | 4.32 | 549 |
| 220 | 1-amino-4-(3-CF₃-phenyl)-1,2,3,4-tetrahydronaphthalene | 4.74 | 587 |
| 221 | norbornyl-(4-CF₃-phenyl)-NH | 4.45 | 551 |
| 222 | norbornyl-phenyl-NH | 3.99 | 483 |

EXAMPLES 223–234

Compounds of Examples 223–234 having the general formula

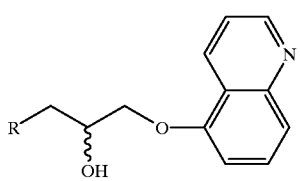

were synthesized according to Method A.

| Example | R (=NR¹⁰¹R¹⁰²) Bonded through the amino | RP-HPLC Retention Time (min.) | LC-MS (MH⁺) | MP (° C.) |
|---|---|---|---|---|
| 223 | (3,4-dibenzyl-8-azabicyclo[3.2.1] with ketone, N-linked) | N.T. | 507 | >175° C. |
| 224 | 1-phenyl-1,2,3,4-tetrahydronaphthalen-4-yl-N(CH₃)- | 4.60 min. | 439 | 162° C. |
| 225 | 1-phenyl-1,2,3,4-tetrahydronaphthalen-4-yl-N(CH₃)- | 4.81 min. | 439 | 175° C. |
| 226 | 1-phenyl-1,2,3,4-tetrahydronaphthalen-4-yl-N(CH₃)- | N.T. | 439 | 159° C. |
| 227 | 3-(benzyl)pyrrolidin-1-yl | N.T. | 363 | 96.0 |

-continued

| Example | R (=NR¹⁰¹R¹⁰²) Bonded through the amino | RP-HPLC Retention Time (min.) | LC-MS (MH⁺) | MP (° C.) |
|---|---|---|---|---|
| 228 | 3-(diphenylmethoxy)piperidinyl (one stereoisomer) | 4.64 | 469 | 115 |
| 229 | 3-(diphenylmethoxy)piperidinyl (other stereoisomer) | 4.64 | 469 | N.T. |
| 230 | 3-(cyano(diphenyl)methyl)pyrrolidinyl | N.T. | 464 | 111 |
| 231 | 3-(diphenylmethyl)pyrrolidinyl (mixture) | N.T. | 439 | 125 |
| 232 | 3-(diphenylmethyl)pyrrolidinyl (one stereoisomer) | N.T. | 439 | 119 |
| 233 | 3-(diphenylmethyl)pyrrolidinyl (other stereoisomer) | N.T. | 439 | 116 |
| 234 | 1-(methylamino)-3-phenyl-indanyl | N.T. | 425 | 141 |

N.T. = Not taken.

EXAMPLES 235–258
Compounds of Examples 235–258 having the general formula
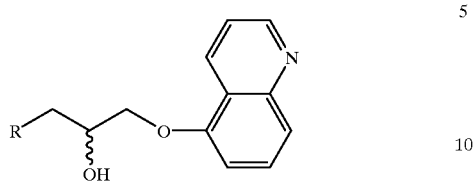
were synthesized according to Method B.
| Example | R (=NR^101 R^102) Bonded through the amino | RP-HPLC Retention Time (min.) | LC-MS (MH+) |
|---|---|---|---|
| 235 | | 2.93 | 363 |
| 236 | | 3.21 | 387 |
| 237 | | 3.10 | 375 |
| 238 | | 3.37 | 401 |
| 239 | | 3.25 | 389 |
| 240 | | 3.73 | 457 |
| 241 | | 3.16 | 377 |

-continued

| Example | R (=NR$^{101}$R$^{102}$) Bonded through the amino | RP-HPLC Retention Time (min.) | LC-MS (MH$^+$) |
|---|---|---|---|
| 242 | | 3.16 | 377 |
| 243 | | 3.62 | 455 |
| 244 | | 3.26 | 447 |
| 245 | | 3.32 | 595 |
| 246 | | 3.29 | 433 |
| 247 | | 3.63 | 461 |
| 248 | | 3.44 | 421 |

-continued
| Example | R (=NR<sup>101</sup>R<sup>102</sup>) Bonded through the amino | RP-HPLC Retention Time (min.) | LC-MS (MH<sup>+</sup>) |
|---|---|---|---|
| 249 | 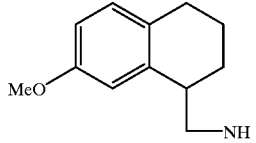 | 3.19 | 393 |
| 250 | 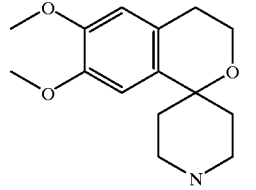 | 2.89 | 465 |
| 251 | 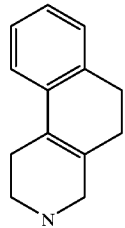 | 3.10, 3.27 (~1:1 diastereomers) | 387 |
| 252 | 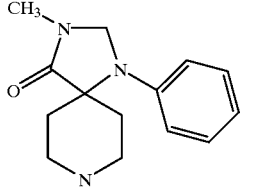 | 2.93 | 447 |
| 253 | 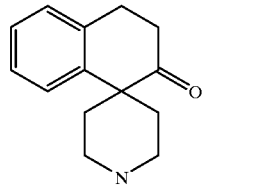 | 3.05 | 417 |
| 254 | 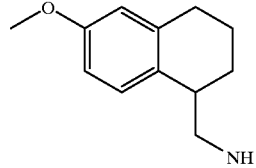 | 3.09 | 393 |
| 255 | 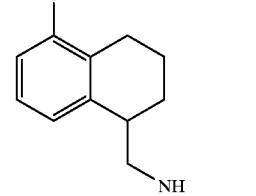 | 3.21 | 393 |

-continued
| Example | R (=NR¹⁰¹R¹⁰²) Bonded through the amino | RP-HPLC Retention Time (min.) | LC-MS (MH⁺) |
|---|---|---|---|
| 256 | ![structure] | 2.86 | 409 |
| 257 | ![structure] | 2.81 | 397 |
| 258 | ![structure] | 3.91 | 469 |
EXAMPLES 259–261
Compounds of Examples 259–261 having the general formula
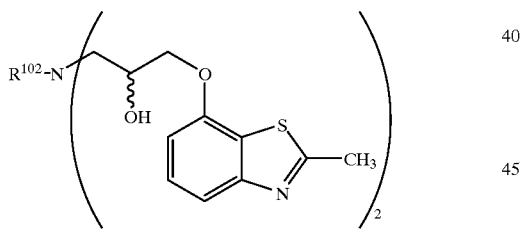
were synthesized according to the methods shown.
| Example Number | R¹⁰² | Prep. Method | MP (° C.) | Anal. RP-HPLC Retention Time | LC-MS (MH⁺) |
|---|---|---|---|---|---|
| *259 | | G$_A$ | 75° C. | 5.09 min. | 604 |

-continued

| Example Number | R$^{102}$ | Prep. Method | MP (° C.) | Anal. RP-HPLC Retention Time | LC-MS (MH$^+$) |
|---|---|---|---|---|---|
| *260 | (6-methoxy-tetrahydronaphthalen-1-yl)methyl structure | G$_A$ | 93° C. | 4.97 min. | 634 |
| 261 | norbornenyl-phenyl structure | G$_A$ | N.T. | 2 diastereomers 4.75 min. 4.90 min. | 628 628 |

*The M.P. reported is for the free base.
N.T. = Not taken.

EXAMPLE 262

5-[2-(4-Benzhydryl-piperidin-1-yloxy)ethoxy] quinoline

To 0.13 g (3.25 mmol) of NaH (60% oil dispersion) in 2 ml of DMF at room temperature, was added portionwise 0.785 g (2.94 mmol) of N-hydroxybenzhydrylpiperidine. After bubbling had stopped, stirring was continued for an additional 15 minutes, 0.741 g (2.94 mmol) of 5-(2-bromoethyloxy)quinoline was added. The mixture was stirred for about 10 minutes and heated to reflux for about 6 hours. The resulting black solution was cooled to room tempereature, poured over ice and extracted with 1:1 Et$_2$O/EtOAc. These were dried over MgSO$_4$(s) filtered and concentrated in vacuo to give a black oil, 1.18 g. This material was chromatographed on silica gel using a gradient of 2 to 4% MeOH/CHCl$_3$ as eluent, to yield 60 mg of a yellow oily solid. This material was dissolved in minimal CHCl$_3$, diluted 4x with dry Et$_2$O and precipitated as the monohydrochloride salt by dropwise addition of 1 equivalent of 1 molar HCl in Et$_2$O. The resulting white solid was filtered and dried in vacuo to yield 65 mg of the desired product, LSIMS, MH$^+$ at 439, analytical RP-HPLC, 6.95 min.

EXAMPLE 263

1-(4-Benzhydryl-piperazin-1-yl)-3-(2-pyridin-3-yl-8-oxa-1-thia-3-aza-cyclopenta[a]inden-7-yloxy)-propan-2-ol 3-Oxo-7-methoxybenzofuran (500 mg, 3.29 mmol) was dissolved in CCl$_4$ (15 mL) and treated with a solution of Br$_2$ (0.17 mL, 3.29 mmol) in CCl$_4$ (5 mL). After about 10 min. the solvent was removed in vacuo. The resulting oil was dissolved in acetone (20 mL), treated with thioisonicotinamide (454 mg, 3.29 mmol) and refluxed for about 18 h. The dark mixture was cooled and CH$_2$Cl$_2$ was added to precipitate product which was filtered and chromatographed on silica (R$_f$ 0.25, 8% MeOH/CH$_2$Cl$_2$) to provide 30 mg of chromatographically pure material. This anisole product was converted to the phenol by the method described in Preparation 16 below. The glycidyl ether of this material was prepared according to the method described in Preparation 69 below. Finally the title compound was prepared according to Method A as described in Example 2 above. The final product was purified by column chromatography on silica gel eluting with 5% MeOH/CH$_2$Cl$_2$ to provide 12.3 mg of a solid which was triturated with Et$_2$O/hexanes to provide a yellow powder. (R$_f$ 0.41, 10% MeOH/CH$_2$Cl$_2$). FAB MS, 563.2.

EXAMPLE 264 cis-7-{4-[4-(10,11-Dihydro-5H-dibenzo[a,d] cyclohepten-5-yl)-piperazin-1-yl]-but-2-envioxy}-2-methyl-benzothiazole The title compound was prepared according to Method G$_A$ from cis-7-(3-chloroallyloxy)-2-methyl-benzothiazole and 1-(10,11-dihydro-5H-dibenzo[a,d]cyclohepten-5-yl) piperazine. mp 114° C.; LSIMS m/z 496. The cis-7-(3-chloro-allyloxy)-2-methyl-benzothiazole was prepared by Method IV, with cis-1,4-dichloro-2-butene as the alkylating agent.

EXAMPLE 265 trans-7-{4-[4-(10,11-Dihydro-5H-dibenzo[a,d] cyclohepten-5-yl)-piperazin-1-yl]-but-2-enyloxy}-2-methyl-benzothiazole The title compound was prepared according to Method G$_A$ from trans-7-(3-chloro-allyloxy)-2-methyl-benzothiazole and 1-(10,11-dihydro-5H-dibenzo[a,d]-cyclohepten-5-yl)piperazine. mp 151–152° C.; LSIMS m/z 496. The trans-7-(3-chloroallyloxy)-2-methyl-benzothiazole was prepared by Method IV with trans-1,4-dichloro-2-butene as the alkylating agent.

EXAMPLE 266

1-[4-(10,11-Dihydro-5H-dibenzo[a,d]cyclohepten-5-yl)-piperazin-1-yl]-2-methyl-4-(2-methylbenzothiazol-7-yloxy-butan-2-ol The title compound was prepared according to Method A from 2-methyl-7-[2-(2-methyl-oxiranyl)-ethoxy]

benzothiazole and 1-(10,11-dihydro-5H-dibenzo[a,d] cyclohepten-5-yl)piperazine. mp 137–138° C.; LSIMS m/z 528. The 2-methyl-7-[2-(2-methyl-oxiranyl)-ethoxy] benzothiazole was prepared by the method described in Preparation 95.

EXAMPLE 267

2-Methyl-4-(2-methyl-benzothiazol-7-yloxy)-1-[4-(2-propylsulfanylphenyl)-piperazin-1-yl]-butan-2-ol hydrochloride The title compound was prepared according to Method A from 2-methyl-7-[2-(2-methyl-oxiranyl)-ethoxy] benzothiazole and 1-(2-thiopropylphenyl)piperazine. mp 129–130° C.; LSIMS m/z 486. The 2-methyl-7-[2-(2-methyl-oxiranyl)-ethoxy]benzothiazole was prepared by the method described in Preparation 95.

EXAMPLE 268

2-[4-(10,11-Dihydro-5H-dibenzo[a,d]cyclohepten-5-yl)-piperazin-1-yl]-6-(2-methyl-benzothiazol-7-yloxy)-cyclohexanol The title compound was prepared according to Method A from 2-methyl-7-(7-oxa-bicyclo[4.1.0]hept-2-yloxy)-benzothiazole and 1-(10,11-dihydro-5H-dibenzo[a,d]-cyclohepten-5-yl)piperazine with dioxane/toluene (2:1) as the solvent. mp 207° C. (decomposition); LSIMS m/z 540. The 2-methyl-7-(7-oxa-bicyclo[4.1.0]hept-2-yloxy)-benzothiazole was prepared according to Method IV using THF as the solvent and 4-bromo-2-oxa-bicyclo[4.1.0] heptane as the alkylating agent.

EXAMPLE 269

1-(1-Benzhydryl-azetidin-3-ylamino)-3-(2-methyl-benzothiazol-7-yloxy)-propan-2-ol The title compound was prepared according to Method A from 2-methyl-7-(oxiranyl-2-ylmethoxy)benzothiazole and 3-amino-1-benzhydrylazetidine with dioxane/ethanol (1:1) as the solvent. mp 55° C.; LSIMS m/z 460. The 3-amino-1-benzhydrylazetidine was prepared as described in Preparation 96.

The following section describes the preparation of starting materials for use in synthesizing the compounds of this invention. Other starting materials not described in the following section are available commercially or through literature methods well-known to those skilled in the art.

PREPARATION 1

2-Methyl-benzothiazol-7-ol m-Anisidine (12.6 g, 0.102 moles) and ethyl dithioacetate (12.3 g, 0.102 moles) were combined with vigorous stirring and heated to about 65° C. while flushing slowly with $N_2(g)$. After 5 hours, additional ethyl dithioacetate (1.0 g) was added and stirring under $N_2(g)$ at ambient temperature was continued. The mixture was diluted with EtOAc (200 mL) and the organic solution was washed with 1N HCl (3×50 mL), and brine (50 mL), dried over $MgSO_4$, filtered and concentrated in vacuo to provide a dark yellow solid (13.2 g). This thioamide may be used directly for the following reaction or chromatographed to purity on silica (5–20% EtOAc/hexanes).

A mixture of the thioamide from above (1.00 g, 5.52 mmol) and NaOH (1.63 g, 40.8 mmol) dissolved in $H_2O$ (25 mL) and MeOH (2 mL) was added dropwise with stirring to a partial suspension of $K_3Fe(CN)_6$ (6.0 g, 18.2 mmol) in $H_2O$ (15 mL) at about 60° C. The mixture was stirred for 2 hours at about 60° C. and then $K_2CO_3$ (4.0 g, 29 mmol) was added and stirring was continued for 1 hour at 50–60° C. After cooling to room temperature the mixture was extracted with $Et_2O$ (3×25 mL), and the organic extracts were dried over $Na_2SO_4$ and concentrated in vacuo. The residue (800 mg) was chromatographed on silica to separate the less polar 7-methoxy-2-methyl-benzothiazole (440 mg, 44%) from the 5-methoxy isomer.

7-Methoxy-2-methyl-benzothiazole (400 mg, 2.23 mmol) was mechanically mixed with solid pyridine hydrochloride (6.00 g, 52 mmol) and then heated to 160–170° C. in a sealed vessel for 16 hours. Water (40 mL) was added to the warm mixture, the pH was adjusted to neutrality with $NaHCO_3$ and the mixture was extracted with 1:1 $CHCl_2/CHCl_3$ (4×10 mL). The pooled organic extracts were dried over $MgSO_4$, filtered, and concentrated in vacuo to provide 2-methyl-benzothiazol-7-ol as a waxy yellow solid. (260 mg; GC-MS m/z 165).

PREPARATION 2

2-(Pyridin-2-yl)benzothiazol-7-ol and 2-(pyridin-2-yl)benzothiazol-5-ol

The title compounds were prepared as described by T. Hisano, M. Ichikawa, K. Tsumoto and M. Tasaki in Chem. Pharm. Bull. 30, 2996–3004 (1982). m-Anisidine (28.1 mL, 0.25 mol), 2-picoline (24.7 mL, 0.25 mol) and sulfur (20.1 g) were heated under $N_2(g)$ atmosphere to about 170° C. for about 10 h. After cooling EtOH (500 mL) was added and the mixture was refluxed for 30 min. and concentrated in vacuo. The resulting yellow solid residue was extracted with 10% aqueous KOH (500 mL). Upon cooling the KOH extract to about 20° C., the 5-methoxy-2-(pyridin-2-yl)-benzothiazole crystallized. This material was recovered by filtration, pooled with hot KOH-insoluble solids, and recrystallized from EtOH (19.6 g; m.p. 132–134° C.; GC-MS m/z 242) before demethylation to the 2-(pyridin-2-yl)benzothiazol-5-ol (18.2 g; m.p. 267–273° C.; GC-MS m/z 228) utilizing pyridine.HCl at about 170° C. as described in Preparation 1.

The aqueous KOH filtrate was neutralized with 3N HCl causing the thioanilide to separate. This material was recovered by extraction into EtOAc. Organic phases were dried over $Na_2SO_4(s)$ and concentrated in vacuo to afford ~6.5 g of crude thioamide which was oxidatively cyclized to a mixture of the 5-methoxy and 7-methoxy-2-(pyridin-2-yl) benzothiazoles with $K_3Fe(CN)_6$ as outlined in Preparation 1 above. The reaction mixture was extracted with $CHCl_3$ (4×50 mL), and pooled extracts were dried over $Na_2SO_4(s)$ before concentrating in vacuo. The residue was flash chromatographed on silica using 25% EtOAc/hexanes to separate the 7-methoxy isomer (330 mg; GC-MS m/z 242) from the 5-methoxy isomer. Demethylation was again performed utilizing pyridine.HCl at about 170° C. to afford 2-(pyridin-2-yl)benzothiazol-7-ol (274 mg; GC-MS m/z 228).

PREPARATION 3

7-Hydroxybenzothiazole

The title compound was prepared as a mixture (60/40) with the 5-hydroxy isomer in the deprotection of 2-carbamoyl-7-methoxybenzothiazole (obtained in Preparation 4 below) with pyridine.HCl, according to the method described in Preparation 1. The mixture of the 5- and 7-hydroxybenzothiazoles was used directly in the preparation of the isomeric glycidyl ethers which were readily separable by chromatography on silica (2% $CH_3CN$/ $CH_2Cl_2$).

PREPARATION 4

2-Cyano-7-hydroxybenzothiazole and 2-Carbamoyl-7-hydroxybenzothiazole

The title compounds were prepared according to the method of E. H. White and H. Worther, J. Org. Chem. 31, 1484–1488 (1966). A solution of KOH (12.2 g) in EtOH (40 mL) was saturated with $H_2S(g)$ and an equal volume of KOH (12.2 g) in EtOH (40 mL) was added. To this solution in a 500 mL round-bottomed flask equipped with a reflux condensor was added trichloroacetamide (15.0 g, 92.4 mmol) in EtOH (80 mL). Following the ensuing exothermic reaction the deep red solution was warmed to about 50° C. for about 20 min., cooled to about 20° C. and a freshly prepared neutralized (with $K_2CO_3$) solution of chloroacetic acid in $H_2O$ (80 mL) was added. After 30 min., the deep red solution of carbamoylthiocarbonylthioacetic acid was filtered to remove precipitated KCl(s), and m-anisidine (7.54 mL) was added to the filtrate. The mixture was stirred at about 20° C. for about 4½ days with a slow flush of $N_2(g)$ through the vessel ($H_2S(g)$ evolved). The solution was concentrated in vacuo to 200 mL, $H_2O$ (400 mL) was added, and the mixture was warmed to dissolve all materials. Slow cooling to about 20° C. afforded 3-methoxythiooxanilamide (4.5 g, m.p. 135° C.) as yellow needles. This material (4.48 g, 21.3 mmol) was dissolved in $H_2O$ (100 mL) with NaOH (6.30 g) and added dropwise with stirring at about 20° C. to $K_3Fe(CN)_6$ (23.1 g) in $H_2O$ (60 mL). After about 2 h the reaction mixture was cooled to about 10° C. for about 30 min., and the brown precipitate containing a 1:1 mixture of 2-carbamoyl-5- and 7-methoxybenzo-thiazoles (1.96 g) was recovered by filtration, and used below (and in Preparation 3) without further purification. This product (1.46 g, 7.0 mmol) was dissolved in dry pyridine (27 mL), cooled to about −10° C. and treated dropwise over about 10 min. with $POCl_3$ (1.7 mL). After stirring for about 2 h at about 20° C., cyclohexane (215 mL) was added followed by $H_2O$ (150 ml). Phases were separated and the aqueous phase was washed with cyclohexane (3×80 mL). Organic phases were pooled, dried over $MgSO_4(s)$ and concentrated to afford a yellow oily solid (1.19 g) which was flash chromatographed on silica (25% acetone/hexanes) to afford a yellow crystalline solid (1.09 g) containing a 1:1 mixture of 2-cyano-5-methoxybenzothiazole and the 7-methoxy isomer. This material was demethylated using pyridine.HCl at about 180° C. for about 6 h as described in Preparation 1 and the recovered products were flash chromatographed on silica (2% $CH_3CN/CH_2Cl_2$) to afford 2-cyano-7-hydroxybenzothiazole (448 mg, m.p. 225° C.) as the first eluting isomer and 2-cyano-5-hydroxybenzothiazole (370 mg, m.p. 194° C.) as the later.

PREPARATION 5

4-Hydroxy-2,1,3-benzothiodiazole

4-Amino-2,1,3-benzothiodiazole (5.00 g, 33.0 mmol) was added to a solution of $KHSO_4$ (92.1 g, 0.676 moles) in $H_2O$ (120 mL) at about 100° C. followed by $NaHSO_3$ (24.0 g, 0.231 moles). When the vigorous bubbling ceased, the solution was brought to reflux under $N_2(g)$ for 72 hours. The mixture was cooled to about 22° C., the pH was adjusted to 7–8, and the volume of the mixture was increased to 500 mL to dissolve the salts. Multiple extractions with 1:1 $CHCl_3$/ $CH_2Cl_2$ (7×150 mL), followed by drying of the organic phases over $Na_2SO_4$ and concentration in vacuo afforded a reddish-brown residue (4.51 g; >90% purity) which was chromatographed on silica in 20→30% acetone/hexane, to yield 3.90 g of pure product.

PREPARATION 6

2-Methylamino-3-nitrophenol

The title compound was prepared from 2-amino-3-nitrophenol according to a procedure adapted from Tet. Lett. 23, 3315 (1982). 2-Amino-3-nitrophenol (7.7 g, 50 mmol) in dry THF (20 mL) was treated dropwise with formic-acetic anhydride (130 mmol) in THF (10 mL) at about −5° C. under $N_2(g)$. After stirring 3 hours the mixture was concentrated in vacuo to a viscous oil which was redissolved in THF (12 mL) and treated dropwise with 2M borane-dimethylsulfide in THF (63 mL) at about −5° C. When the addition was complete the mixture was heated to reflux (2 hours), cooled in ice and quenched with MeOH (20 mL). After stirring for 1 hour at about 22° C., anhydrous HCl was bubbled into the solution to acidity it to about pH 2. The mixture was refluxed for 1 hour and concentrated in vacuo. The residue was dissolved in $H_2O$, neutralized with conc. $NH_4OH$ and cooled (16 hours) to produce a dark brown solid. This wet material was dissolved in $CHCl_3$, dried over $Na_2SO_4$ and concentrated in vacuo to afford a red-brown solid (6.72 g; >95% purity) which was used directly in the syntheses of 3-methylbenzimidazol-4-ol and 3-methylbenzotriazol-4-ol (below).

PREPARATION 7

3-Methyl-1,2,3-benzotriazol-4-ol

2-Methylamino-3-nitrophenol (2.50 g, 14.9 mmol) in MeOH (200 mL) with HOAc (0.5 mL) was hydrogenated (40 psi, 2 hours) in the presence of 10% Pd on carbon (250 mg). Following removal of the catalyst by filtration the solution was concentrated in vacuo. The residue was resuspended in $H_2O$ (30 mL), and 3N HCl (10 mL) was added dropwise while stirring at 0–5° C., immediately followed by 1.1M $NaNO_2$ (15 mL, 16.5 mmol) in $H_2O$ dropwise over 20 minutes. After 30 minutes at about 22° C., the mixture was recooled to about 5° C., and the pH adjusted to about 6 with conc. $NH_4OH$. The resulting solution was extracted with EtOAc (3×20 mL). The pooled organic extracts were dried over $Na_2SO_4$ and concentrated to yield a dark red-brown solid (2.23 g) which was chromatographed on silica (50→90% EtOAc/hexanes) to afford 1.26 g of pure product as a tan solid (GC/MS m/z 149).

PREPARATION 8

3-Methyl-3H-benzoimidazol-4-ol

2-Methylamino-3-nitrophenol (1.00 g, 5.98 mmol) in MeOH (100 mL) with HOAc (0.22 mL) was hydrogenated (50 psi) for 2 hours over 10% Pd on carbon (186 mg). The catalyst was removed by filtration and the filtrate concentrated in vacuo. The residue was dissolved in formic acid and refluxed for 17 hours under $N_2(g)$. Excess acid was removed in vacuo, and the residue was taken up in 5% MeOH in EtOAc and washed with saturated aqueous $NaHCO_3$ and brine. The organic phase was dried over $Na_2SO_4$ and concentrated in vacuo. The residue was taken up in 5% MeOH in EtOAc and washed with saturated aqueous $NaHCO_3$ and brine. The organic phase was dried over Na$_2$SO$_4$ and concentrated in vacuo to yield a red-brown solid which was chromatographed on silica (50–100% EtOAc/hexanes). The desired product (GC/MS m/z 148) was obtained as a yellow solid, 0.748 g; 84%.

PREPARATION 9

2-, 3- or 4-[(5-Pyridinyl)-[1,2,4]oxadiazol-3-yl)] phenols

The 2- and 4-pyridoaminoximes were prepared from the corresponding cyanopyridines and hydroxylamine described for 3-pyridoaminoxime in Preparation 58 below. The 2-, 3- and 4-[3-(2-methoxyphenyl)-[1,2,4]oxadiazol-5-yl] pyridines were

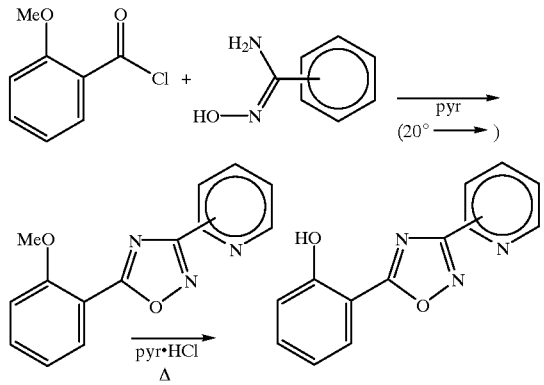

prepared by reaction of the appropriate pyridoaminoxime with o-anisoyl chloride in pyridine (20° C.→reflux) according to Preparation 62 below. Deprotection to yield the 2-, 3- or 4-(5-pyridinyl-[1,2,4]oxadiazol-3-yl)phenol was effected by heating a mixture of the methoxy derivative (from above) with 10 parts pyridine.HCl(s) at about 160° C. for 6–16 hours. The melt was poured into H$_2$O (100–150 parts) with stirring and the precipitated product was filtered and dried in vacuo.

PREPARATION 10

2-(Oxazol-2-yl)-phenol

2-Benzyloxybenzamide (2.0 g, 8.8 mmol) was heated to about 130° C. in bromoacetaldehyde dimethylacetal (10 mL, 85 mmol) under N$_2$(g) for 3.5 hours. Although pure 2-(2-benzyloxyphenyl)oxazole could be obtained by recrystallization from CHCl$_3$/CCl$_4$, the entire mixture was usually directly hydrogenated using 10% Pd on carbon (600 mg) at 40 psi of H$_2$ in 1% HOAc in MeOH (100 mL). Following removal of catalyst by filtration and concentration of the filtrate in vacuo the residue was chromatographed on silica (10→5% acetone/hexanes) to afford 2-(oxazol-2-yl)phenol (860 mg; GC-MS m/z 161 (M$^+$)).

PREPARATION 11

2-(Thiazol-2-yl)phenol

The title compound was prepared according to the method in Z. Naturforsh. 376, 877–880 (1982) or Helv. Chim. Acta 36, 886–890 (1953). o-Cyanophenol (55 mmol, 6.55 g) in EtOAc (160 mL) was treated with diethyl dithiophosphate (9.15 mL, 55 mmol) and HCl(g) was bubbled into the stirred solution at a moderate rate for about 45 min. without external cooling. After stirring at about 20° C. under N$_2$(g) for about 16 h., excess HCl was removed by N$_2$(g) sparge and saturated aqueous Na$_2$CO$_3$ (100 mL) was added carefully with stirring. The organic phase was separated and washed (3×) with saturated Na$_2$CO$_3$ until no further orange color resulted in the aqueous phases. The organic phase was dried over Na$_2$SO$_4$(s) and concentrated in vacuo. An orange crystalline impurity (~3.0 g; m.p. 215° C., EI-MS m/z 255) precipitated upon addition of ether and was removed by filtration. The filtrate was concentrated in vacuo and recrystallized from Et$_2$O/hexanes to afford 2.9 g (m.p. 117° C.; GC-MS m/z 153) of the desired thioamide. This material (2.0 g, 13 mmol) was dissolved in EtOH (5 mL) and α-bromoacetaldehyde dimethyl acetal (1.55 mL, 13 mmol) was added. The mixture was refluxed under N$_2$(g) atmosphere for 3.5 h. and Et$_2$O (15 mL) was added to complete the precipitation of the 2-(thiazol-2-yl)phenol as its hydrobromide salt which was recrystallized from MeOH/CHCl$_3$/Et$_2$O to produce 1.55 g of pure HBr salt (LSIMS m/z 178 (MH$^+$)). This material could be alkylated directly if an extra equivalent of base was included to neutralize the HBr, or it could be free-based by extraction from saturated aqueous NaHCO$_3$ with Et$_2$O followed by drying over Na$_2$SO$_4$(s) and concentration of etheral phases in vacuo.

PREPARATION 12

2-(Thiazol-4-yl)phenol o-(Bromoacetyl)phenyl acetate (5.0 g, 19.5 mmol) was treated with crude thioformamide (filtrate concentrated in vacuo from reaction of P$_2$S$_5$ (1.1 eq.) and (25 mmol) formamide in THF (30–40° C., 5 hours)) in refluxing acetone (60 mL). After 16 hours the reaction mixture was cooled to about 10° C. and the precipitated HBr salt of 2-(thiazol-4-yl)phenol was recovered. 31%, 1.50 g, LSIMS m/z=178 (MH$^+$).

PREPARATION 13

2-(2-Methylthiazol-4-yl)phenol

The title compound was prepared according to the method described in Preparation 12 but utilizing pure thioacetamide rather than crude thioformamide. Yield: 65% as the HBr salt; LSIMS m/z 192 (MH$^+$).

PREPARATION 14

2-[2-(Pyridin-3-yl)thiazol-4-yl]phenol o-(Bromoacetyl)phenyl acetate (2.57 g, 10 mmol) in dry acetone (30 mL) was treated with thionicotinamide (1.38 g, 10 mmol). The mixture was refluxed 16 hours, cooled to about 20° C. at which point a precipitate formed (2.46 g). The precipitate was filtered and dried in vacuo. The precipitate was dissolved in MeOH (50 mL) and treated with 10% NaOH in H$_2$O (20 mL) for 1 hour at about 20° C. to hydrolyze the acetate ester. The pH was adjusted to neutrality with 6N HCl while chilling on ice/H$_2$O and the volume was reduced to about 35 mL in vacuo. After cooling to about 4° C., an orange solid precipitate formed, which was removed by filtration and dried in vacuo to constant mass to yield 36–50% product (LSIMS m/s 254 (MH$^+$)).

PREPARATION 15

2-[(Thiazol-2-yl)oxy]phenol o-Benzyloxyphenol (7.5 g, 37.5 mmol) in dry DMF (60 mL) was treated with Me$_4$N$^+$OH$^-$.5H$_2$O (37.5 mmol, 6.8 g)

followed by 2-bromothiazole (6.15 g, 37.5 mmol). The stirred solution was heated to about 100° C. under $N_2(g)$ for 16 hours. The mixture was cooled in ice and crystalline, $H_2O$-soluble $Me_4N^+Br^-$ was removed by filtration. The filtrate was concentrated in vacuo and partitioned between $Et_2O$ (100 mL) and $H_2O$ (60 mL). The organic phase was washed with 1N NaOH (3×) and brine, dried over $Na_2SO_4$ and concentrated in vacuo to afford 4.9 g of crude 2-(2-benzyloxyphenyl)thiazole (GCMS m/z 283 ($M^+$)). This material was directly deprotected by treatment with 33% HBr in HOAc (35 mL) for 2 hours at about 20° C.

The solution was poured onto ice/$H_2O$ (300 mL) and the pH adjusted to neutrality by addition of conc. $NH_4OH$. The product was extracted into EtOAc/$Et_2O$ (1:2) (250 mL) and the organic extract was washed with brine, dried over $Na_2SO_4$ and concentrated in vacuo to an oil. 2-[(Thiazol-2-yl)oxy]phenol was obtained as its HCl salt by precipitation from $Et_2O$ upon dropwise addition of 1N HCl in $Et_2O$ (15 mL). 2.25 g, 27% overall; GC-MS m/z 193 ($M^+$).

PREPARATION 16

3-[(Thiazol-2-yl)oxy]phenol

3-Methoxyphenol (2.48 g, 20 mmol), 2-bromothiazole (3.28 g, 20 mmol) and $Me_4N^+OH^-.5H_2O$ (3.62 g, 20 mmol) were heated in dry DMF (30 mL) under $N_2(g)$ for 16 hours. The mixture was filtered and the filtrate was partitioned between $H_2O$ and EtOAc. Organic extracts were pooled, dried over $Na_2SO_4$ and concentrated in vacuo. The residue was chromatographed on silica ($CHCl_3$) to yield 2.51 g of 2[(3-methoxyphenyl)oxy]thiazole (GC-MS m/z 207 ($M^+$)). A portion (2.42 g, 11.7 mmol) of this material was dissolved in dry $CH_2Cl_2$ (40 mL), and $BBr_3$ (2.2 eq.) was added dropwise at about −10° C. under $N_2(g)$. The mixture was allowed to warm to about 20° C., stirred 3 hours, and then poured into ice/$H_2O$ and extracted with $CH_2Cl_2$. Organic extracts were washed with 5% $NaHCO_3$ and brine, dried over $Na_2SO_4$ and concentrated in vacuo to yield 3-[(thiazol-2-yl)oxy]phenol as an oil (1.3 g) which was used without further purification (GC-MS m/z 193 ($M^+$)).

PREPARATION 17

2-[(Thiazol-2-yl)thio]phenol

To 2-methoxybenzenethiol (2.8 g, 20 mmol), and 2-bromothiazole (3.29 g, 20 mmol) in dry DMF (30 mL) under $N_2(g)$ was added $Me_4N^+OH^-.5H_2O$ (3.62 g, 20 mmol). The stirred mixture was heated to about 100° C. for 16 hours. Isolation of the methoxyphenyl intermediate, and its subsequent deprotection to the desired product with $BBr_3$ was accomplished according to the method described in Preparation 16 (yield 81%; GC-MS m/z 209).

PREPARATION 18

2-[(Imidazol-2-yl)methyl]-phenol

A mechanical mixture of imidazole (5 eq., 3.5 g) and 2-hydroxybenzyl alcohol (1.0 eq., 1.24 g) was heated to about 120° C. in a stoppered flask. The melt was stirred for 5 hours at about 120° C., allowed to cool and the fused mass was treated with hot $H_2O$ (40 mL) and the resulting suspension was cooled to about 4° C. The white crystalline precipitate was filtered and dried in vacuo to constant mass (1.49 g, 85%; LSIMS m/z 175 ($MH^+$)).

PREPARATION 19

2-(Imidazol-1-yl)phenol

To a mixture of oxazole (2.39 g, 34 mmol) and o-anisidine (69 mmol, 8.6 g) at about 20° C. was added $TsOH.H_2O$ (50 mg, 0.008 eq.) and the stirred mixture was gradually heated to reflux in a 160° oil bath over 30 minutes under $N_2(g)$. After 5 hours at about 160° C. most of the excess o-anisidine and N-formyl o-anisidine by-product were removed by vacuum distillation at about 160° C. (5 mm→0.5 mm Hg). The residue was partitioned between 1N HCl and EtOAc. The acidic aqueous phase was washed with $CH_2Cl_2$, the pH of the aqueous phase was adjusted to 10, and the 1-(2-methoxyphenyl)imidazole extracted into EtOAc. Passage through a filtration column of silica (40→65% acetone/hexane) afforded the pure methoxy intermediate (8.75 mg). The above compound was deprotected by addition of $BBr_3$ (2.0 eq.) to a $CH_2Cl_2$ solution (15 mL) of the imidazole at about −78° C. followed by warming and stirring 16 hours at about 20° C. The mixture was quenched with $H_2O$ (10 mL), and the pH of the aqueous phase adjusted to 7.5 with saturated aqueous $NaHCO_3$, and this phase was saturated with NaCl. Extractions with $CH_2Cl_2$ (2×) and EtOAc (2×), followed by drying of the pooled organic phases over $Na_2SO_4$ and concentration in vacuo afforded 1.05 g of a solid which was recrystallized from MeOH to produce pure 2-(Imidazol-1-yl)phenol as a tan solid (63%; GC-MS m/z 160 ($M^+$)).

PREPARATION 20

2-([1,3,4]Oxadiazol-2-yl)phenol

Salicyl hydrazide (7.6 g, 50 mmol) was heated to reflux in triethyl orthoacetate (40 mL) for 20 hours. Upon cooling to about 0° C. the product crystallized, and was recovered by decanting the excess triethyl orthoacetate, suspending the moist solid in cold EtOH (25 mL), filtering and drying in vacuo (4.43 g, 51%).

PREPARATION 21

1-(2-Methoxybenzoyl)-2-(nicotinoyl)hydrazide

To 2-Methoxybenzoyl hydrazide (7.0 g, 42 mmol) slurried in dry THF (10 mL) was added pyridine (3.0 eq., 126 mmol, 10 g) followed by nicotinoyl chloride hydrochloride (7.5 g, 42 mmol). Immediately product began to precipitate and after stirring 2.5 hours at about 20° C., the solids were filtered, washed with $Et_2O$ and dried in vacuo to yield 81% (9.23 g) of product.

PREPARATION 22

3-[2-(2-Methoxyphenyl)-[1,3,4]oxadiazol-5-yl]pyridine 1-(2-Methoxybenzoyl)-2-(nicotinoyl)hydrazide (2.0 g; 7.37 mmol) from above and $DMF.SO_3$ complex (4.52 g, 29.5 mmol) were stirred in dry DMF (20 mL) at about 80° C. for 2 hours. The reaction mixture was poured into $H_2O$ (100 mL) and extracted with $Et_2O$ (5×20 mL). The pooled organic extracts were washed with brine, dried over $Na_2SO_4$ and concentrated in vacuo to afford product (1.66 g, >95% pure) which was directly deprotected.

PREPARATION 23

2-(5-Pyridin-3-yl-[1,3,4]oxadiazol-2-yl)phenol

The methoxy derivative from Preparation 22 (0.80 g, 3.16 mmol) was mixed with solid pyridinium hydrochloride (9.12 g, 79 mmol) and heated to about 170° C. for 4 hours. $H_2O$ (20 mL) was added and the pH was adjusted to 7–8 with 6N NaOH. The aqueous mixture was extracted with EtOAc and $CH_2Cl_2$, and the pooled organic extracts were dried over $Na_2SO_4$, concentrated and chromatographed on silica (20–25% acetone/hexanes) to afford 43% (329 mg) product.

PREPARATION 24

3-[2-(2-Methoxyphenyl)-[1,3,4]thiadiazol-5-yl] pyridine

To a slurry of 1-(2-methoxybenzoyl)-2-(nicotinoyl) hydrazide (4.0 g, 14.8 mmol from Preparation 22) in anhydrous toluene (50 mL) was added Lawesson's reagent (2.0 eq., 29.6 mmol, 12.0 g). The stirred mixture was heated to reflux under $N_2(g)$ for 16 hours. The cooled (20° C.) reaction mixture was filtered and the residue was washed with $CH_3CN$ and $CH_2Cl_2$. The pooled filtrate and washes were concentrated in vacuo and chromatographed on silica (35% acetone/hexanes) to afford 85–90% product (3.5 g; LSIMS m/z 270 ($MH^+$)).

PREPARATION 25

2-(5-Pyridin-3-yl-[1,3,4]thiadiazol-2-yl)phenol

The methoxy derivative from preparation 24 (3.6 g) was deprotected by heating with pyridinium hydrochloride (20 g) at about 170° C. for 16 hours as described in Preparation 24 to afford 1.1 g product 32%; LSIMS m/z 255 ($MH^+$) after chromatography of the extracts on silica (0→2% MeOH/ $CH_2Cl_2$).

PREPARATION 26

2-(5-Pyridin-4-yl-[1,3,4]thiadiazol-2-yl)phenol

This product was prepared as outlined for the pyridin-3-yl analog of Preparations 24 and 25 but utilizing isonicotinoyl chloride with 2-methoxybenzoyl hydrazide in the initial formation of the diacyl hydrazide.

PREPARATION 27

Potassium dithioformate

KOH (12 g) in MeOH (45 mL) was saturated with $H_2S(g)$ at about 5° C. A solution of KOH (11 g) in MeOH (35 mL) was added to this solution in a 500 mL round-bottom flask equipped with a reflux condenser. The solution was warmed to about 50° C. and $CHCl_3$ (15 g) was added. After the exothermic reaction subsided the red-orange mixture was stirred for 10 minutes at about 50° C., then cooled in ice/$H_2O$ and precipitated KCl(s) was removed by filtration and washed with MeOH. The pooled filtrate and washings containing about 33 mmol potassium dithioformate were concentrated to approximately 50 mL and used immediately in subsequent reactions.

PREPARATION 28

2-([1,3,4]Thiadiazol-2-yl)phenol

Salicyl hydrazide (33 mmol, 5.0 g) was added to the methanolic solution of potassium dithioformate (about 33 mmol in 50 mL from preparation 27) along with $H_2O$ (40 mL). The mixture was stirred for 24 hours under $N_2(g)$, diluted to 150 mL with $H_2O$ and neutralized with HOAc (with evolution of $H_2S(g)$) to produce a precipitate of 2-(2-hydroxybenzoyl)-1-thioformyl hydrazide (6.5 g, 100%) which was filtered and dried. This material (5.8 g) was directly cyclized by addition in small portions to stirred conc. $H_2SO_4$ (30 mL) at about 20° C. After 30 minutes the solution was poured onto ice (150 mL) and neutralized with con. $NH_4OH$ with cooling on ice/$H_2O$ to precipitate 2-([1, 3,4]thiadiazol-2-yl)phenol (2.12 g; GC-MS m/z 178).

PREPARATION 29

3-([1,3,4]Thiadiazol-2-yl)phenol

This product was prepared in a manner analogous to that for 2-([1,3,4]thiadiazol-2-yl)phenol of Preparation 28 but utilizing 3-hydroxybenzoyl hydrazide (2.5 g, 16.5 mmol), 2.58 g product was isolated.

PREPARATION 30

2-(5-Methyl-[1,3,4]thiadiazol-2-yl)phenol

To acetyl hydrazide (9.9 g, 50 mmol) in anhydrous pyridine (60 ml) at 0–5° C. was added o-acetylsalicyl chloride (9.93 g, 50 mmol). The solution was stirred 4 hours at about 20° C., and $P_2S_5$ (15 g) was added. The resulting mixture was heated to near boiling within 10 minutes at which point all of the $P_2S_5$ dissolved. After 40 minutes the mixture had cooled and was then heated in a bath at about 100° C. for 16 hours. EtOH (60 mL) was added and the mixture was poured into $H_2O$ (800 mL) and stirred for 30 minutes. The pH of the stirred mixture under $N_2(g)$ was raised to about 11 and maintained by addition of 6N NaOH. After 1 hour at about 20° C. the pH was adjusted to 6–7 by addition of 6N HCl, and the mixture extracted with EtOAc. Organic extracts were pooled, dried over $Na_2SO_4(s)$, concentrated and flash chromatographed on silica (10→15% acetone/hexanes) to yield the desired product as a beige solid (950 mg, 10%; LSIMS m/z 193 ($MH^+$)).

PREPARATION 31

3-(5-Phenyl-[1,3,4]thiadiazol-2-yl)phenol

3-Hydroxybenzoyl hydrazide (3.6 g, 23.5 mmol) was added to 5-(thiobenzoyl)-thioglycolic acid (5.0 g, 23.5 mmol) in 1N NaOH (24 mL) with $H_2O$ (10 mL) and MeOH (10 mL). After stirring 16 hours at about 20° C. the mixture was filtered, and the residue of 1-thiobenzoyl-2-(3-hydroxybenzoyl)hydrazide (LSIMS m/z 273) was washed with $H_2O$ and dried briefly. This material was cyclized in conc. $H_2SO_4$ as described for the 2-([1,3,4]thiadiazol-2-yl) phenol analog of Preparation 28 to afford 85% product (4.57 g; LSIMS m/z 255 ($MH^+$)).

PREPARATION 32

2-(Dimethylamino)benzothiazol-7-ol

To m-anisidine (12.32 g, 0.1 mol) and triethylamine (1.2 eq, 0.12 mol, 16.7 mL) in $CH_2Cl_2$ (100 mL) was added a 1M solution of dimethylthiocarbamyl chloride in $CH_2Cl_2$ (100 mL, 0.10 mol) with stirring at about 0° C. for about 5 minutes. The solution was allowed to warm to about 22° C. and stirred for about 16 hours under $N_2(g)$. The mixture was concentrated in vacuo to a syrup, $H_2O$ (250 mL) was added and the mixture was stirred for about 1 hour at about 40–50° C. Concentrated HCl (50 mL) was added and the mixture was extracted with $Et_2O$ (3×200 mL). The etheral phases were washed with 2N HCl (3×150 mL), $H_2O$ (100 mL), and saturated $NaHCO_3$ (100 mL), and dried over $Na_2SO_4(s)$. Concentration in vacuo afforded a brown solid which was recrystallized from $CHCl_3/Et_2O$/hexanes to provide pure thiourea (8.6 g). Additional thiourea (4.1 g) crystallized from the acidic aqueous phases on standing for several days.

A mixture of the thiourea from above (4.46 g, 21 mmol) and NaOH (6.3 g, 156 mmol) in MeOH (25 mL)/H$_2$O (80 mL) was added dropwise with stirring to a solution of K$_3$Fe(CN)$_6$ (23.0 g, 70 mmol, 3.3 eq) in H$_2$O (60 mL) at about 60–65° C. over about 15 minutes. The mixture was stirred for about 2 hours at about 60° C. and then K$_2$CO$_3$(s) (16 g) was added. The stirred mixture was allowed to cool and then extracted with Et$_2$O (2×100 mL) and CHCl$_3$ (1×80 mL). Pooled organic extracts were dried over Na$_2$SO$_4$(s), and concentrated in vacuo onto 20 g of silica and flash chromatographed using 15→30% acetone/hexanes to afford 1.6–2.2 g (37–50%) of 2-(dimethylamino)-7-methoxybenzothiazole.

The 7-methoxy derivative from above (800 mg, 3.8 mmoles) was mechanically mixed with pyridinium hydrochloride (11.2 g, 0.10 mol) and heated to about 160° C. for about 18 hours. The mixture was poured onto ice/H$_2$O and stirred for about 10 min. and then extracted with CHCl$_3$ (5×50 mL). Pooled organic phases were dried over Na$_2$SO$_4$ (s), filtered and concentrated in vacuo to afford 730 mg (98%) of 2-(dimethylamino)benzothiazol-7-ol as a grey solid (GC-MS m/z 194) which was used without further purification.

PREPARATION 33

2-(Pyridin-3-yl)benzothiazol-7-ol

To a stirred solution of m-anisidine (50 mmol, 5.62 mL, 6.16 g) in 2:1 THF/H$_2$O (75 mL) with NaHCO$_3$(s) (8.4 g, 0.1 mol) was added nicotinoyl chloride hydrochloride (50 mmol, 8.9 g) in small portions over about 5 min. at about 20° C. The mixture was stirred under N$_2$(g) for about 20 hours and then saturated aqueous NaHCO$_3$ (60 mL) and Et$_2$O (75 mL) were added. The organic phase which separated was washed with saturated aqueous NaHCO$_3$ (3×30 mL), and brine (1×30 mL), dried over Na$_2$SO$_4$(s) and concentrated in vacuo. The solid residue was recrystallized from Et$_2$O/petroleum ether to afford 8.65 g of the nicotinamide. This product (5.0 g, 21.9 mmol) was suspended in dry toluene (100 mL) with Lawesson's reagent (17.1 g, 42.3 mmol) and heated to reflux under N$_2$(g) for about 16 hours. After cooling to about 20° C. the mixture was filtered and the residue was washed with anhydrous THF (2×50 mL). Pooled filtrate and washings were concentrated in vacuo, stirred vigorously in i-PrOH (100 mL) and saturated NaHCO$_3$ (250 mL) at about 50° C. for about 90 min., cooled and extracted into CHCl$_3$ (2×200 mL). The oily residue obtained after drying the extract over Na$_2$SO$_4$(s) and concentration in vacuo was flash chromatographed on silica using a 50→60% acetone/hexanes gradient to yield 3.1 g of pure nicotinoylthioamide.

The thioamide (2.44 g, 101 mmol) from above was suspended in a mixture of MeOH (40 mL) and aqueous NaOH (3.2 g in 100 mL H$_2$O) and added dropwise over 10 min. to a solution of K$_3$Fe(CN)$_6$ (11.5 g) in H$_2$O (40 mL) at about 60° C. After stirring for about 2 hours at about 60° C. additional K$_3$Fe(CN)$_6$ (6 g) was added and stirring at about 60° C. was continued for about another 1 hour. K$_2$CO$_3$(s) (8.2 g) was added at about 60° C. and the stirred mixture was allowed to cool about 30 min. before extracting with Et$_2$O (3×80 mL). Pooled organic extracts were dried over MgSO$_4$ (s), filtered and concentrated to give 2.1 g of an oil which was flash chromatographed on silica (35→40% EtOAc/hexanes) to afford pure 7-methoxy-2-(pyridin-3-yl)benzothiazole (0.67 g). This material was O-demethylated using molten pyridinium hydrochloride as previously described in Preparation 32 to yield 2-(pyridin-3-yl) benzothiazol-7-ol. LC-MS m/z 229 (MH$^+$); Analytical RP-HPLC, 3.10 min.

PREPARATION 34

2-Methyl-benzoxazol-6-ol

4-Aminoresorcinol hydrochloride (2.0 g, 12.4 mM), acetyl chloride (1.0 g, 12.6 mM), triethylamine (1.38 g, 13.6 mM) and pyridinium-p-toluenesulfonate (PPTS, 800 mg, 3.2 mM) were refluxed in xylenes (50 mL) for about 18 hours. Additional PPTS (300 mg) was added and the mixture was then refluxed about 48 hours. The reaction mixture was concentrated and the residue dissolved in ethyl acetate (200 mL) and washed with H$_2$O (3×150 mL). The combined aqueous layer was back extracted with ethyl acetate (200 mL) and the combined organic layers were dried over MgSO$_4$. Filtration and concentration provided 1.36 g. Filtration through a silica gel column eluted with 10% methanol/methylene chloride provided an orange solid, 0.3 g; m.p., 94–96° C.

PREPARATION 35

2-(Pyridin-2-yl)-benzoxazol-6-ol

4-Aminoresorcinol hydrochloride (2.0 g, 12.4 mL), picolinyl chloride hydrochloride (2.4 g, 13.6 mM), triethylamine (2.8 g, 27.2 mM) and pyridinium-p-toluenesulfonate (PPTS, 800 mg, 3.2 mM) were refluxed in xylenes (50 mL) for about 72 hours. The reaction mixture was concentrated and the residue dissolved in ethyl acetate (200 mL) and washed with H$_2$O (3×150 mL). The combined aqueous layer was back extracted with ethyl acetate (200 mL) and the combined organic layer was dried over MgSO$_4$. Filtration and concentration provided 1.0 g. Filtration through a silica gel column eluted with 4% methanol/methylene chloride provided an orange solid, 0.32 g; m.p., 100–103° C.

PREPARATION 36

2-(Pyridin-3-yl)-benzoxazol-6-ol

2-Pyridin-3-yl-benzoxazol-6-ol was prepared using 4-aminoresorcinol hydrochloride (1.5 g, 9.3 mM), nicotinyl chloride hydrochloride (1.8 g, 10.2 mM), triethylamine (3.0 g, 30.0 mM) and pyridinium-p-toluenesulfonate (PPTS, 800 mg, 3.2 mM) were refluxed in xylenes (50 mL) for about 24 hours as described for 2-pyridin-2-yl-benzoxazol-6-ol; m.p., 176–178° C.

PREPARATION 37

2-(Pyridin-4-yl)-benzoxazol-6-ol

2-Pyridin-4-yl-benzoxazol-6-ol was prepared using 4-aminoresorcinol hydrochloride (1.5 g, 9.3 mM), isonicotinyl chloride hydrochloride (1.8 g, 10.2 mM), triethylamine (3.0 g, 30.0 mM) and pyridinium-p-toluenesulfonate (PPTS, 800 mg, 3.2 mM) were refluxed in xylenes (50 mL) for about 24 hours as described for 2-pyridin-2-yl-benzoxazol-6-ol; m.p., 139–143° C.

PREPARATION 38

Benzoxazol-6-ol

4-Aminoresorcinol hydrochloride (3.0 g, 18.5 mM), triethylorthoformate (9.1 g, 61.4 mM), and pyridinium-p-toluenesulfonate (PPTS, 250 mg, 1.0 mM) were refluxed in xylenes (200 mL) for about 18 hours. The reaction mixture was concentrated and the residue dissolved in ethyl acetate (200 mL) and washed with H$_2$O (3×150 mL). The combined aqueous layer was back extracted with ethyl acetate (200 mL) and the combined organic layer was dried over MgSO$_4$. Filtration and concentration provided an oil that was filtered through a silica gel column eluted with 1% methanol/methylene chloride to provide a brown solid, 1.66 g; m.p., 118–121° C.

PREPARATION 39

3-Benzothiazol-2-yl-phenol

3-Hydroxybenzonitrile (1 g, 8.4 mM) and 2-thioaniline (1.05 g, 8.4 mM) were melted at 110° C. and refluxed for about 18 hours. The black solution was poured into ice water (100 mL) causing a gray precipitate to form which dissolved in ether. The insolubles were filtered and the filtrate concentrated on a steam bath and the product precipitated by addition of petroleum ether; m.p., 144–145° C.

PREPARATION 40

α-Bromo-3-acetoxy acetophenone

3-Acetoxy acetophenone (22 g, 123 mM) was dissolved in carbon tetrachloride (125 mL) and treated with bromine (6.36 mL, 123 mM) dropwise over 10 minutes at room temperature. After about 4 hours the mixture was carefully poured into a saturated sodium bicarbonate solution until basic. The layers were separated and the aqueous layer extracted with methylene chloride (200 mL). The combined organic layer was washed with saturated sodium bicarbonate solution (100 mL) followed by 5% aqueous sodium bisulfite (100 mL), H$_2$O (100 mL) and finally saturated brine solution (100 mL). Filtration of the organic layer through a cotton plug and concentration provides an oil (31 g) of crude material used in the preparation of thiazoles.

PREPARATION 41

3-(2-Methylthiazol-4-yl)phenol

α-Bromo-3-acetoxy acetophenone (4.25 g, 16.5 mM) and thioacetamide (1.36 g, 18.1 mM) were refluxed in acetone (30 mL) for about 18 hours. The solvent was evaporated and the crude material treated with methylene chloride which caused the product to precipitate. This was collected by filtration (2.5 g), dissolved in THF (100 mL) and treated with 3N NaOH (6 mL) which caused the phenolic product to precipitate. Filtration and rinsing with THF (20 mL) provided 1.5 g of a yellow solid; m.p., 102–103° C.

PREPARATION 42

3-(2-Substituted-thiazol-4-yl)-phenols

α-Bromo-3-acetoxy acetophenone (1 eq) and thioamide (1.1 eq) were refluxed in acetone (2–5 volumes) for about 18 hours. The solvent was evaporated and the crude material treated with methylene chloride causing product to precipitate. This was collected by filtration, dissolved in THF (100 mL) and treated with 3N NaOH (1.5–2 eq.). After consumption of starting material detected by (TLC) the product was extracted with ethyl acetate, washed with saturated sodium bicarbonate solution and saturated brine solution. Drying and concentration provides material suitable for preparation of glycidyl ethers.

PREPARATION 43

3-(2-Phenylthiazol-4-yl)-phenol 3-(2-Phenylthiazol-4-yl)phenol was prepared from α-bromo-3-acetoxy acetophenone and thiobenzamide as described in Preparation 42 and it was used in a crude state for the preparation of the glycidyl ether; m.p., 109–110° C.

PREPARATION 44

3-(2-Pyridin-2-yl-thiazol-4-yl)phenol 3-(2-Pyridin-2-yl-thiazol-4-yl)phenol was prepared from a α-bromo-3-acetoxy acetophenone and thiopicolinamide as described in Preparation 42 and it was used in a crude state for the preparation of the glycidyl ether; m.p., 120–121° C.

PREPARATION 45

3-(2-Pyridin-3-yl-thiazol-4-yl)-phenol 3-(2-Pyridin-3-yl-thiazol-4-yl)-phenol was prepared from a α-bromo-3-acetoxy acetophenone and thionicotinamide as described in Preparation 42; m.p. 180–181° C. (CH$_2$Cl$_2$).

PREPARATION 46

3-(2-Pyridin-4-yl-thiazol-4-yl)phenol 3-(2-Pyridin-4-yl-thiazol-4-yl)phenol was prepared from α-bromo-3-acetoxy acetophenone and thioisonicotinamide as described in Preparation 42 and it was used in a crude state for the preparation of the glycidyl ether; m.p., 158–159° C.

PREPARATION 47

α-Bromo-4-hydroxyacetophenone

4-Hydroxyacetophenone (25 g) was treated with bromine (9.5 mL) dropwise over 15 minutes in THF (60 mL) at room temperature and stirred until the color was consumed. The whole was carefully poured into saturated sodium bicarbonate solution until basic. The aqueous layer was extracted with ether (3×100 mL) and the ether layer was washed with saturated sodium bicarbonate solution (100 mL) followed by 5% aqueous sodium bisulfite (100 mL), H$_2$O (100 mL) and finally saturated brine solution (100 mL). The organic layer was dried over MgSO$_4$, filtered and concentrated to provide an oil (30 g) of crude material used in the preparation of thiazoles.

PREPARATION 48

4-(2-Substituted-thiazol-4-yl)phenol hydrobromide

α-Bromo-4-hydroxyacetophenone (1 eq) and thioamide (1.1 eq) were refluxed in acetone (2–5 volumes) for about 18 hours. After cooling, the product was collected by filtration and recrystallized from methylene chloride.

PREPARATION 49

4-(2-Pyridin-2-yl-thiazol-4-yl)phenol hydrobromide 4-(2-Pyridin-2-yl-thiazol-4-yl)phenol hydrobromidewas preparedfrom α-bromo-4-hydroxyacetophenone and thiopicolinamide as described in Preparation 48; m.p. 261–262° C.

PREPARATION 50

4-(2-Methylthiazol-4-yl)phenol hydrobromide 4-(2-Methylthiazol-4-yl)-phenol hydrobromide was prepared from α-bromo-4-hydroxyacetophenone and thioacetamide as described in Preparation 48; m.p. 250–251° C. (CH$_2$Cl$_2$).

PREPARATION 51

4-(2-Phenylthiazol-4-yl)phenol

α-Bromo-4-hydroxyacetophenone was prepared as described above (1.68 g, 7.3 mM) and thiobenzamide (1.1 g, 8.0 mM) were refluxed in acetone (30 mL) for about 18 hours. After cooling, the hydrobromide salt of the product was collected by filtration and recrystallized from methylene chloride, (1.44 g, mp. 175–176° C.).

PREPARATION 52

3-([1,3,4]-Oxadiazol-2-yl)phenol

3'-Hydroxyphenylbenzhydrazide (4.0 g, 26.3 mM) and triethylorthoformate (5.85 g, 39.5 mM) were brought to reflux in xylenes (20 mL) under $N_2$ for about 18 hours. (Formation of an intermediate is observed as a precipitate that redissolves upon prolonged heating). After cooling, hexanes and ethanol were added to induce precipitation of a chalky solid which was collected by filtration, 2.9 g. Recrystallization from ethanol/hexanes provided yellow granules, 1.3 g; m.p., 128–129° C.

PREPARATION 53

3'-(5-Methyl-[1,3,4]-oxadiazol-2-yl)phenol

3'-Hydroxyphenylbenzhydrazide (4.0 g, 26.3 mM) and triethylorthoacetate (6.4 g, 39.5 mM) were brought to reflux in xylenes (20 mL) under $N_2$ for about 18 hours. (Formation of an intermediate is observed as a precipitate that redissolves upon prolonged heating). Distillation of the ethanol formed in the reaction and dilution with hexanes precipitated the product which was collected by filtration, 4.23 g; m.p., 85–92° C.

PREPARATION 54

3-(5-Ethyl-[1,3,4]-oxodiazol-2-yl)phenol

3'-Hydroxyphenylbenzhydrazide (4.0 g, 26.3 mM) and triethylorthopropionate (6.96 g, 39.5 mM) were brought to reflux in xylenes (20 mL) under $N_2$ for about 18 hours. (Formation of an intermediate is observed as a precipitate that redissolves upon prolonged heating). Concentration and treatment with hexanes produced a yellow precipitate which was recrystallized from ethanol/hexanes, 3.0 g; m.p., 163–165° C.

PREPARATION 55

4-(5-Methyl-[1,3,4]-oxodiazol-2-yl)phenol

4'-Hydroxyphenylbenzhydrazide (5.0 g, 32.9 mM) and triethylorthoacetate (8.19 g, 50.5 mM) were brought to reflux in xylenes (30 mL) under $N_2$ for about 18 hours. (Formation of an intermediate is observed as a precipitate that redissolves upon prolonged heating). Distillation of the ethanol formed in the reaction and dilution with hexanes precipitated light brown crystals which were collected by filtration and dried, 4.68 g; m.p., 334–335° C.

PREPARATION 56

4-(5-Ethyl-[1,3,4]-oxadiazol-2-yl)phenol

4'-Hydroxyphenylbenzhydrazide (5.0 g, 32.9 mM) and triethylorthopropionate (8.75 g, 49.7 mM) were brought to reflux in xylenes (30 mL) under $N_2$ for about 18 hours. (Formation of an intermediate is observed as a precipitate that redissolves upon prolonged heating). Distillation of the ethanol formed in the reaction and dilution with hexanes precipitated a white product which was collected by filtration and dried, 3.74 g; m.p., 204–206° C.

PREPARATION 57

3-Hydroxybenzaminoxime

3-Hydroxybenzonitrile (10.0 g, 84 mM) and hydroxylamine hydrochloride (5.84 g, 84 mM) were dissolved in ethanol (125 mL) and treated with a solution of sodium hydroxide (3.36 g, 84 mM) in $H_2O$ (30 mL) under an atmosphere of nitrogen. This mixture was refluxed for about 5 hours and concentrated to an oil. This was treated with $H_2O$ (300 mL), extracted with ethyl acetate (3×100 mL) dried over $MgSO_4$, filtered and concentrated to an orange oil (13.5 g) which was used without further purification.

PREPARATION 58

3-Pyridoaminoxime

3-Cyanopyridine (5.0 g, 48 mM) and hydroxylamine hydrochloride (3.4 g, 48 mM) were dissolved in ethanol (80 mL) and treated with a solution of sodium hydroxide (1.95 g, 48 mM) in $H_2O$ (20 mL) under an atmosphere of nitrogen. This mixture was refluxed for about 36 hours and concentrated to an oil. This was treated with $H_2O$ (200 mL), extracted with ethyl acetate (3×100 mL) dried over $MgSO_4$, filtered and concentrated to an orange oil (5.6 g) which was used without further purification.

PREPARATION 59

3-(3'-Bromopropoxy)benzonitrile

3-Cyanophenol (10.0 g, 84 mM), 3-bromopropanol (20.3 mL, 114 mM), triphenylphosphine (29.7 g, 114 mM) were stirred in anhydrous THF (40 mL) at room temperature and treated with diethylazodicarboxylate (17.8 mL, 114 mM) dropwise over 5 min. under an atmosphere of nitrogen. This mixture stirred for about 5 hours then diluted with ether (500 mL) and filtered through Celite™. The filtrate was concentrated to a reddish oil which was again dissolved in ether (250 mL), diluted with hexanes (200 mL) and filtered. The filtrates were concentrated then filtered through a silica pad (300 g) eluting with 35% acetone/hexanes to collect the desired product as a yellow oil, 16.85 g. This material was used in its crude form.

PREPARATION 60

4-Benzhydryl-1-(3-(3-benzonitriloxyl)-propyl)-piperidine

4-Benzhydrylpiperidine hydrochloride (7.8 g, 27 mM) and diisopropylethylamine (9.4 mL, 54.2 mM) were combined in dioxane (10 mL) and water (2 mL) at about 0° C. causing a white slurry to form and 3-(3'-Bromopropoxy)-benzonitrile (5.0 g, 20.9 mM) in dioxane (10 mL) was added dropwise. This mixture was stirred for about 48 hours at ambient temperature and then at reflux for about 2 hours. After cooling, the mixture was poured into water (200 mL) and extracted with methylene chloride (2×100 mL). The organic layer was washed with 1N HCl solution (2×250 mL), saturated aqueous sodium hydrogen carbonate solution (2×250 mL), filtered through a plug of cotton and concentrated to a yellow oil. Column chromatography on silica gel (200 g) eluting with 3% methanol/methylene chloride provided 6.95 g of an orange oil.

PREPARATION 61

4-Benzhydryl-1-(3-(3-benzoaminoxime)-propyl)-piperidine

4-Benzhydryl-1-(3-(3-benzonitriloxyl)-propyl)-piperidine (1.0 g, 2.44 mM), hydroxylamine hydrochloride (0.18 g, 2.59 mM) and sodium hydroxide (0.22 g, 5.5 mM) were combined in ethanol/water (5 mL, 4/1) and heated to reflux under an atmosphere of nitrogen for about 3 hours. The ethanol was removed in vacuo and the residue was diluted with water (100 mL) and extracted with ethyl acetate (3×150 mL). The organic layer was washed with brine and dried over $MgSO_4$, filtered and evaporated to yield 0.75 g of a white foam.

PREPARATION 62

3-(5-Substituted-[1,2,4]oxadiazol-3-yl)phenol

Amidoxime (1 eq) and an acid chloride (1 eq) were warmed to reflux in pyridine (1 volume) for about 18 hours. After cooling, the mixture was poured into $H_2O$ and stirred for about 8 hours and the product was filtered and dried. Typically these were used without further purification.

PREPARATION 63

3-(5-Methyl-[1,2,4]oxadiazol-3-yl)phenol 3-(5-Methyl-[1,2,4]oxadiazol-3-yl)-phenol was prepared using 3-hydroxybenzamidoxime (1 g, 6.6 mM) and acetyl chloride (0.52 g, 6.7 mM) in pyridine (4 mL) according to Preparation 62 to provide 0.66 g of a white powder; m.p., 87–89° C.

PREPARATION 64

3-(5-Pyridin-3-yl)-[1,2,4]oxadiazol-3-yl)phenol 3-(5-Pyridin-3-yl-[1,2,4]oxadiazol-3-yl)phenol was prepared using 3-hydroxybenzamidoxime (1 g, 6.6 mM) and nicotinoyl chloride hydrochloride (1.2 g, 6.6 mM) in pyridine (4 mL) using Preparation 62 to provide 1.0 g of a brown precipitate; m.p., 120–123° C.

PREPARATION 65

3-(5-Pyridin-4-yl-[1,2,4]oxadiazol-3-yl)phenol 3-(5-Pyridin-4-yl-[1,2,4]oxadiazol-3-yl)phenol was prepared using 3-hydroxybenzamidoxime (3 g, 19.7 mM) and isonicotinyl chloride hydrochloride (3.51 g, 19.6 mM) in pyridine (15 mL) using Preparation 62 to provide 3.65 g of a brown precipitate; m.p., 145–146° C.

PREPARATION 66

3-(5-(3-Methoxyphenyl)-[1,2,4]oxadiazol-3-yl]pyridine

3-[5-(3-Methoxyphenyl)-[1,2,4]oxadiazol-3-yl)pyridine was prepared using 3-pyridoamidoxime (2.2 g, 16.0 mM) and 3-methoxybenzoyl chloride (2.74 g, 16.0 mM) in pyridine (10 mL) using Preparation 62 to provide 3.57 g white precipitate.

PREPARATION 67

3-(3-Pyridin-3-yl-[1,2,4]oxadiazol-5-yl)phenol

3-[5-(3-Methoxyphenyl)-[1,2,4]oxadiazol-3-yl)pyridine (4.0 g, 15.79 mM) and pyridine hydrochloride (37.6 g, 325 mM) were melted together at about 160° C. under an atmosphere of nitrogen for about 30 hours. This mixture was poured into $H_2O$ and stirred. The precipitated product was filtered and dried, 2.9 g, mp. >200° C.

PREPARATION 68

3-(Pyridin-2-ylamino)phenol

3-Aminophenol (3.0 g, 27.5 mM) and 2-bromopyridine (4.34 g, 27.5 mM) were combined in acetic acid (15 mL) and heated for about 18 hours. The mixture was concentrated in vacuo and placed on a column of silica gel (150 g). The product was eluted with 3% methanol/methylene chloride to provide 1.2 g of an off white solid.

PREPARATION 69

Glycidyl Ethers

The appropriate phenol (1 eq) and potassium t-butoxide (1.05 eq.) are combined in anhydrous THF (2 volumes) under an atmosphere of nitrogen. After heating to reflux for about 15 min., the mixture was cooled to ambient temperature and treated with n-$Bu_4NI$ (0.05 eq.) and DMF (0.05 eq.) then epibromohydrin (1.1 eq.). This mixture is brought to reflux for about 18 hours or until the reaction is deemed complete. After cooling the reaction is poured into saturated sodium hydrogen carbonate solution and the product is extracted with methylene chloride. The resulting organic layer is washed with brine then passed through a plug of cotton and concentrated to an oil. Typically this product was taken on without further purification but can be purified by column chromatography to homogeneity.

PREPARATION 70

Glycidyl Ethers

The appropriate phenol (1 eq.) and sodium hydride (1.5 eq.) are combined in anhydrous DMF (3 volumes) and stirred under an atmosphere of nitrogen until hydrogen evolution ceases. Epichlorohydrin (1.2 eq.) is added and this mixture is brought to about 60° C. for about 18 hours or until the reaction is deemed complete. After cooling, the reaction is poured into 50% saturated sodium chloride solution and the product is extracted with ethyl acetate (6×), dried over $MgSO_4$ and concentrated to an oil. Typically this product was taken on without further purification but could be purified by column chromatography to homogeneity.

PREPARATION 71

5-(2,3-Epoxypropoxy)-1-hydroxy-3,4-dihydroquinoline

A suspension of 1,5-dihydroxy-3,4-dihydroisoquinoline (500 mg, 3.1 mmol) and sodium hydride (129 mg 60% oil dispersion) in 15 mL of DMF was warmed to about 50° C. for about 30 min.

Epichlorohydrin (850 mg, 3.1 mmol) was added and the resulting mixture was heated at about 90° C. for about 3 hours. After it was cooled, water was added and extracted with EtOAc and $CH_2Cl_2$. The residue obtained after evaporation of the organic solvents was chromatographed on silica gel (1% MeOH—$Ch_2Cl_2$) to give 295 mg of 5-(2,3-epoxypropoxy)-1-hydroxy-3,4-dihydroisoquinoline.

PREPARATION 72

5-(2,3-Epoxypropoxy)-2-hydroxy-3,4-dihydroquinoline

The title compound was prepared according to the method of Preparation 71 but using 3,4-dihydro-5- hydroxycarbostyril instead of 1,5-dihydroxy-3,4-dihydroisoquinoline.

PREPARATION 73

5-(2,3-Epoxypropoxy)-1-tetralone

The title compound was prepared according to the method of Preparation 71 but using 5-hydroxytetralone instead of 1,5-dihydroxy-3,4-dihydroisoquinoline.

PREPARATION 74

6-(2,3-Epoxypropoxy)-1,3,4,5-tetrahydro-2H-1-benzazepin-2-one

The title compound was prepared according to the method of Preparation 71 but using 1,3,4,5-tetrahydro-6-hydroxy-2H-1-benzazepin-2-one instead of 1,5-dihydroxy-3,4-dihydroisoquinoline.

PREPARATION 75

6-(2,3-Epoxypropoxy)-2,3,4,5-tetrahydro-1H-2-benzazepin-1-one

The title compound was prepared according to the method of Preparation 71 but using 2,3,4,5-tetrahydro-6-hydroxy-1H-2-benzazepin-1-one instead of 1,5-dihydroxy-3,4-dihydroisoquinoline.

PREPARATION 76

6-(2,3-Epoxypropoxy)4,5-dihydro-2-picolylamino-3H-benzazepine

The title compound was prepared according to the method of Preparation 71 but using 4,5-dihydro-6-hydroxy-2-picolylamine-3H-benzazepine instead of 1,5-dihydroxy-3,4-dihydroisoquinoline.

PREPARATION 77

4,5-Dihydro-6-hydroxy-2-picolylamine-3H-benzazepine

A suspension of 1,3,4,5-tetrahydro-6-hydroxy-2H-1-benzazepin-2-one (500 mg, 2.82 mmol) in 2.5 mL each of pyridine and acetic acid was stirred at room temperature. Excess reagents were removed under reduced pressure and the residue was triturated with $CH_2Cl_2$ to give 540 mg (87%) of 1,3,4,5-tetrahydro-6-acetoxy-2H-1-benzazepin-2-one; MS 219.

A suspension of 1,3,4,5-tetrahydro-6-acetoxy-2H-1-benzazepin-2-one (50 mg, 0.23 mmol) and Lawesson reagent (65 mg, 0.16 mmol) in 3 mL of toluene was refluxed for about 1 h. The residue obtained after evaporation of the solvent was chromatographed on silica gel PTLC (5% MeOH—$CH_2Cl_2$) to give 51 mg (94%) of 1,3,4,5-tetrahydro-6-acetoxy-2H-1-benzazepin-2-thione; MS 235.

To a solution of 1,3,4,5-tetrahydro-6-acetoxy-2H-1-benzazepin-2-thione (235 mg, 1.0 mmol) in 25 mL of $CH_2Cl_2$ was added at 0° 295 mg (2.0 mmol) of trimethyloxonium tetrafluoroborate. After stirring at room temperature for about 30 min. water was added and the $CH_2Cl_2$ layer was separated. Drying over $Na_2SO_4$ and removal of the solvent gave 229 mg of 4,5-dihydro-6-acetoxy-2-methylthio-3H-benzazepine.

A mixture of 4,5-hydro-6-acetoxy-2-methylthio-3H-benzazepine (240 mg, 0.96 mmol) and 2-picolylamine (209 mg, 1.92 mmol) in 4 mL of 2-(2-ethoxyethoxy) ethanol was heated at about 150° C. for about 3 h. The solvent was removed under reduced pressure and the residue was chromatographed on silica gel ($CH_2Cl_2\rightarrow 20\%$ MeOH—$CH_2Cl_2$) to give 207 mg (81%) of 4,5dihydro-6-hydroxy-2-picolylamino-3H-benzazepine: MS 267.

PREPARATION 78

N-Hydroxybenzhydrylpiperidine

Benzhydrylpiperidine (1 eq., 1.818 g, 7.63 mmol), $Na_2HPO_4$ (5 eq., 5.4 g, 38.0 mmol) and 1:1 $Et_2O$/THF (40 ml) were combined with dibenzoyl peroxide (1.1 eq., 2.040 g, 8.42 mmol) while THF was introduced via an addition funnel and the reaction mixture was stirred under $N_2$ at about 20° C. At the end of the addition, the white suspension was heated at reflux overnight. After 18 hours the solution was cooled; a white precipitate formed during the cooling process. The white precipitate was filtered and washed with $CH_2Cl_2$. The filtrate was concentrated in vacuo and resuspended in $CH_2Cl_2$. The resulting yellow solution was washed sequentially with 10% aqueous $Na_2CO_3$ (2×15 ml) and brine. The organic layers were dried over $MgSO_4$(s) filtered and concentrated in vacuo to give 2.75 g of a sticky yellow solid. Flash chromatography on silica using 15% EtOAc/hexanes gave 1.72 g of a white/yellow powder, LSIMS, 372 MH$^+$.

The white/yellow powder was dissolved in about 30 ml of $Et_2O$ and added dropwise to 0.203 g (5.19 mmol) of potassium metal in 10 ml of MeOH and stirred at room temperature for about 22 hours. The resulting cloudy yellow solution was concentrated in vacuo, resuspended in $H_2O$ and extracted with $Et_2O$. The organic layers were combined, dried over $MgSO_4$(s) filtered and concentrated in vacuo to give 1.20 g of a yellow solid. Chromatography on silica using 100% EtOAc gave 0.89 g of an off-white solid, LSIMS, 268 MH$^+$.

PREPARATION 79

2-Ethyl-benzothiazol-7-ol

A solution of 3-methoxyphenyl isothiocyanate (5.00 g, 30.3 mmoles) in dry THF (15 mL) was added dropwise over 10 min. with stirring at about −10° C. to ethyl-magnesium bromide (60.6 mmoles) in THF (30 mL). After 90 min. the reaction was quenched with saturated aqueous $NH_4Cl$ (25 mL) and extracted with EtOAc (3×50 mL). Organic extracts were pooled, washed with brine, dried over $MgSO_4$(s), filtered and concentrated in vacuo to afford the crude propionyl thioamide as a greenish-yellow oil (5.92 g; GC-MS m/z 195). This thioamide was cyclized without further purification using the alkaline $K_3Fe(CN)_6$ procedure as described in Preparation 1. The organic extracts from this reaction was flash chromatographed on silica using 10→5% EtOAc/hexanes to separate pure 7-methoxy-2-ethyl-benzothiazole (1.13 g), from its later eluting 5-methoxy isomer (1.53 g). The 7-methoxy derivative was deprotected using the pyridinium hydrochloride melt as described in Preparation 1 to produce 2-ethyl-benzotriazol-7-ol (0.790 g; GC-MS m/z 179).

PREPARATION 80

2-Isopropyl-benzothiazol-7-ol

The crude yellow solid thioamide (5.40 g) obtained from the reaction of isopropylmagnesium chloride (56 mmoles)

with 3-methoxyphenyl isothiocyanate (4.64 g, 28.1 mmol) in a manner analogous to that described in Preparation 79, was cyclized using the alkaline $K_3Fe(CN)_6$ methodology outlined in Preparation 1. The residue from the organic extracts was chromatographed on silica (10% EtOAc/hexanes) to resolve the faster eluting 7-methoxy-2-isopropyl-benzothiazole (2.27 g; GC-MS m/z 207) from its 5-methoxy isomer (1.1 g; GC-MS m/z 207). Deprotection using pyridinium hydrochloride for about 24 h at about 160° (see Preparation 1) afforded 2.00 g of crude product which was flash chromatographed (20% acetone/hexanes) to yield pure 2-isopropyl-benzothiazol-7-ol (1.18g; LC-MS m/z 194 (MH$^+$)).

PREPARATION 81

2-Butyl-benzothiazol-7-ol

This material was prepared by cyclization of the thioamide generated from 3-methoxyphenyl isothiocyanate (5.02 g; 30.4 mmol) and n-butyllithium (63 mmol), and subsequent deprotection of the resolved 7-methoxy derivative as described in Preparation 79.

PREPARATION 82

2-(2-Hydroxy-2-methyl)propyl-benzothiazol-7-ol

The 7-methoxy-2-methylbenzothiazole (720 mg, 4.0 mmol) produced in Preparation 1 was dissolved in dry THF (15 mL) and chilled to about −78° C. Phenyllithium (2.45 mL of 1.8 M in cyclohexane/Et$_2$O) was added dropwise over about 5 min. After stirring for about 10 min. at about −78° C., acetone (1.3 eq, 5.2 mmol, 385 µL) was added dropwise and stirring continued for about 10 min. at about −78° C. and about 1 h. at about 0° C. before quenching with 2M NH$_4$OAc (15 mL). EtOAc (15 mL) was added and the separated organic phase was washed with brine, dried over Na$_2$SO$_4$(s), filtered and concentrated in vacuo. The residue was flash chromatographed on silica (20→25% EtOAc/hexanes) to afford first recovered starting material (375 mg) followed by the desired 7-methoxy-2-[(2-hydroxy-2-methyl)propyl]-benzothiazole (430 mg). This material (388 mg) was dissolved in dry CH$_2$Cl$_2$ (5 mL), chilled to about −78° C. and treated with BBr$_3$(299 µL). The resulting solution was allowed to warm to about 20° C., and after about 5 h at about 20° C. was added dropwise with stirring to NaHCO$_3$ (1.33 g) in H$_2$O (25 mL) at about 5–10° C. The pH of the aqueous phase was adjusted to ~7 and extracted with CH$_2$Cl$_2$. The residue (360 mg) from the organic extracts containing 2-bromo and 2-hydroxy 2-adducts was hydrolyzed with silver(I) trifluoroacetate (1.1 g) in DMF (15 mL)/H$_2$O(80 mL) at about 20° C. for about 16 h. The mixture was treated with saturated Na$_2$CO$_3$ (20 mL) at about 60° C. for about 30 min., cooled to about 20° C., filtered through celite to remove precipitated Ag$_2$CO$_3$(s), pH adjusted to 6–7, and extracted with 15% i-PrOH/Et$_2$O (3×20 mL). Pooled organic extracts were washed with brine, dried over Na$_2$SO$_4$(s) and concentrated in vacuo to afford 219 mg of crude (≧75% pure by RP-HPLC) 2-(2-Hydroxy-2-methyl)propylbenzothiazol-7-ol (LC-MS m/z 224 (MH$^+$)) which was used without further purification.

PREPARATION 83

2-(Pyridin-4-yl)benzothiazol-7-ol

This material (LC-MS m/z 229 (MH$^+$)) was prepared from m-anisidine (13.71 g, 111.3 mmoles) and isonicotinoyl chloride hydrochloride (19.82 g, 111.3 mmol) utilizing the procedure as described for Preparation 33 for the acylation, conversion to the thioamide, $K_3Fe(CN)_6$ mediated cyclization and deprotection.

PREPARATION 84

2-(Morpholin-4-yl)benzothiazol-7-ol

Morpholine (7.93 g, 91.0 mmol) was added to 3-methoxyphenyl isothiocyanate (5.01 g, 30.3 mmol) in t-BuOH (15 mL) and the stirred mixture was heated to about 70° C. for about 3 h. Most of the solvent was removed in vacuo at about 35° C. and the concentrate was partitioned between CHCl$_3$ (100 mL) and 0.5 M aqueous HCl (100 mL). The organic phase was washed with 0.5 M HCl (2×50 mL) and brine, dried over MgSO$_4$(s), filtered and concentrated in vacuo to afford the crude thiourea as a light yellow powder (7.64 g; LC-MS m/z 253 (MH$^+$)). This material was cyclized using $K_3Fe(CN)_6$ according to the procedure outlined in Preparation 32. The residue from the resulting organic extracts was purified by flash chromatography on silica (20→30% EtOAc/hexanes) to afford 2.92 g of pure 7-methoxy-2-(morpholin-4-yl)benzothiazole (GC-MS m/z 250) and 0.915 g of the 5-methoxy isomer. Deprotection of the 7-methoxy derivative (2.92 g, 11.7 mmol) with molten pyridinium hydrochloride at about 160° C. as in Preparation 32 yielded 2-(morpholin-4-yl)benzothiazol-7-ol (1.85 g; LC-MS m/z 237 (MH$^+$).

PREPARATION 85

2-(4-Methyl-piperazin-1-yl)benzothiazol-7-ol

This material was prepared by the cyclization and deprotection of the thiourea obtained from the reaction of 3-methoxyphenyl isothiocyanate (5.01 g, 30.3 mmol) with N-methyl piperazine (15.16 g, 151.4 mmol) in refluxing t-BuOH in a manner analogous to that of Preparation 84. (LC-MS m/z 250 (MH$^+$)).

PREPARATION 86

2-(4-Trifluoroacetyl-piperazin-1-yl)benzothiazol-7-ol

The thiourea obtained from the reaction of 3-methoxyphenyl isothiocyanate (5.02 g, 30.4 mmol) with piperazine (13.01 g, 151 mmol) in refluxing t-BuOH was cyclized with $K_3Fe(CN)_6$ and subsequently deprotected with molten pyridinium hydrochloride at about 160° C. according to the procedure described for Preparation 84, but without the chromatographic separation of the 5- and 7- isomers. The resulting 2-(piperazinyl)-benzothiazol-5-ol and -7-ol mixture (2.35 g, 10 mmol) was dissolved in trifluoroacetic acid (20 mL) and chilled to about 0–5° C. Trifluoroacetic anhydride (3.4 mL, 24 mmol) was added dropwise over several minutes. After stirring for about 3 h. at about 20° C. the mixture was concentrated in vacuo at about 35° C. and then redissolved in H$_2$O (50 ml) with adjustment of the pH to 6–7 by careful addition of saturated aqueous K$_2$CO$_3$. The mixture was stirred for about 30 min. at about 20° C., diluted with H$_2$O (60 mL) and extracted with 5% MeOH in CH$_2$Cl$_2$ (1×100 mL, 2→40 mL). Pooled organic extracts were dried over Na$_2$SO$_4$(s) and concentrated in vacuo to afford a mixture of the 2-(4-trifluoroacetylpiperazin-1-yl) benzothiazol-5-ol and -7-ol isomers as a foamy solid (2.12 g; GC-MS m/z 331). The isomers were resolved by flash chromatography on silica (35% EtOAc/hexanes) to yield 820 mg of the pure 2-(4-trifluoroacetyl-piperazin-1-yl) benzothiazol-7-ol as the faster eluting isomer.

PREPARATION 87

1-(4-Fluoro-3-methyl-phenyl)cyclohexylamine

Cyclohexanone (5.0 mL, 47.5 mmol) was added dropwise at about 0° C. to 4-fluoro-3-methylphenyl magnesium bromide (50 mmol) in THF (50 mL). The mixture was allowed to warm to about 20° C. and stirred for about 1 h. The mixture was carefully added to 5% AcOH in $H_2O$ (100 mL) at about 5° C. and extracted with $Et_2O$ (150 mL). Organic extracts were dried over $Na_2SO_4$(s), filtered and concentrated in vacuo to a colorless syrup of crude 1-(4-fluoro-3-methyl)cyclohexanol (9.78 g, GC-MS m/z 208).

The alcohol from above (9.6 g) was dissolved in $CHCl_3$ (100 mL) and $NaN_3$(s) (10 g, 155 mmol) was added. The stirred mixture was cooled to about 0–5° C. and TFA (30 g) was added dropwise over about 5 min. After stirring for about 16 h. at about 20° C., $H_2O$ (150 mL) and $CHCl_3$ (150 mL) were added to the thick slurry. The organic phase obtained after about 10 minutes of stirring was washed with $H_2O$ (2×100 mL) and aqueous 5% $NaHCO_3$ (2×50 mL), dried over $Na_2SO_4$(s) and concentrated in vacuo to obtain the crude 1-(4-fluoro-3-methylphenyl)cyclohexyl azide (9.25 g, GC-MS m/z 233) which was reduced without further purification.

The crude azide (9.2 g, ≦44 mmol) was dissolved in MeOH (100 mL) at about 0–5° C. and Mg(s) (1.8 g of 40–80 mesh) was added in 3 portions over about 10 min. At about 1½ h. intervals additional Mg(s) (2×1.8 g) was added. The mixture was allowed to stir for about 16 h. at about 20° C. and then 2N $NH_4OH$ (200 mL) and $Et_2O$ (500 mL) were added. The mixture was filtered and the cake was washed with $Et_2O$. Pooled organic phases were washed with aqueous 5% $NaHCO_3$, dried over $MgSO_4$(s), filtered and concentrated in vacuo to afford 7.5 g crude amine as an oil. This residue was dissolved in dry $Et_2O$ (80 mL) and treated dropwise with 1M HCl in $Et_2O$ (35 mL) at about 5° C. while stirring. After 15 min. at about 5° C. the precipitated hydrochloride salt of 1-(4-fluoro-3-methylphenyl) cyclohexyl-1-amine was filtered, washed with $Et_2O$ and pet. ether and dried in vacuo (3.92 g; LC-MS m/z 208 (MH$^+$)).

PREPARATION 88

1-Phenylcyclohexylamine

1-Phenylcyclopentanol (16.3 g, 100 mmol) was treated with $NaN_3$(s) (20 g, 310 mmol) and TFA (65 g) in $CHCl_3$ (170 mL) at about 0–5° C., according to the procedure described in Preparation 87, to produce crude 1-phenyl-cyclohexylazide (18.6 g, GC-MS m/z 187).

The crude azide (18.0 g, ≦96 mmol) was dissolved in dioxane (300 mL) with triphenylphosphine (40 g, 152 mmol) and the stirred solution was refluxed for 4 h. under $N_2$ (g) before adding $H_2O$ (9 mL, 0.5 mol). After about 46 h. further reflux, solvent was removed in vacuo at about 45–50° C. and residual moisture was removed by azeotropic distillations in vacuo with $CH_3CN$ and $Et_2O$, respectively. The syrupy residue was dissolved in boiling $Et_2O$ and chilled to about 0° C. for about 16 h. Precipitated $Ph_3PO$ was removed by filtration, and 1M HCl in $Et_2O$ (90 mL) was added dropwise at about 5° C. to the etherol filtrate to precipitate the desired 1-phenyl-cyclohexylamine as its HCl salt (12.7 g, LC-MS m/z 162 (MH$^+$)) which was recrystallized from $CHCl_3$/i-$Pr_2O$ before use.

PREPARATION 89

1-(4-tert-Butyl-phenyl cyclohexylamine 4-tert-Butylphenylmagnesium bromide (100 mmol in 50 mL $Et_2O$) and cyclo-pentanone (8.0 mL, 90 mmol) were reacted in a manner analogous to that described in Preparation 87 to produce the intermediate alcohol and subsequently the azide. Crude azide (10.5 g, ≦43 mmol) was reduced with $Ph_3P/H_2O$ in dioxane as described in Preparation 88 to afford the desired 1-(4-tert-butylphenyl) cyclohexylamine which was isolated from $Et_2O$ by precipitation as its HCl salt (2.8 g; GC-MS m/z 217).

PREPARATION 90

2-Phenyl-decahydronaphthalen-2-ylamine

This material was prepared from cis/trans-2-tetralone and phenylmagnesium bromide utilizing a procedure analogous to those described in Preparation 89. The crude HCl salt of the amine was purified by preparative C18-RP-HPLC using a 15%→100% $CH_3CN$ pH 4.5, 50 mm $NH_4OAc$ gradient, followed by concentration in vacuo and extraction of the free-base into $Et_2OAc$ from 1N NaOH to obtain a 2:1 mixture of pure trans/cis-2-phenyl-decahydronaphthalen-2-ylamine.

PREPARATION 91

5-tert-Butyl-3-phenyl-bicyclo[2.2.1]hept-5-en-2-ylamine

2-Cyclopenten-1-one (14.2 mL, 0.17 mol) was added dropwise over about 30 min. at about −78° C. to t-BuLi (340 mmol) in dry THF (450 mL). The reaction was allowed to warm to about 20° C. and then chilled to about −78° C. to quench with $NH_4Cl$ (18.2 g). Solvent was removed in vacuo and the residue was partitioned between $Et_2O$ (300 mL) and brine (100 mL). The organic phase was washed with brine, dried over $MgSO_4$(s), filtered and concentrated in vacuo. The residue of crude 1-tert-butylcyclopent- 2-en-1-ol (23.8 g) was treated with benzenesulfonic acid (0.24 g) in refluxing $Et_2O$ for 1.5 h. Solvent was removed in vacuo and the residue was vacuum distilled (12 mm, ~27–30° C.) to obtain pure 2-tert-butylcyclopentadiene (4.2 g). This diene (1.3 g, 10.7 mmol) was dissolved in xylene (5 mL) along with a crystal of hydroquinone and trans-β-nitrostyrene (1.95 g, 13.1 mmol). The tube was sealed under $N_2$(g) and heated to about 140° C. for about 10 h. Flash chromatography on silica (30% $CH_2Cl_2$/hexanes) afforded 1.79 g (GC-MS m/z 271) of the nitro derivative which was reduced by dropwise addition of an etheral (10 mL) solution over 20 min. to $LiAlH_4$ (0.5 g) in $Et_2O$ (25 mL). The mixture was refluxed for about 5 h. and quenched by serial additions of $H_2O$ (0.5 mL), 15% NaOH (0.5 mL) and $H_2O$ (1.5 mL), respectively. The mixture was filtered and the filtrate was washed with saturated aqueous $NaHCO_3$ and brine, dried over $MgSO_4$(s), filtered, and concentrated in vacuo. The residue (1.1 g) was dissolved in dry $Et_2O$ (6 mL), chilled to about 5° C., and treated dropwise with 1M HCl in $Et_2O$ (6 mL) to precipitate the desired amine as its HCl salt (610 mg; LC-MS m/z 242).

PREPARATION 92

3-(2,6-Dichlorophenyl)bicyclo[2.2.1]hept-5-en-2-ylamine

Cyclopentadiene (2.39 g, 36.2 mmol) and 2,6-dichloro-omega-nitrostyrene (3.3 g, 15.1 mmol) in xylene (4 mL)

with a crystal of hydroquinone under $N_2(g)$ were heated in a sealed tube at about 120° C. for about 40 h. Flash chromatography on silica in 5% EtOAc/hexanes yielded 2.94 g of a mixture of the desired nitro intermediate and the nitro derivative resulting from a second Diels-Alder addition of cyclopentadiene to the initial desired product (LC-MS m/z 303 ($M+NH_4^+$) and 367 ($M+NH_4^+$), respectively). The 2.0 g of this mixture in $Et_2O$ (110 mL)/MeOH (14 mL)/$H_2O$ (6 mL) was treated with an excess of aluminum-amalgam at about 20° C. for about 6 h. The mixture was filtered through celite, and the filtrate was concentrated in vacuo. The residue was purified by preparative C18-RP-HPLC using a gradient from 5% to 100% $CH_3CN$/pH 4.5, 50 mM $NH_4OAc$, to yield the desired amine which was recovered as its free-base (370 mg; LC-MS m/z 254 ($MH^+$)) following concentration in vacuo and extraction into EtOAc from 1 M NaOH.

PREPARATION 93

3-(2-Chlorophenyl)bicyclo[2.2.1]hept-5-en-2-ylamine

This material (LC-MS m/z 220 ($MH^+$)) was prepared via the nitro derivative according to the procedure described in Preparation 92 but starting instead with 2-chloro-omega-nitrostyrene and cyclopentadiene.

PREPARATION 94 trans-2-Phenylcyciopent-1-ylamine

A mixture of 1-phenylcyclopentene (5.77 g, 40.0 mmol) and $Et_3SiH$ (40 mmol, 4.65 g, 6.40 mL) was added dropwise over about 10 min. at about −78° C. to 1.0 M $BCl_3$ in $CH_2Cl_2$ (40 mL, 40 mmol). The resulting solution was allowed to warm to about 20° C. and stirred for about 2.5 h. before the removal of the solvent in vacuo. The residue was dissolved in 1,2-dichloroethane (60 mL) and heated to about 60° C. before azidotrimethylsilane (4.83 g, 5.57 mL, 42 mmol) was added dropwise. MeOH (15 mL) was added and the mixture was refluxed for about 16 h. under $N_2$ (g).

$H_2O$ (60 mL) was added followed by conc. HCl (30 mL). The organic phase was separated and washed further with 3N HCl (2×30 mL). Pooled aqueous extracts were washed with $Et_2O$ (1×20 mL), and then the pH was adjusted to 13–14 with 6N NaOH. The crude free-base of the desired amine was extracted into $Et_2O$ (80 mL) and this ether extract was dried over $MgSO_4$(s), filtered and concentrated in vacuo to afford 1.1 g of a syrup. This residue was dissolved in $Et_2O$ (20 mL) and treated with 1M HCl in $Et_2O$ (8 mL, 8 mmol) at about 5° C. 2-Phenyl-cyclohex-1-ylamine (335g; LC-MS m/z 162 ($MH^+$)) was obtained as its pure HCl salt by filtration of the resulting precipitate, which was then washed with $Et_2O$ and recrystallized from $CHCl_3$/i-$Pr_2O$.

PREPARATION 95

2-Methyl-7-[2-(2-methyl-oxiranyl)-ethoxy]-benzothiazole

2-Methyl-7-hydroxybenzothiazoie was alkylated with 3-methyl-3-buten-1-ol according to Method VI. The product of this alkylation (0.30 g, 1.28 mmol) was dissolved in $CH_2Cl_2$ at about 0° C. to which was then added a solution of m-chloroperbenzoic acid (0.95 g, 5.53 mmol) in $CH_2Cl_2$. The reaction was allowed to warm to room temperature and after about 0.5 h the reaction was complete. 1N NaOH was added, the layers separated and the organic layer was washed with additional 1N NaOH and $H_2O$. The organic layer was then dried over $MgSO_4$ and the solvent was removed by rotary evaporation to give the title compound (0.20 g, 63%) as a yellow oil which was used in subsequent reactions without further purification.

PREPARATION 96

3-Amino-1-benzhydrylazetidine

3-Mesyloxy-1-benzhydrylazetidine (30.32 g, 95.5 mmol), potassium phthalimide (21.59 g, 116.53 mmol) and hexadecyl tributylphosphonium bromide (5.92 g, 11.7 mmol) were added to toluene (600 mL) and the mixture stirred at room temperature overnight. The reaction was then heated at reflux for 3 h. The solid was removed by filtration, washed with EtOAc and the combined organics then washed with $H_2O$. After drying over $Na_2SO_4$, the organics were treated with charcoal and then concentrated to an oil. Addition of isopropyl ether induced crystallization of the product (16.37 g, 46%).

The phthalimide protecting group was removed by treatment with hydrazine in methanol at reflux for 4 h. The solids were removed by filtration and the filtrate concentrated to give the title compound as a yellow oil (94%). This material was used without further purification.

PREPARATION 97

6-Allyl-2-methyl-7-(oxiran-2-ylmethoxy)

To 7-hydroxy-2-methylbenzothiazole (500 mg, 3.0 mmol) in DMF (3 mL) was added $K_2CO_3$ (459 mg, 3.32 mmol) followed by allyl bromide (287 uL, 3.32 mmol). The reaction was heated at about 50° C. for about 4 hours and then poured into water. The aqueous mixture was extracted with EtOAc, the combined organic layers were dried over $Na_2SO_4$, and the solvent then removed by rotary evaporation. The resulting oil crystallized on standing to give 7-allyloxy-2-methyl-benzothiazole as yellow crystals (440 mg, 71%); LSIMS m/z 206, m.p. 38–39° C.

In a small sublimation apparatus, 7-allyloxy-2-methylbenzothiazole (242 mg, 1.18 mmol) was heated at about 200° C. for about 5 minutes. Crystals were scraped from the cold fingers to give 6-allyl-7-hydroxy-2-methylbenzothiazole (150 mg, 62%) which was used in the next step without further purification.

The corresponding glycidyl ether was prepared from 6-allyl-7-hydroxy-2-methylbenzothiazole using Method 1 (94% yield).

PREPARATION 98

4-Chloro-7-hydroxy-2-methylbenzothiazole

6-Chloro-m-anisidine (5 g, 26 mmol) was disolved in $CH_2Cl_2$ to which was added triethylamine (3.6 mL, 26.4 mmol) and finally acetyl chloride (1.9 mL, 26.4 mmol) dropwise. The reaction was stirred at room temperature for several hours and then poured into water. The layers were separated and the organic dried over sodium sulfate. Solvent was removed by rotary evaporation to give 3-acetamide-4-chloroanisole (4.49 g, 95%) as a purple oil which was used without purification.

To the material above (4.4 g, 22 mmol) in toluene was added Lawesson's Reagent (18 g, 44 mmol) and the reaction heated at reflux for about 2 hours. After cooling to about 40° C., aqueous sodium carbonate was added and the mixture stirred with ether and the layers were separated. The aqueous layer was extracted with more ether and the combined organic layers were dried over sodium sulfate. The solvent was removed by rotary evaporation and the residue purified by column chromatography (silica gel, 9/2/0.5 $CH_2Cl_2$/hexanes/methanol) to give 4-chloro-3-thioacetamidoanisole (2.0 g, 42%) m.p. 92–93° C.; mass spec. m/z 216.

The above material was cyclized to 4-chloro-7-methoxy-2-methylbenzothiazole by the method described in Prepartion 1.

The title compound was prepared from 4-chloro-7-methoxy-2-methylbenzothiazole by cleavage of the methyl ether with pyridine hydrochloride as described in Preparation 1, m.p. 225° C. (decomposition), mass spec. m/z 200.

What is claimed is:

1. A compound slected from the following compounds, or a pharmaceutically-acceptable salt thereof:

1-[4-(10,11-dihydro-5H-dibenzo[a,d]cyclohepten-5-yl)-piperazin-1-yl]-3-(3-methyl-3H-benzoimidazol-4-yloxy)-propan-2-ol, 1-[4-(10,11-dihydro-5H-dibenzo[a,d]cyclohepten-5-yl)-piperazin-1-yl]-3-(3-methyl-3H-benzotriazol-4-yloxy)-propan-2-ol, 1-(benzothiazol-7-yloxy)-3-[4-(10,11-dihydro-5H-dibenzo[a,d]cyclohepten-5-yl)-piperazin-1-yl)-propan-2-ol, 1-[4-(10,11-dihydro-5H-dibenzo[a,d]cyclohepten-5-yl)-piperazin-1-yl]-3-(2-methyl-benzo-thiazol-7-yloxy)-propan-2-ol, 1-[4-(10,11-dihydro-5H-dibenzo[a,d]cyclohepten-5-yl)-piperazin-1-yl]-3-(2-dimethyl-amino-benzothiazol-7-yloxy)-propan-2-ol, 7-{3-[4-(10,11-dihydro-5H-dibenzo[a,d]cyclohepten-5-yl)-piperazin-1-yl]-2-hydroxy-propoxy}-benzothiazol-2-carboxylic acid amide, and 1-[4-(10,11-dihydro-5H-dibenzo[a,d]cyclohepten-5-yl)-piperazin-1-yl]-3-(2-pyridin-3-yl-benzothiazol-7-yloxy)-propan-2-ol.

2. A compound selected from the following compounds, or a pharmaceutically-acceptable salt thereof:

1-[4-(10,11-dihydro-5H-dibenzo[a,d]cyclohepten-5-yl)-piperazin-1-yl]-3-(2-methyl-benzothiazol-7-yloxy)-propan-2-ol, 1-[4-(10,11-dihydro-5H-dibenzo[a,d]cyclohepten-5-yl)-piperazin-1-yl]-3-(2-dimethylamino-benzothiazol-7-yloxy)-propan-2-ol, 7-{3-[4-(10,11-dihydro-5H-dibenzo[a,d]cyclohepten-5-yl)-piperazin-1-yl]-3-(2-hydroxy-propoxy}-benzothiazol-2-carboxylic acid amide, 1-[4-(10,11-dihydro-5H-dibenzo[a,d]cyclohepten-5-yl)-piperazin-1-yl]-3 (2-pyridin-4-yl benzothiazol-7-yloxy)-propan-2-ol, 1-[4-(10,11-dihydro-5H-dibenzo[a,d]cyclohepten-5-yl)-piperazin-1-yl]-3-(2-isopropyl-benzothiazol-7-yloxy)-propan-2-ol, and 1-[4-(10,11-dihydro-5H-dibenzo[a,d]cyclohepten-5-yl)-piperazin-1-yl]-3-(3-methyl-3H-benzoimidazol-4-yloxy)-propan-2-ol.

3. A method of inhibiting a P-glycoprotein in a human suffering from cancer which comprises administering to said human a P-glycoprotein inhibiting amount of a compound according to claim 1, or a pharmaceutically acceptable salt thereof, wherein said compound is administered before, with or after the administration to said human of an anticancer effective amount of a chemotherapeutic agent.

4. A method of inhibiting a P-glycoprotein in a human suffering from cancer which comprises administering to said human a P-glycoproteininhibiting amount of a compound according to claim 2, or a pharmaceutically acceptable salt thereof, wherein said compound is administered before, with or after the administration to said human of an anticancer effective amount of a chemotherapeutic agent.

* * * * *